(12) United States Patent
Scianamblo

(10) Patent No.: US 9,271,740 B2
(45) Date of Patent: Mar. 1, 2016

(54) PRECESSIONAL-MOTION BONE AND DENTAL DRILLING TOOLS AND BONE HARVESTING APPARATUS

(71) Applicant: Michael J. Scianamblo, Tiburon, CA (US)

(72) Inventor: Michael J. Scianamblo, Tiburon, CA (US)

( * ) Notice: Subject to any disclaimer, the term of this patent is extended or adjusted under 35 U.S.C. 154(b) by 0 days.

(21) Appl. No.: 14/464,597

(22) Filed: Aug. 20, 2014

(65) Prior Publication Data

US 2015/0057664 A1   Feb. 26, 2015

Related U.S. Application Data

(60) Provisional application No. 61/868,276, filed on Aug. 21, 2013, provisional application No. 61/899,705, filed on Nov. 4, 2013.

(51) Int. Cl.
*A61B 17/16* (2006.01)
*B23B 51/00* (2006.01)
*A61C 3/02* (2006.01)
(Continued)

(52) U.S. Cl.
CPC .......... *A61B 17/1615* (2013.01); *A61B 17/164* (2013.01); *A61C 3/02* (2013.01); *B23B 51/00* (2013.01); *B23B 51/0081* (2013.01); *B23B 51/02* (2013.01); *B28D 1/14* (2013.01); *B28D 1/146* (2013.01); *B23B 2250/16* (2013.01); *B23B 2251/204* (2013.01); *B23B 2251/244* (2013.01); *B23B 2251/245* (2013.01); *Y10T 408/03* (2015.01); *Y10T 408/455* (2015.01); *Y10T 408/89* (2015.01); *Y10T 408/905* (2015.01); *Y10T 408/909* (2015.01); *Y10T 408/9097* (2015.01); *Y10T 409/303808* (2015.01)

(58) Field of Classification Search
CPC .................................. A61C 5/023; A61C 3/02
USPC .................................. 433/102; 408/113, 114
See application file for complete search history.

(56) References Cited

U.S. PATENT DOCUMENTS 2,930,264 A   3/1960   Lovert
3,400,617 A   9/1968   Sanborn
(Continued)

FOREIGN PATENT DOCUMENTS

EP   0 120 542   10/1984
EP   0 987 076   3/2000
(Continued)

OTHER PUBLICATIONS

International Search Report and Written Opinion of International Patent Application No. PCT/US2014/051916, filed Aug. 20, 2014. Received Feb. 4, 2015. 18 pages.
(Continued)

*Primary Examiner* — Matthew Lawson
(74) *Attorney, Agent, or Firm* — Fish & Richardson P.C.

(57) ABSTRACT

This document provides orthopedic and dental devices and methods for their use. For example, novel bone drills and dental drills are described. The bone and dental drills have at least some centers of mass that are offset from the drills' axis of rotation. Accordingly, the bone and dental drills may rotate and cut using a precessional pattern of motion. The design facilitates bone cutting, chip formation and hauling capacity, irrigation and bone harvesting. In some embodiments, the bone chips are collected in a removable apparatus fixed to the distal portion of the drill, and the collected bone chips can be used for bone grafting.

37 Claims, 31 Drawing Sheets

(51) Int. Cl.
  *B23B 51/02* (2006.01)
  *B28D 1/14* (2006.01)

(56) References Cited

U.S. PATENT DOCUMENTS

| | | | |
|---|---|---|---|
| 3,824,026 A | 7/1974 | Gaskins | |
| 4,044,468 A | 8/1977 | Kahn | |
| 4,190,386 A | 2/1980 | Brabetz et al. | |
| 4,231,692 A | 11/1980 | Brabetz et al. | |
| 4,332,561 A | 6/1982 | McSpadden | |
| 4,353,698 A | 10/1982 | McSpadden | |
| 4,456,411 A | 6/1984 | Clement | |
| 4,457,710 A | 7/1984 | McSpadden | |
| 4,536,159 A | 8/1985 | Roane | |
| 4,538,989 A | 9/1985 | Apairo, Jr. et al. | |
| 4,842,451 A * | 6/1989 | Dugger | B23B 51/02 408/21 |
| 4,889,487 A | 12/1989 | Lovaas | |
| 4,934,934 A | 6/1990 | Arpaio, Jr. et al. | |
| 4,992,048 A | 2/1991 | Goof | |
| 5,106,298 A | 4/1992 | Heath et al. | |
| 5,464,362 A | 11/1995 | Heath et al. | |
| 5,498,158 A | 3/1996 | Wong | |
| 5,503,554 A | 4/1996 | Schoeffel | |
| 5,584,617 A | 12/1996 | Houser | |
| 5,605,460 A | 2/1997 | Heath et al. | |
| 5,658,145 A | 8/1997 | Maillefer et al. | |
| 5,676,541 A | 10/1997 | Maillefer et al. | |
| 5,713,736 A | 2/1998 | Heath et al. | |
| 5,752,825 A | 5/1998 | Buchanan | |
| 5,775,904 A | 7/1998 | Riitano | |
| 5,836,764 A | 11/1998 | Buchanan | |
| 5,842,862 A | 12/1998 | Nissan | |
| 5,882,198 A * | 3/1999 | Taylor et al. | 433/102 |
| 5,897,274 A | 4/1999 | Ogura et al. | |
| 5,897,316 A | 4/1999 | Buchanan | |
| 5,902,106 A | 5/1999 | McSpadden | |
| 5,921,775 A | 7/1999 | Buchanan | |
| 5,938,440 A | 8/1999 | McSpadden | |
| 5,984,679 A | 11/1999 | Farzin-Nia et al. | |
| 6,106,296 A | 8/2000 | Johnson | |
| 6,299,445 B1 | 10/2001 | Garman | |
| 6,315,558 B1 | 11/2001 | Farzin-Nia et al. | |
| 6,419,488 B1 | 7/2002 | McSpadden et al. | |
| 6,575,748 B1 | 6/2003 | Filhol | |
| 6,702,579 B1 | 3/2004 | Hoppe et al. | |
| 6,890,134 B1 | 5/2005 | Wagner et al. | |
| 6,929,078 B1 | 8/2005 | Randall | |
| 6,942,484 B2 | 9/2005 | Scianamblo | |
| 7,094,056 B2 | 8/2006 | Scianamblo | |
| 7,125,252 B2 | 10/2006 | Rouiller et al. | |
| 7,717,710 B2 | 5/2010 | Danger et al. | |
| 7,955,078 B2 | 6/2011 | Scianamblo | |
| 8,454,361 B2 | 6/2013 | Scianamblo | |
| 8,496,476 B2 | 7/2013 | Scianamblo | |
| 8,727,680 B2 | 5/2014 | Wada et al. | |
| 8,882,504 B2 | 11/2014 | Scianamblo | |
| 2002/0031745 A1* | 3/2002 | Kumar et al. | 433/165 |
| 2004/0023186 A1 | 2/2004 | McSpadden | |
| 2004/0042865 A1 | 3/2004 | Oettle | |
| 2004/0131993 A1 | 7/2004 | Rouiller et al. | |
| 2004/0185414 A1 | 9/2004 | Badoz | |
| 2004/0219485 A1 | 11/2004 | Scianamblo | |
| 2004/0253379 A1 | 12/2004 | Sugita et al. | |
| 2004/0265775 A1 | 12/2004 | Maillefer et al. | |
| 2005/0026109 A1 | 2/2005 | Buchanan | |
| 2005/0117984 A1 | 6/2005 | Eason et al. | |
| 2005/0266375 A1 | 12/2005 | Brock et al. | |
| 2005/0282117 A1* | 12/2005 | Aravena et al. | 433/224 |
| 2006/0068362 A1* | 3/2006 | Desrosiers et al. | 433/102 |
| 2006/0111724 A1 | 5/2006 | Ping | |
| 2006/0115650 A1 | 6/2006 | Hanyu et al. | |
| 2006/0228668 A1 | 10/2006 | McSpadden | |
| 2006/0228669 A1* | 10/2006 | Scianamblo | 433/102 |
| 2007/0015107 A1 | 1/2007 | Mannschedel et al. | |
| 2007/0059663 A1 | 3/2007 | Scianamblo | |
| 2007/0082318 A1* | 4/2007 | Breguet | 433/102 |
| 2007/0184406 A1 | 8/2007 | Mason | |
| 2009/0047080 A1 | 2/2009 | Schweighofer et al. | |
| 2010/0221078 A1 | 9/2010 | Borschert | |
| 2011/0236853 A1* | 9/2011 | Shimoo | 433/82 |
| 2012/0039680 A1 | 2/2012 | Koike et al. | |
| 2012/0282571 A1* | 11/2012 | Ammon | A61C 5/023 433/102 |
| 2013/0170920 A1 | 7/2013 | Ogawa | |
| 2013/0189644 A1* | 7/2013 | Johnson | A61C 5/023 433/102 |
| 2013/0273497 A1 | 10/2013 | Scianamblo | |
| 2013/0302749 A1 | 11/2013 | Scianamblo | |

FOREIGN PATENT DOCUMENTS

| | | |
|---|---|---|
| EP | 1 184 004 | 3/2002 |
| EP | 1 213 074 | 6/2002 |
| FR | 2 798 277 | 3/2001 |
| FR | 2854054 | 10/2004 |
| JP | 52-156494 | 12/1977 |
| JP | 57-127608 | 8/1982 |
| JP | 62-241606 | 10/1987 |
| JP | 06-320323 | 11/1994 |
| JP | 11-019812 | 1/1999 |
| JP | 2002-144122 | 5/2002 |
| JP | 2002-205213 | 7/2002 |
| JP | 2007-0283473 | 11/2007 |
| SU | 637207 | 12/1978 |
| WO | WO 02/065938 | 8/2002 |
| WO | WO 2004/098438 | 11/2004 |
| WO | WO 2009/001681 | 12/2008 |
| WO | WO2014/118591 | 8/2014 |

OTHER PUBLICATIONS

"Protaper Next". Dentsply Tulsa Dental Specialties. Last updated Dec. 5, 2014. Retrieved on Dec. 5, 2014. Retrieved from the internet: URC:<http://www.tulsadentalspecialties.com/default/endodontics_brands/PROTAPERNEXT.aspx>. 1 page.

International Search Report and Written Opinion of International Patent Application No. PCT/US2014/051909, filed Aug. 20, 2014. Received Dec. 22, 2014. 18 pages.

Ultimate Handyman. *Drilling Through Walls*. YouTube. Published Sep. 23, 2011. Retrieved on Nov. 11, 2014. Retrieved from the internet: URL<https://www.youtube.com/watch?v=fpFUx1cH2Lg>.

Partial European Search Report, European Application Serial No. EP 06 00 7527, Jun. 26, 2006, 6 pages.

EP 04 75 1290 Supplementary European Search Report, Jun. 5, 2007, 5 pages.

EP 04 75 0878 Supplementary European Search Report, Jun. 5, 2007, 3 pages.

Communication pursuant to Article 94(3) EPC for Application No. EP 06 00 7527.2-1265, dated Jun. 17, 2009, 5 pages.

Linear definition from Merriam-Webster on-line. Retrieved on Feb. 20, 2009, from http://www.merriam-webster.com/dictionary/linear, 3 pages.

Straight. (n.d.). Dictionary.com Unabridged. Retrieved Feb. 11, 2010, from Dictionary.com website: http://dictionary.reference.com/browse/straight, 12 pages.

USPTO Non-Final Office Action in U.S. Appl. No. 11/402,207, mailed Feb. 26, 2009, 16 pages.

USPTO Final Office Action in U.S. Appl. No. 11/402,207, mailed Oct. 6, 2009, 9 pages.

USPTO Non-Final Office Action in U.S. Appl. No. 11/402,207, mailed Feb. 19, 2010, 10 pages.

USPTO Non-Final Office Action in U.S. Appl. No. 11/226,059, mailed Mar. 31, 2008, 5 pages.

(56) References Cited

OTHER PUBLICATIONS

USPTO Final Office Action in U.S. Appl. No. 11/226,059, mailed May 13, 2009, 8 pages.
USPTO Non-Final Office Action in U.S. Appl. No. 11/226,059, mailed Oct. 21, 2009, 9 pages.
USPTO Final Office Action in U.S. Appl. No. 11/226,059, mailed May 17, 2010, 9 pages.
Office Action in U.S. Appl. No. 11/402,207, mailed Aug. 25, 2010, 13 pages.
USPTO Non-Final Office Action in U.S. Appl. No. 11/402,207, mailed Aug. 28, 2012, 7 pages.

* cited by examiner

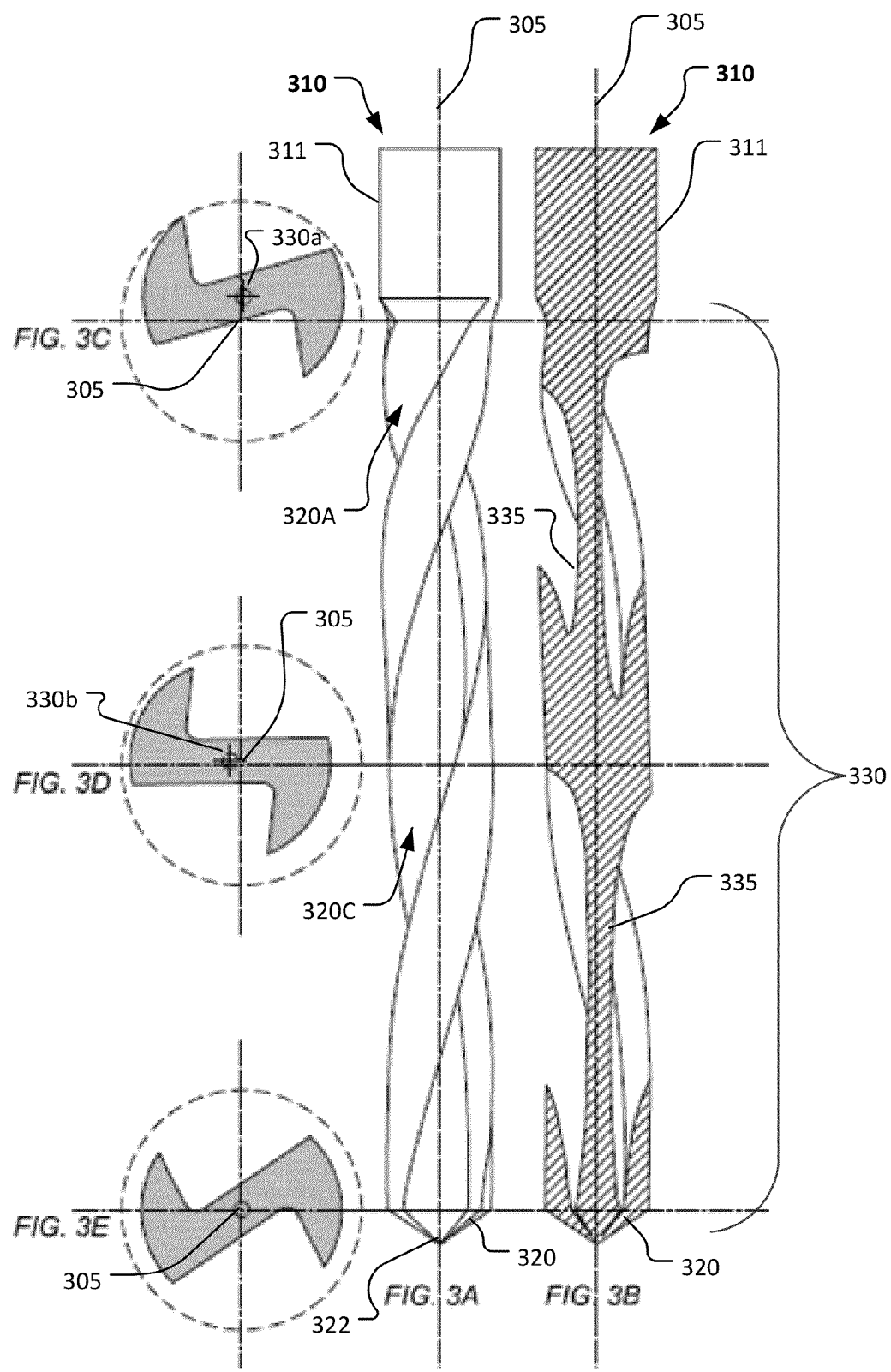

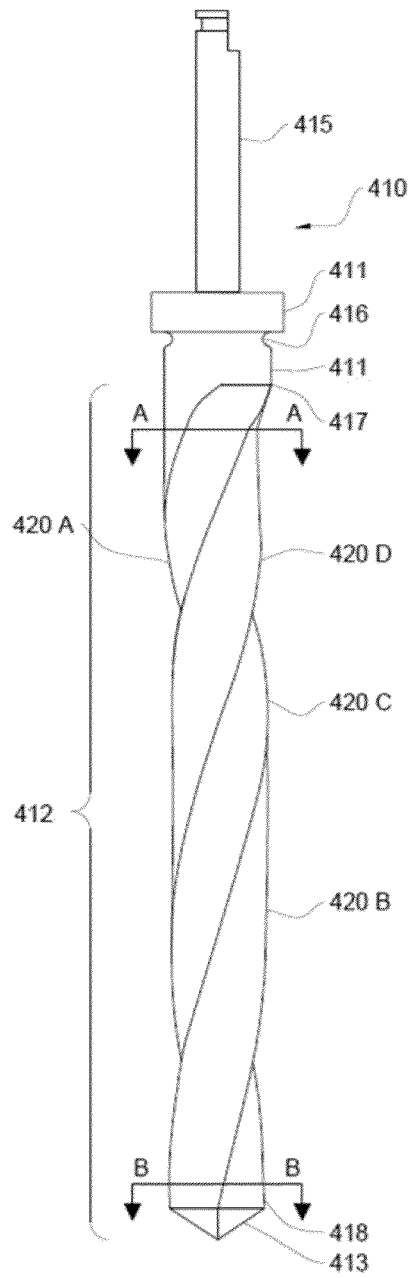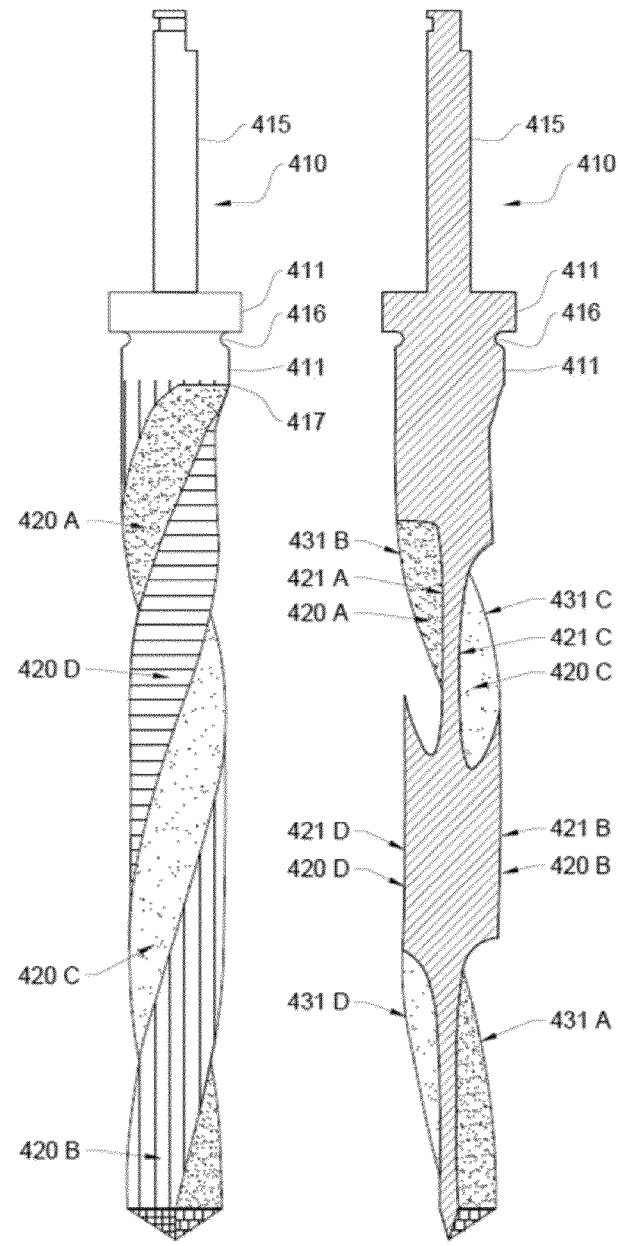
FIG. 4A  FIG. 4B  FIG. 4C

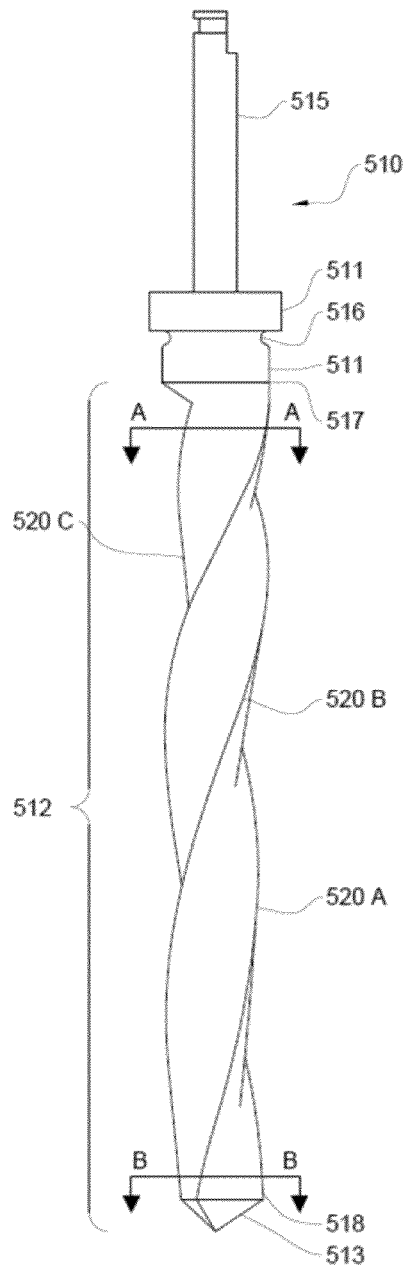
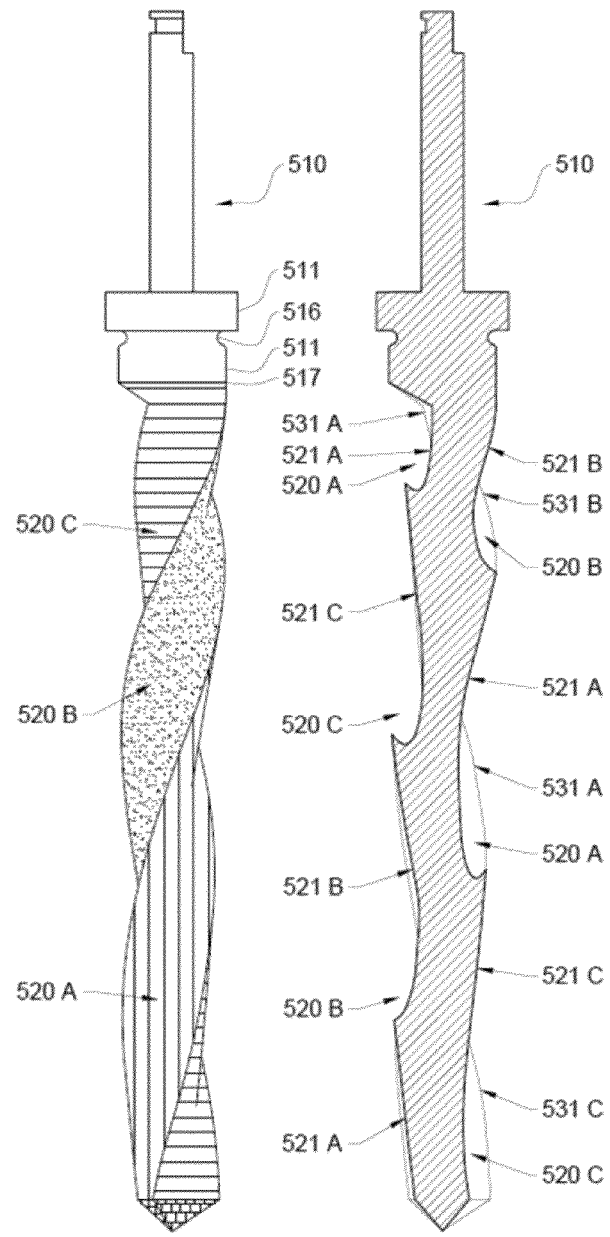
FIG. 5A  FIG. 5B  FIG. 5C

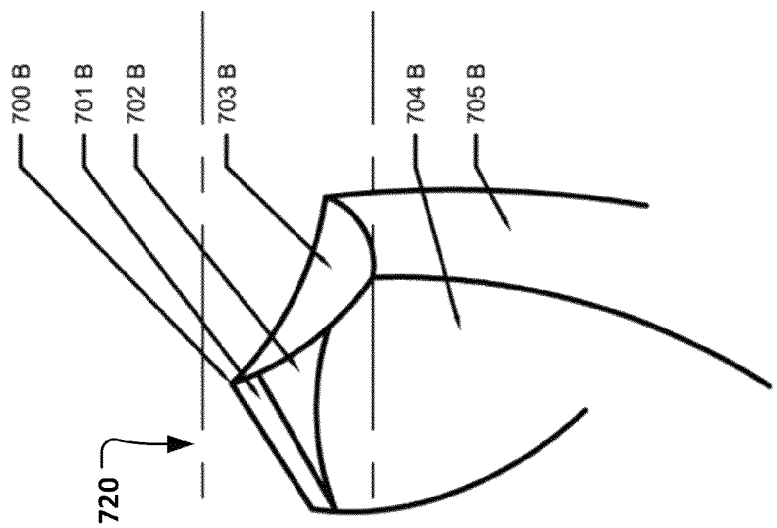
FIG. 7B1
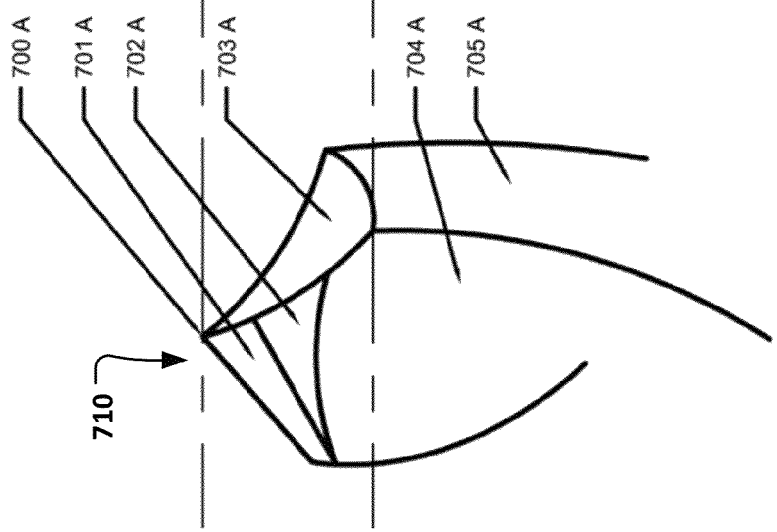
FIG. 7A1
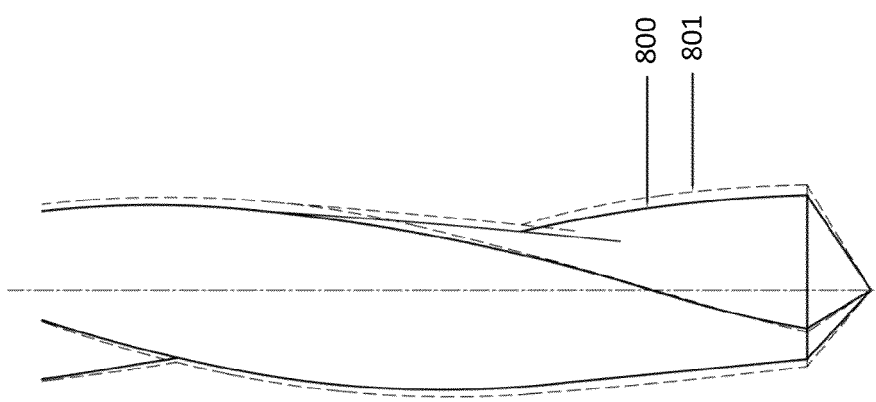
FIG. 6G

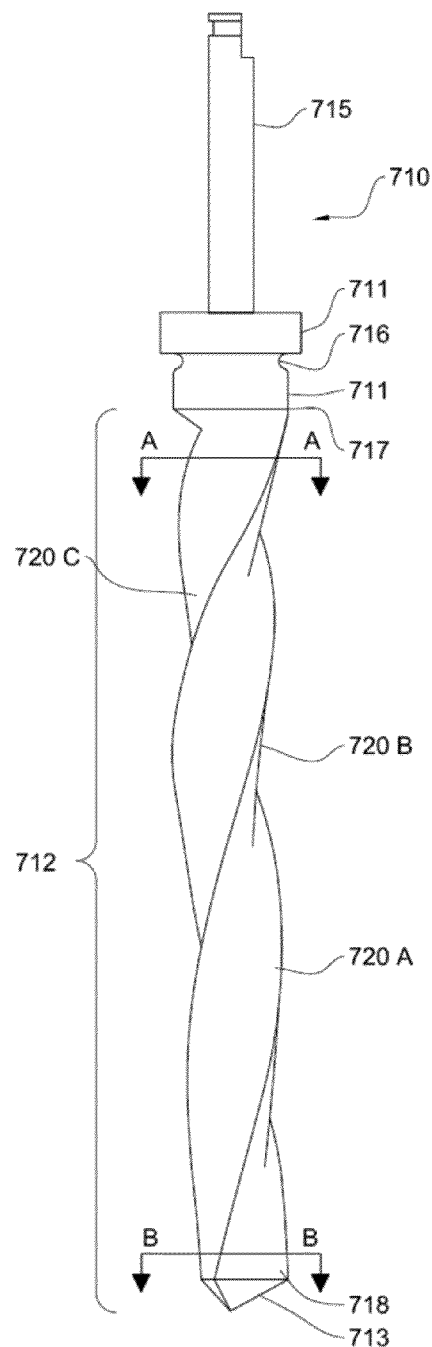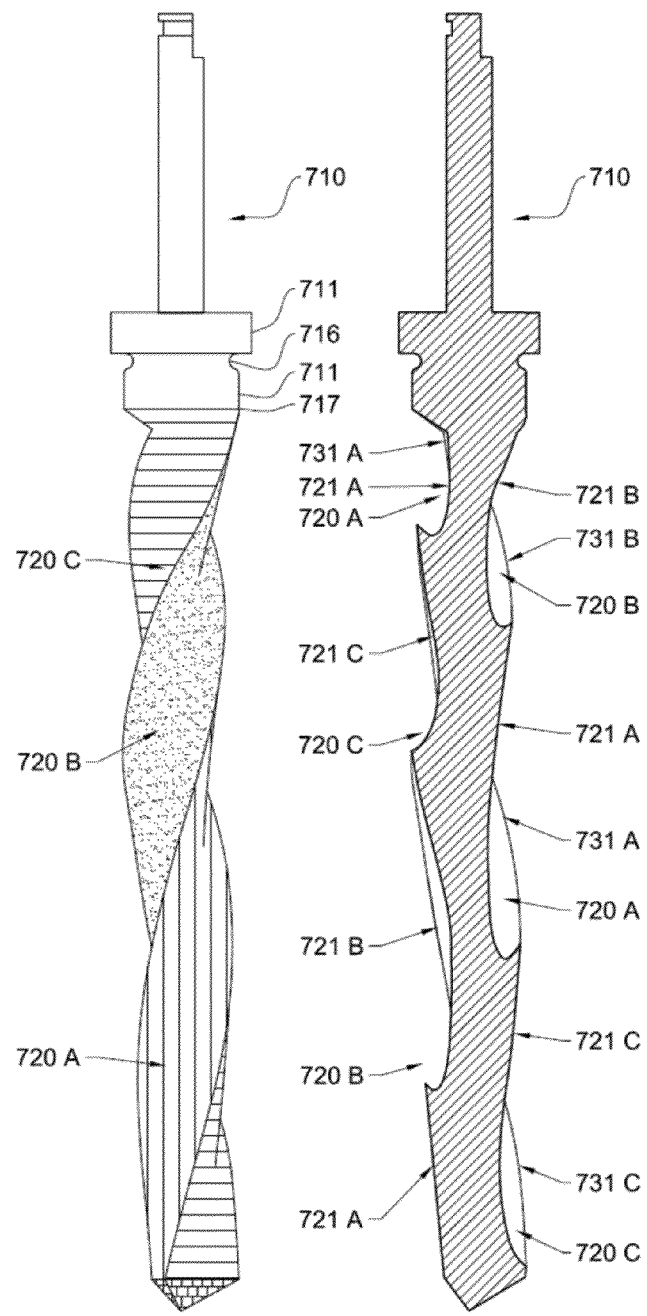
FIG. 7A    FIG. 7B    FIG. 7C

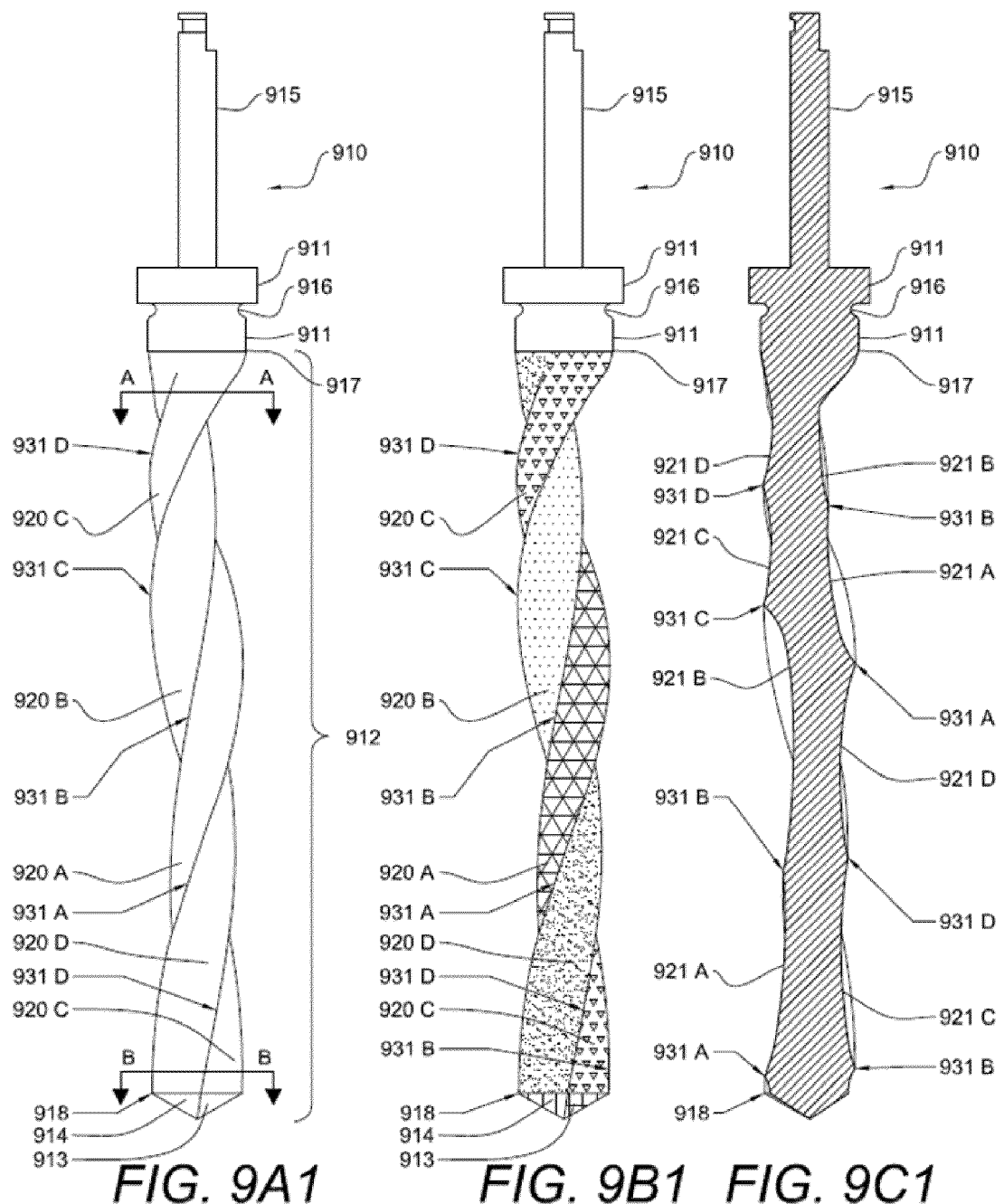
FIG. 9A1  FIG. 9B1  FIG. 9C1

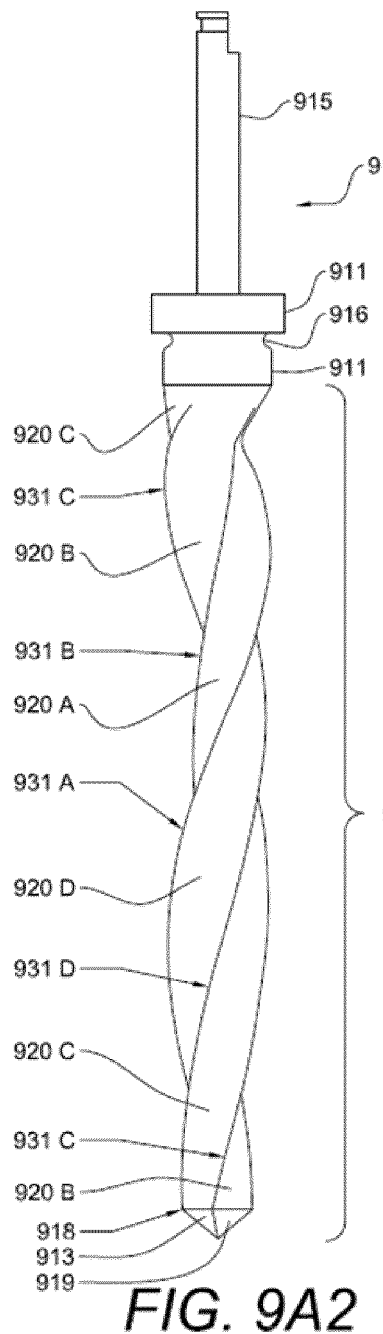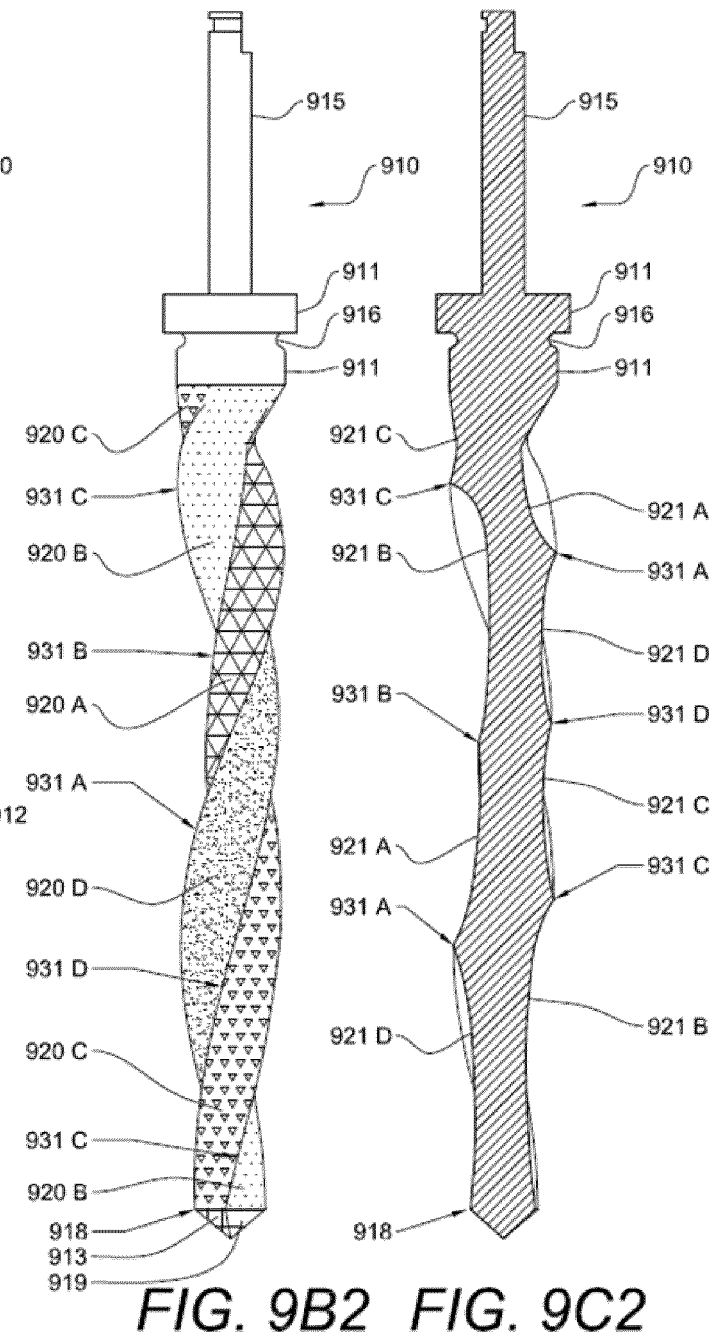
FIG. 9A2  FIG. 9B2  FIG. 9C2

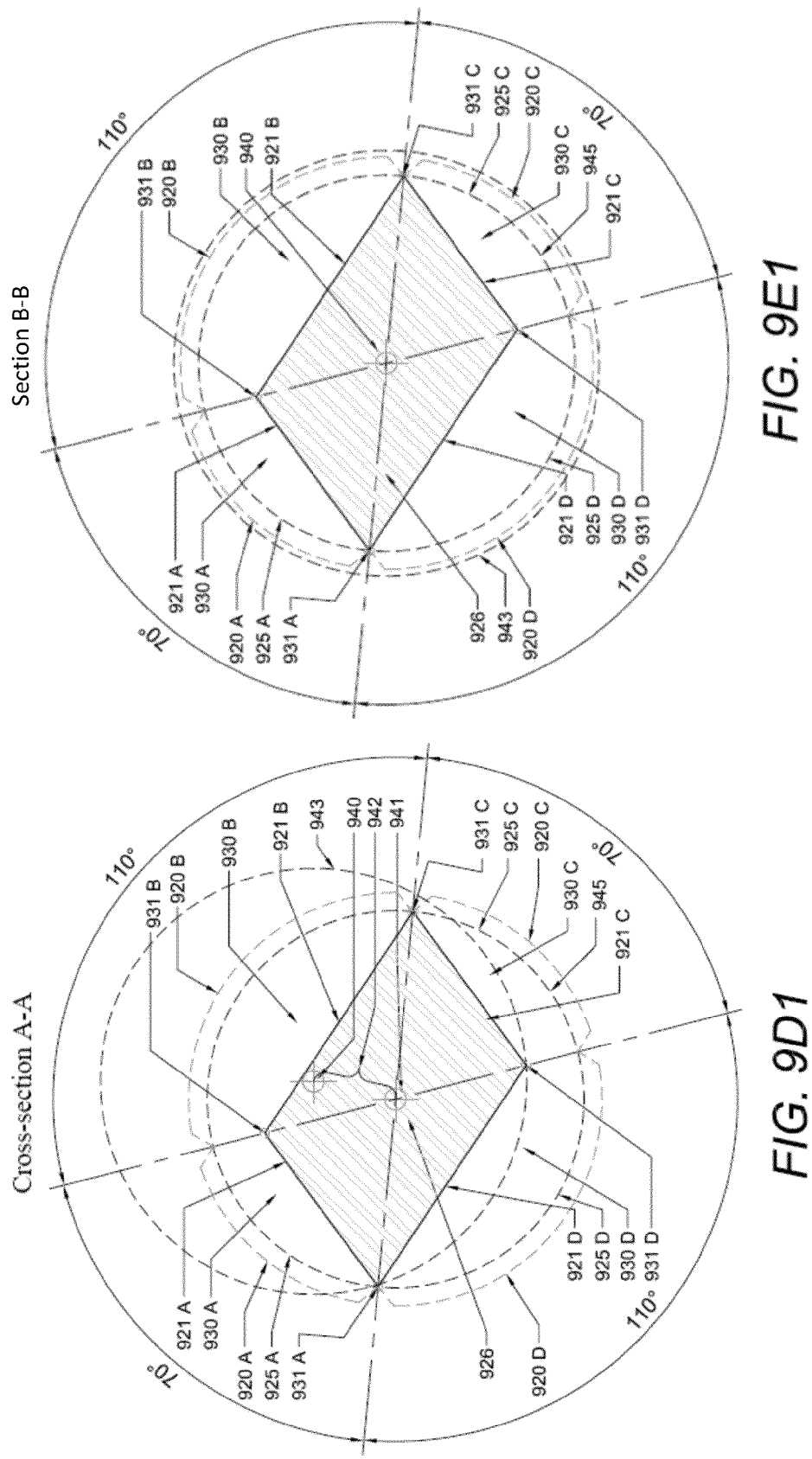

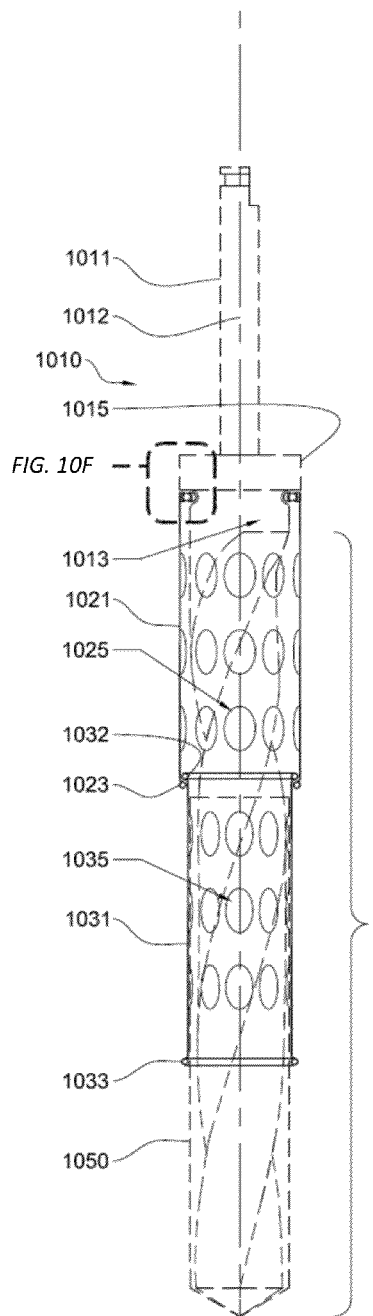
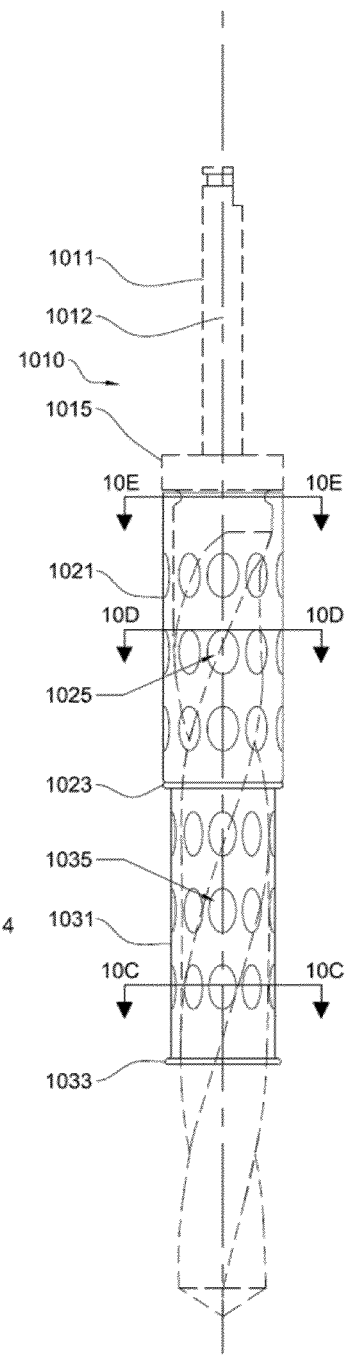
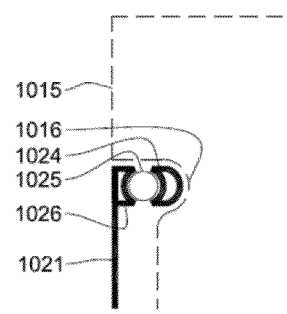
FIG. 10F
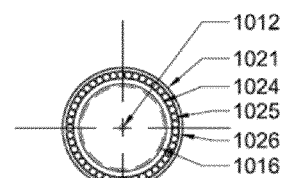
FIG. 10E
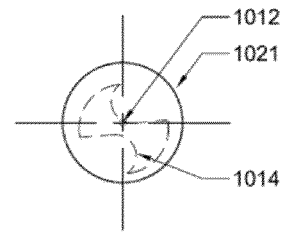
FIG. 10D
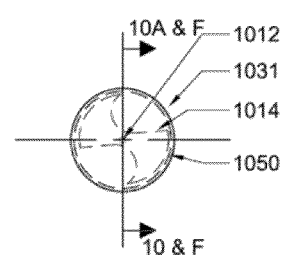
FIG. 10A  FIG. 10B  FIG. 10C

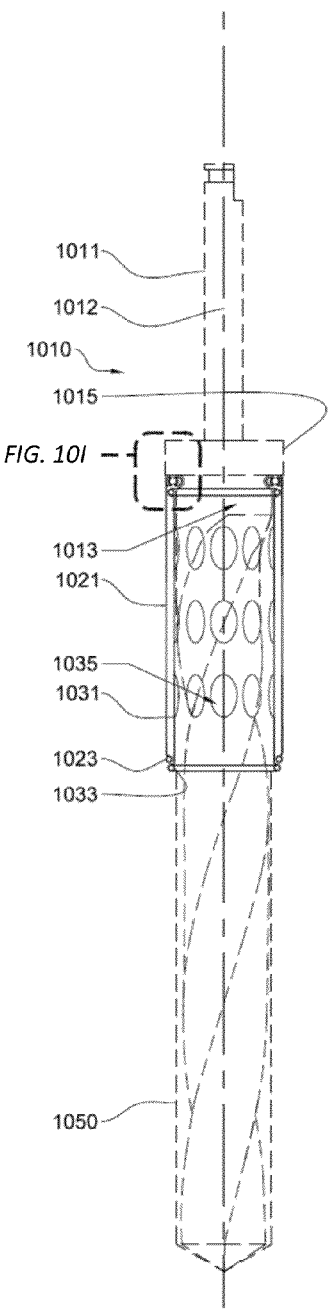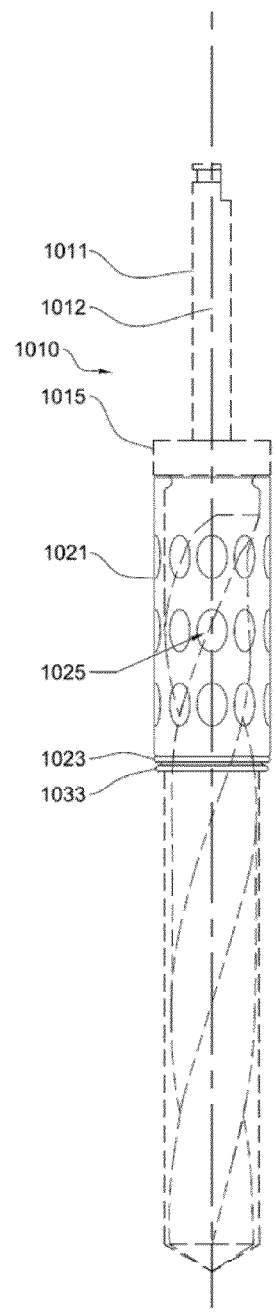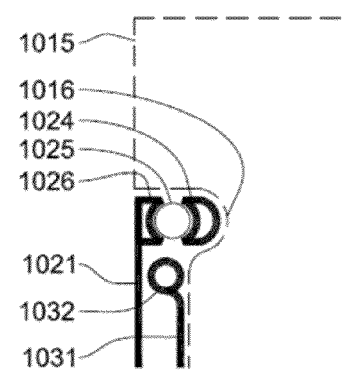
FIG. 10I
FIG. 10G   FIG. 10H

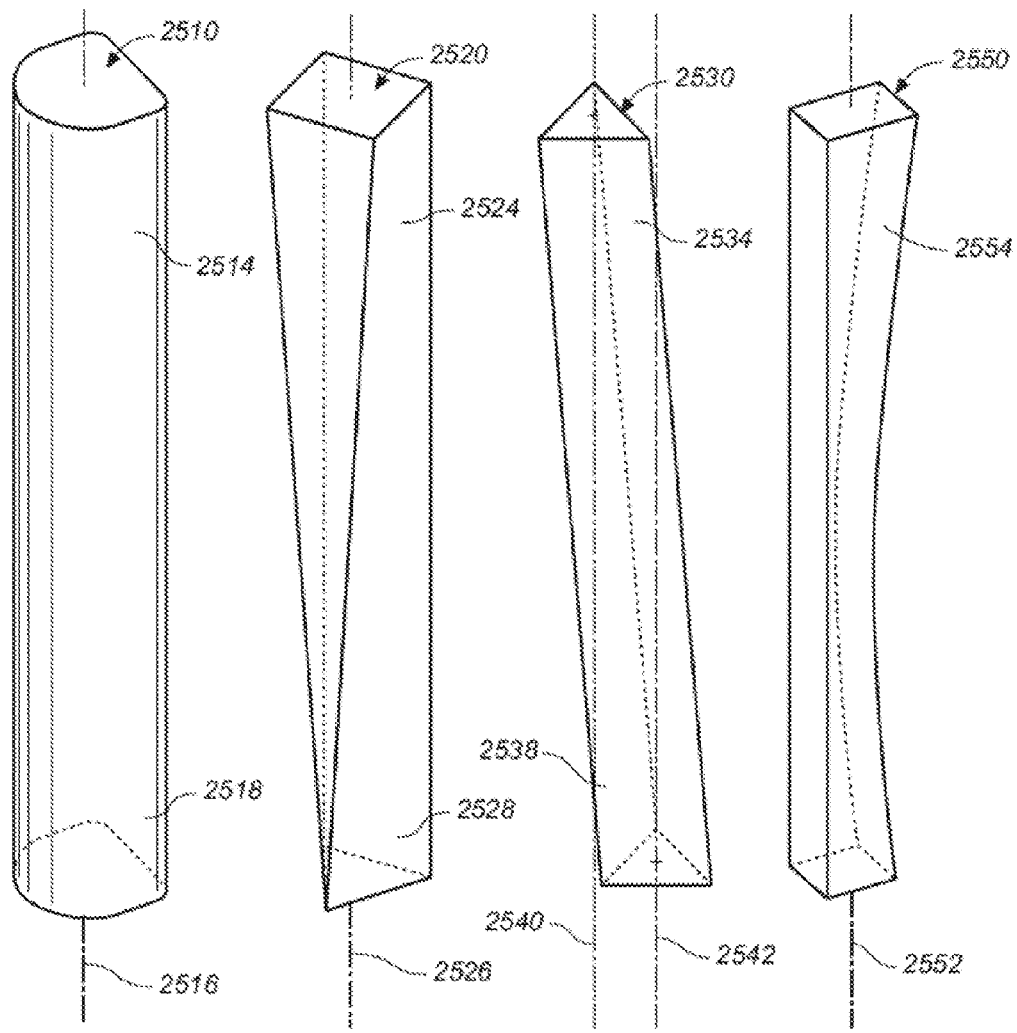
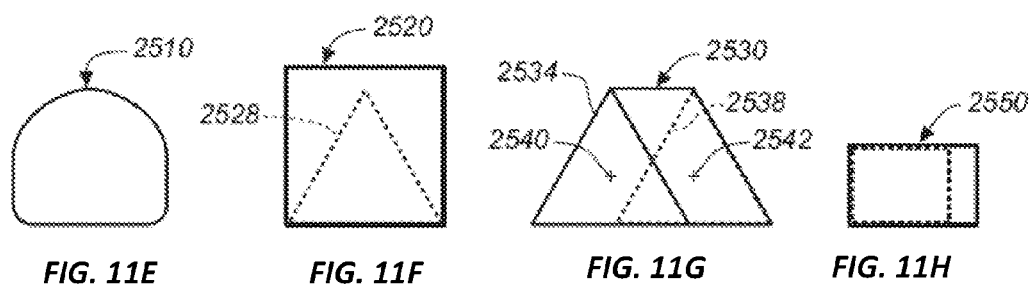
FIG. 11A  FIG. 11B  FIG. 11C  FIG. 11D
FIG. 11E  FIG. 11F  FIG. 11G  FIG. 11H

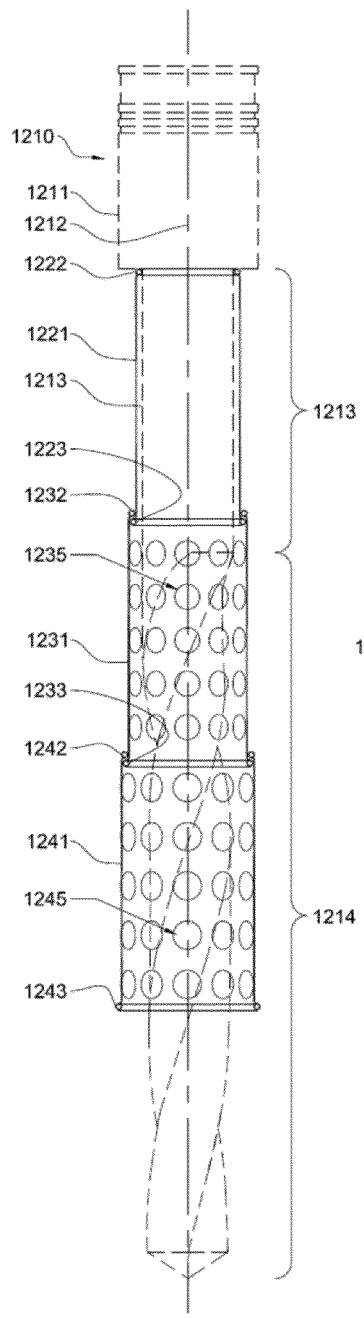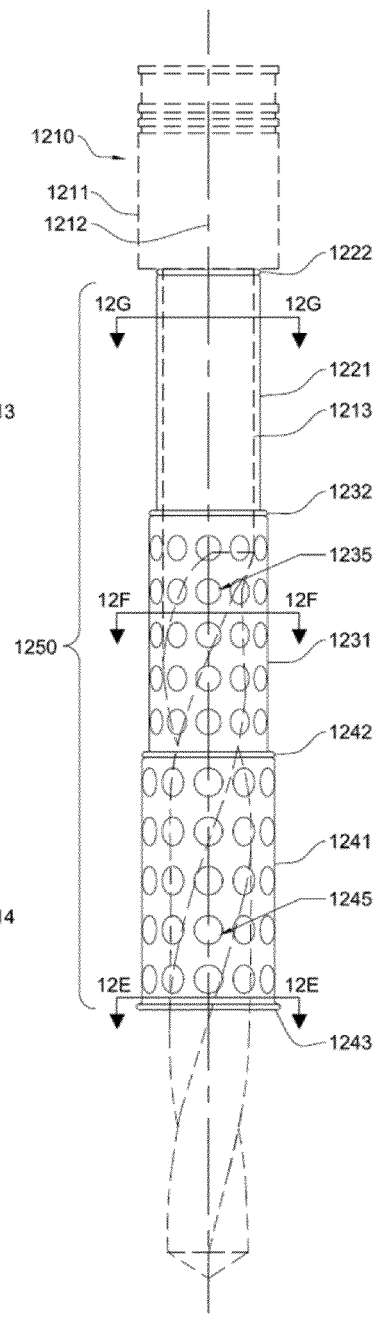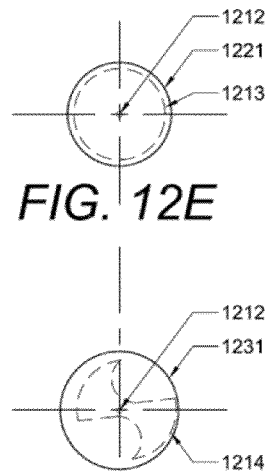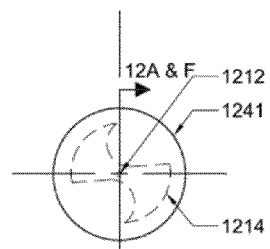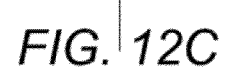
FIG. 12A  FIG. 12B

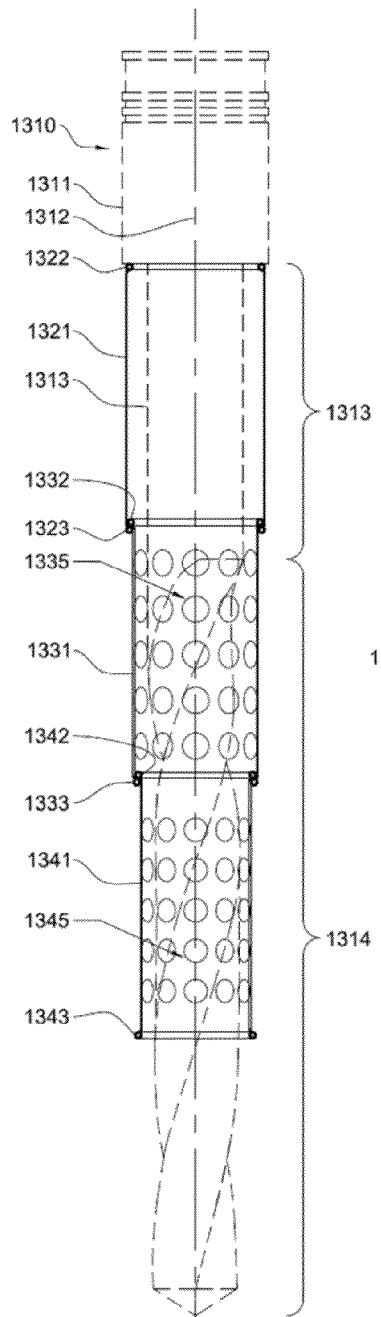
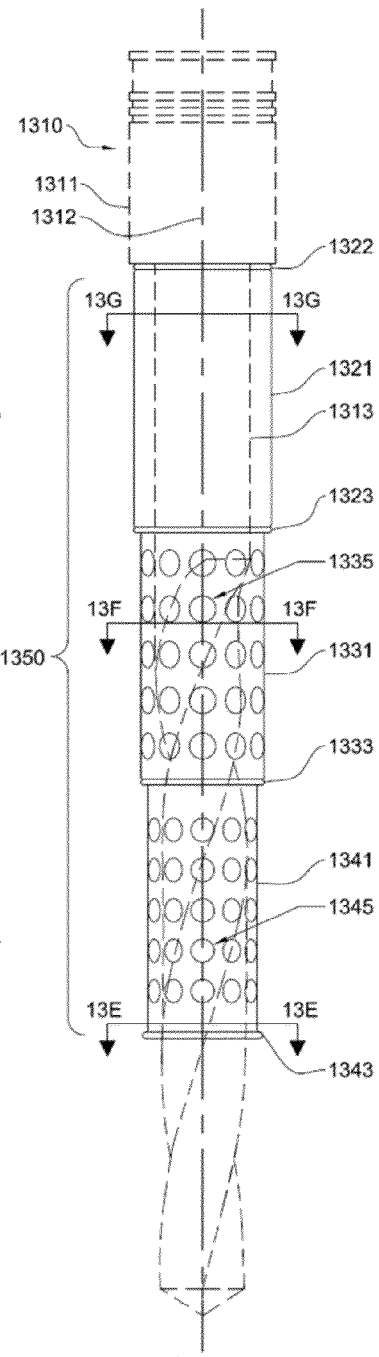
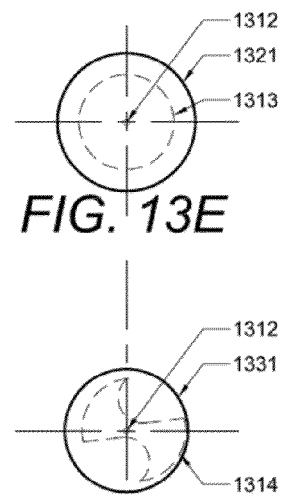
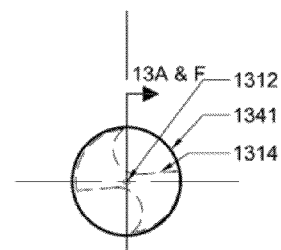
FIG. 13A
FIG. 13B
FIG. 13E
FIG. 13D
FIG. 13C

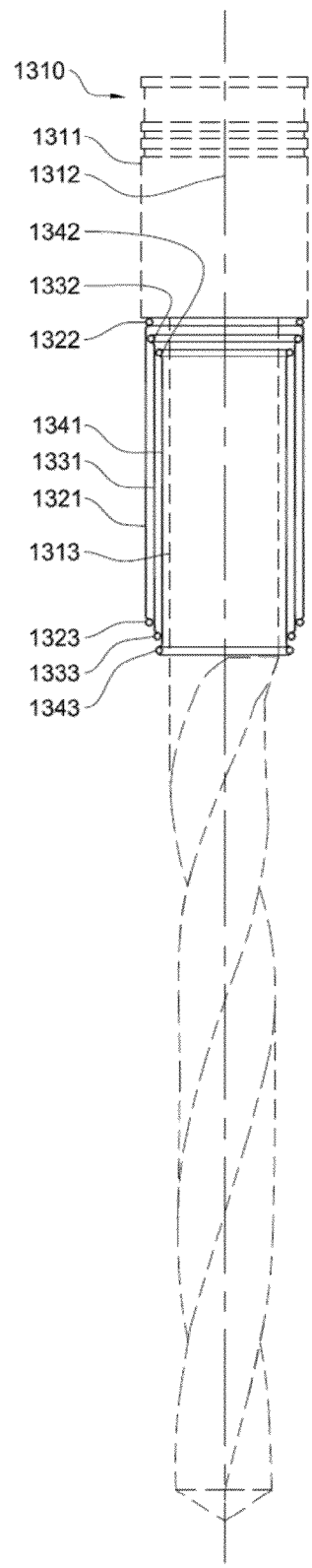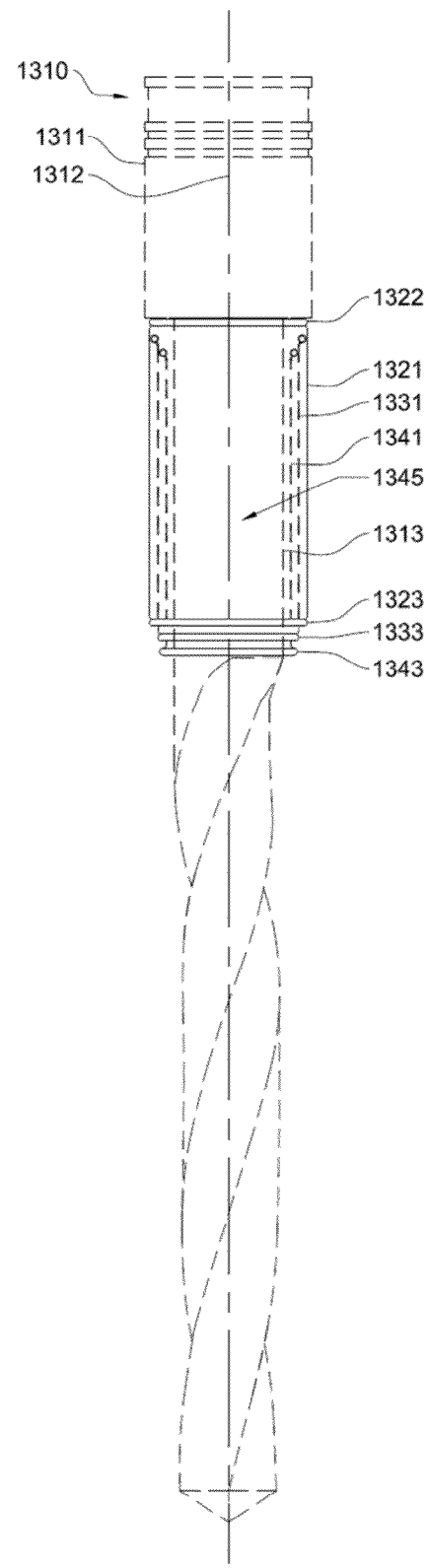
*FIG. 13F*  *FIG. 13G*

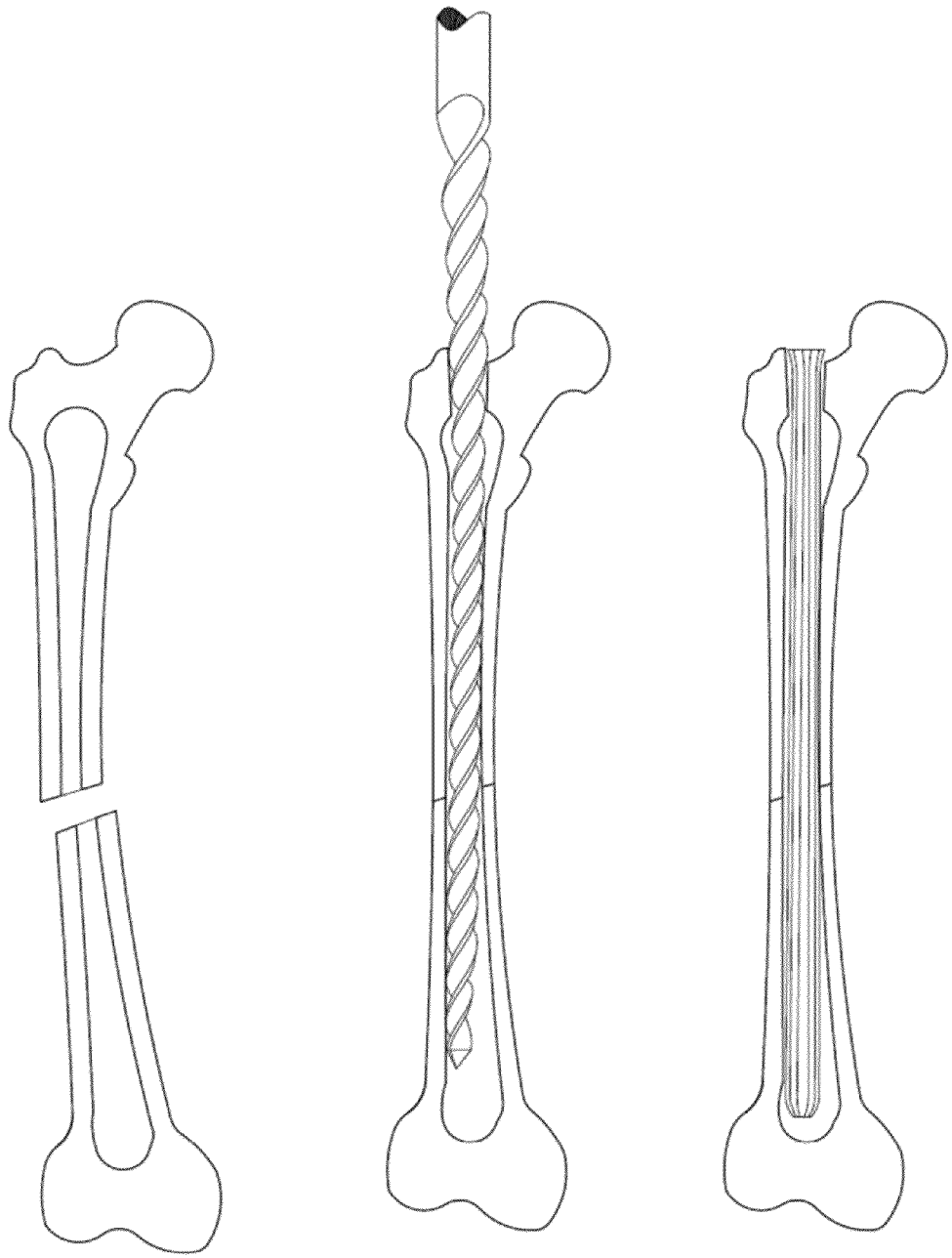
*FIG. 16A*   *FIG. 16B*   *FIG. 16C*

PRECESSIONAL-MOTION BONE AND DENTAL DRILLING TOOLS AND BONE HARVESTING APPARATUS

CROSS-REFERENCE TO RELATED APPLICATIONS

This application claims priority to U.S. Provisional Application No. 61/868,276, filed Aug. 21, 2013, and U.S. Provisional Application No. 61/899,705, filed Nov. 4, 2013. The disclosures of the prior applications are considered part of (and are incorporated by reference in) the disclosure of this application.

BACKGROUND

1. Technical Field

In a first context, this document relates to orthopedic devices and methods for their use. For example, this document relates to novel bone drills for performing osteotomies or for drilling holes in bones. The bone drills have at least some centers of mass that are offset from the drill's axis of rotation. Accordingly, the bone drills may rotate and cut using a precessional pattern of motion. In a second context, this document relates to precessional-motion drilling tools generally. For example, this document relates to drill bits and methods of use for drilling a variety of materials including, but not limited to, metals, ceramics, wood, plasterboard, plastics, stone, composites, synthetics, silicon, and the like. This document also relates to dental drills and methods for their use.

2. Background Information

Osteotomies are routinely performed for surgical access or to divide or reposition a bone for surgical correction. Holes may be drilled in bones for various reasons, such as to accommodate screws, pins, dental implants and various other implantable devices and materials, or to collect a bone sample for biopsy. A common example of the need for an osteotomy is a dental implant procedure 10 as depicted in FIG. 1. In this procedure, the surgeon must create a space of a specific diameter and depth in bone 15 (shown in cross-section) to accommodate an implant 20 of corresponding size within the bone 15 and extending above the gum tissue 18. Frequently, the implant is placed sub-periosteally, and autograft bone is used to supplement and aid healing.

The traditional instruments used to create osteotomies resemble ordinary twist drills. These designs were described as early as Hartshorn (1882), and modified by Hanson (1904), Kallio (1960), Kim, (1980) and others. There have been only a few improvements in this technology since that time. Davis (U.S. Pat. No. 5,190,548, May 1993) described a four-sided hollow drill capable of evacuating bone via the tunneled or hollow portion of the drill. Leppelmeier (U.S. Pat. No. 6,312,432, November 2001) described a bone drill, also similar to a twist drill, with a stabilizing point or tip designed to prevent the bone drill from deviating from the long axis of the osteotomy. Leppelmeier (U.S. Publication No. 2012/0004661, January 2012) also proposed an orthopedic drill with flutes having variable helical angles. Lehenkari (U.S. Pub. No. 2012/20245586, September 2012 and U.S. Pub. No. 2013/0110112, May 2013) proposed the use of super-elastic alloys to craft a drill that was multi-directional.

In addition to the minimal improvements in drill technology, these designs offer little opportunity to collect bone for an autograft, which is often necessary. In these cases, the surgeon may use an autograft from another site or he may elect to use allografts or artificial material. Autologous grafts, however, are preferable because they are inherently biocompatible, osteo-conductive, osteo-inductive, and osteogenic. Harvesting autologous bone from a donor site results in additional time and the attendant risk of complications such as donor site pain and morbidity. Allografts, derived from donor (cadaver) tissues, are only osteo-conductive, and may pose the risk of contamination. Artificial materials such as alloplastic bone cement are a poor choice for grafting since they are potentially antigenic and rarely osteo-conductive. Thus, bone collection from the original operating area is desirable.

Performing osteotomies can be challenging even with optimal illumination, magnification and good assistance. For example, in some cases the surgical site may be obscured by blood and bone chips. Keeping the operative field clear during surgery is beneficial. Thus, constant and controlled irrigation with a physiologic media is generally an integral part of these procedures. It is also advantageous to the mechanics of bone cutting, since the flutes of the drills cut more efficiently when the substrate is cooler and in the absence of bone fragments which can clog and stall the drill. Irrigation not only improves the efficiency of the cutting instrument, it also prevents thermal necrosis of the bone which can later retard or negate the healing process. Controlled irrigation takes on even greater importance if the operator intends to capture the bone fragments for reuse in an autograft.

While the use of irrigation is advantageous, delivery of the irrigant to the surgical site typically requires pressurization of the irrigant that can make recovery of bone fragments for an autograft difficult or impossible. An improved method of scavenging bone fragments will permit irrigation under pressure, and aide the surgeon by keeping the operating area cleaner, more visible and more accessible.

Ideally, bone harvesting should be done while performing the osteotomy and still provide adequate access to the surgical for irrigation, while maintaining a clear operating for the surgery.

Previous designs for bone harvesting, such as those suggested by Meller (U.S. Pat. No. 7,033,359) are complex devices comprising a spring, a spring holder arranged around a shank, which is attached to a fixed collection apparatus. The apparatus requires fixation to the head or arm of the handpiece by a retaining pin. The apparatus is essentially intended for bone harvesting and is not designed to prepare the osteotomy for the implant and harvest bone simultaneously. Because the apparatus is solid and fixed, it would also block the irrigant and cause potential over heating of the bony substrate and the bone particles being harvested.

FIGS. 2A and 2B show a conventional bone drill 200. The bone drill 200 shown includes a shaft 202 with a free end or tip 204 and a shank 206. The shaft 202 defines grooves 208 and 210 that spiral around the shaft 202. The grooves 208 and 210 are also referred to in the instant specification as flutes 208 and 210.

FIG. 2B shows a cross-section 212 (i.e., cross-section A-A) of the bone drill 200. The cross-section 208 shows cross-sectional spaces 214 and 216 of the flutes 208 and 210, respectively. The flutes 208 and 210 are generally the spaces on both sides of a helical structure 218 (or helix) that spirals around the shaft 202. The bottom portion of a flute—seen as a line or curve (e.g., curve 220 of FIG. 2B)—is referred to in the instant specification as a spline. The portion of a spline that comes into contact with a surface being cut during cutting will be referred to in the instant specification as a radial land. Item 222 of FIG. 2B is an example of a radial land. A flute of a bone drill usually includes a sharpened edge configured for cutting. Edge 224 of FIG. 2A is an example of such a cutting edge. Edge 224 can be seen as a point 226 in FIG. 2B.

Generally, an instrument having right handed cutting edges is one that will cut or remove material when rotated clockwise, as viewed from shank to tip. In this specification, a direction of rotation will be specified as viewed from the shank to the tip of the instrument. The cut direction of rotation for a right handed bone drill is clockwise. An instrument having left handed cutting edges is one that will cut or remove material when rotated counter clockwise. The cut direction of rotation, in this case, is counter clockwise. A bone drill includes a working portion or drill body, which is the portion that can cut or remove material. The working portion is typically the portion along the shaft that is between the tip of the instrument and the shank end of the flutes. Portion 228 is the working portion for the bone drill shown in FIG. 1A. The working portion is also referred to in this specification as the cutting portion, working body, or the drill body; and the working length as the cutting length, or working length.

SUMMARY

This document provides orthopedic devices and methods for their use. For example, novel bone drills for preparing an osteotomy are provided. The bone drills have at least some centers of mass that are offset from the drills' axis of rotation. The offset center of mass allows the bone drills to generate precessional motion, or form mechanical waves, and are, therefore, referred to nominally herein as swaggering or precessional bone drills. Swaggering designs create wider cutting envelopes with smaller cross-sectional drill body areas, which renders the bone drills more flexible than non-swaggering designs. The bone drills also display wider clearance angles and improved hauling capacity. In some embodiments, the drilling instruments provided herein are made from stainless steel that may or may not be coated. In alternative embodiments, the drilling instruments provided herein are made from super-elastic alloys such as nickel-titanium alloys (e.g., nitinol) to increase the flexibility of the bone drills. In some embodiments, the bone chips generated by bone drilling are collected in a removable apparatus fixed to the distal portion of the drill, and the collected bone chips can be used for bone grafting.

While the precessional-motion drilling tools provided herein are described below in the context of drilling boney material, it should be understood that the precessional-motion drilling tools can also be beneficially used in the context of a wide variety of other materials. Such materials can include, but are not limited to, metals, ceramics, wood, plasterboard, plastics, stone, composites, silicon, synthetics, and the like. The accompanying drawings and description are included to provide a further understanding of the disclosure in general. A bone drilling implementation is provided as a non-limiting contextual example application for the tools and methods provided herein, so that a general understanding of the design and operation of the precessional-motion drilling tools provided herein can be obtained. One of skill in the art will readily appreciate, from such an understanding, how the precessional-motion drilling tools provided herein are applicable and advantageously useful in the context of drilling other materials in addition to bone material.

In general, one aspect of this document features a bone drill. The bone drill comprises a shank configured to be releasably attachable to a motor to rotate the bone drill about an axis of rotation. The bone drill further comprises a drill body extending from the shank. The drill body includes a shank end where the drill body extends from the shank and a free end at an end of the drill body that is opposite of the shank end. The drill body includes a cutting portion between the shank end and the free end. The drill body has a center of mass at each transverse cross-section of the drill body. The center of mass of a transverse cross-section at the shank end is offset from the axis of rotation and the center of mass of a transverse cross-section at the free end lies on or near the axis of rotation. The distance of the center of mass from the axis of rotation decreases monotonically from the shank end to the free end.

In various implementations of the bone drill, the distance of the center of mass from the axis of rotation may decrease linearly from the shank end to the free end. The center of mass of the transverse cross-section at the free end may lie on the axis of rotation. The centers of mass may form a spiral around the axis of rotation. The drill body may have a substantially constant diameter from the shank end to the free end. The drill body may be tapered from the shank end to the free end. The drill body may be tapered from the free end to the shank end, whereby the maximum flute diameter is at the free end. The drill body may include a transverse cross-section that is asymmetrical, bisymmetrical, symmetrical, triangular or quadrilateral (including trapezoidal or rhomboidal). The tapered body may include a first transverse cross-section and a second transverse cross-section. The first transverse cross-section may have a first geometry, and the second transverse cross-section may have a second geometry different from the first geometry. The tapered body may cut along a dual axis—the dual axis comprising a first axis corresponding the central axis of rotation and a second axis corresponding to an offset mass path which rotates around the central axis.

In various implementations of the bone drill, the bone drill may comprise a chisel tip at the free end of the drill body. The chisel tip may subtends an angle of at least 90 degrees. An end of the chisel tip may be on the axis of rotation. An end of the chisel tip may be offset from the axis of rotation. The chisel tip may include a plurality of inclined planes at substantially equal inclination. The chisel tip may include a first inclined plane and a second included plane with a different inclination than the first inclined plane. A portion of the drill body near the free end may have blunted cutting edges. The bone drill may be comprised of a nickel-titanium alloy.

In various implementations of the bone drill, the cutting portion of the bone drill may be sized to prepare an osteotomy having a diameter within a range of about 1.5 millimeters to about 8.0 millimeters. The bone drill may be sized to prepare an osteotomy having a depth sufficient to receive implants with lengths ranging from about 8 millimeters to about 18 millimeters. The cutting portion may be coated with diamond-like carbon. The cutting portion may be coated with amorphous diamond. The cutting portion may be coated with titanium nitride. The bone drill may have a longitudinal irrigation passage which passes through a collar portion of the bone drill and transverses a core or web of the drill exiting laterally and distally, wherein the passage is configured to allow flow of irrigation fluid to a lateral perimeter and tip of the bone drill. The bone drill may further comprise one or more depth markers or depth gauges on the drill body.

In a second general aspect, this document features a method of cleaning or enlarging an intramedullary space. The method comprises: inserting a bone drill into the intramedullary space; contacting the tip end of the bone drill against an inner surface of the intramedullary space; and rotating the bone drill so that the tapered body bends away from the axis of rotation a substantially equal amount at a first angle of rotation and at a second angle of rotation.

In various implementations of the method, rotating the bone drill may include causing the bone drill to form sinusoidal waves within the intramedullary space. Rotating the bone drill may include causing the bone drill to form helical waves within the intramedullary space. The bone drill may be comprised of a nickel-titanium alloy.

In a third general aspect, this document features another method of cleaning or enlarging an intramedullary space. The method comprises: inserting a bone drill into the intramedullary space; contacting the tip end of the bone drill against an inner surface of the intramedullary space; and rotating the bone drill so that the tapered body cuts along a dual axis, the dual axis comprising a first axis corresponding the axis of rotation and a second axis corresponding to an offset mass path which rotates around the axis of rotation.

In various implementations of the method, rotating the bone drill may include causing the bone drill to form sinusoidal waves within the intramedullary space. Rotating the bone drill may include causing the bone drill to form helical waves within the intramedullary space. The bone drill may be comprised of a nickel-titanium alloy.

In a fourth general aspect, this document features an apparatus for harvesting bone matter. The apparatus comprises: a first canister, the first canister comprising an open cylinder with an inner diameter and an outer diameter, the open cylinder of the first canister including a proximal end and a distal end, the proximal end being configured to couple with a bone drill; and a second canister, the second canister comprising an open cylinder with an inner diameter and an outer diameter, the open cylinder of the second canister including a proximal end and a distal end. The first canister and the second canister are configured to slidably engage with each other such that, in a retracted configuration, a majority of one of the canisters is positioned substantially within an interior region defined by the other canister, and, in an extended configuration, a majority of each of the canisters is positioned outside of the interior region defined by the other canister.

In various implementations of the apparatus, the second canister may be configured to be movable in an axial direction in relation to a bone drill to which the apparatus is coupled, and the first canister may be configured to be fixed from being moved in the axial direction in relation to the bone drill. The inner diameter of the second canister may be larger than the outer diameter of the first canister, such that the second canister can slide in relation to the first canister between the retracted configuration in which a majority of the first canister is within an interior region defined by the second canister and the extended configuration. The first canister may be rotatably coupleable with a bone drill. The first and second canisters may be configured to not rotate while a bone drill to which the apparatus is coupled does rotate. An interior region defined by the first canister may be configured to receive bone chips that are generated by a drilling process using a bone drill to which the apparatus is coupled. The first and second canisters may be configured to slide in relation to each other when the canisters are coupled to a bone drill and when the bone drill is advanced into a bone such that the second canister makes contact with the bone. The inner diameter of the first canister may be larger than the outer diameter of the second canister, such that the first canister can slide in relation to the second canister between the retracted configuration in which a majority of the second canister is within an interior region defined by the first canister and the extended configuration.

The bone harvesting apparatus may further comprise a third canister. The third canister may comprise an open cylinder with an inner diameter and an outer diameter. The open cylinder of the third canister may include a proximal end and a distal end. The third canister may be configured to slidably engage with the second canister such that, in the retracted configuration, a majority of two of the canisters is positioned substantially within an interior region defined by the other canister, and such that in the extended configuration, a majority of each of the three canisters is positioned outside of the interior region defined by the two other canisters.

In a fifth general aspect, this document features another bone drill. The bone drill comprises a shank that is configured to be releasably attachable to a motor to rotate the bone drill about an axis of rotation, and a drill body extending from the shank. The drill body includes a shank end where the drill body extends from the shank and a free end at an end of the drill body that is opposite of the shank end. The drill body includes a cutting portion between the shank end and the free end. The drill body has a center of mass at each transverse cross-section of the drill body. A center of mass of a transverse cross-section at the shank end is offset from the axis of rotation and a center of mass of a transverse cross-section at the free end is offset from the axis of rotation. A distance from a center of mass of each transverse cross-section between the shank end and the free end is offset from the axis of rotation by a substantially consistent distance.

In various implementations of the bone drill, the centers of mass of consecutive transverse cross-sections between the shank end and the free end form a mass path. In some embodiments, the mass path comprises a helix. In some embodiments, at least a portion of the mass path is linear. The drill body may have a substantially constant diameter from the shank end to the free end, or may be tapered from the shank end to the free end such that the shank end has a larger cutting diameter than the free end, or may be tapered from the free end to the shank end such that the free end has a larger cutting diameter than the shank end. In some embodiments, the tapered body includes a first transverse cross-section and a second transverse cross-section, wherein the first transverse cross-section has a first geometry; and wherein the second transverse cross-section has a second geometry different from the first geometry. In particular embodiments, the tapered body may cut along a dual axis, the dual axis comprising a first axis corresponding the central axis of rotation and a second axis corresponding to an offset mass path which rotates around the central axis. The drill body may include a transverse cross-section that is asymmetrical, bisymmetrical, symmetrical, triangular, or quadrilateral shaped (including trapezoid, parallelogram, and rhombus shapes).

In a sixth general aspect, this document provides bone drill. The bone drill comprises a shank configured to be releasably attachable to a motor to rotate the bone drill about an axis of rotation and a drill body extending from the shank. The drill body includes a shank end where the drill body extends from the shank and a free end at an end of the drill body that is opposite of the shank end. The drill body includes a cutting portion between the shank end and the free end. The drill body has a center of mass at each transverse cross-section of the drill body. A center of mass of a transverse cross-section at the shank end is offset from the axis of rotation and a center of mass of a transverse cross-section at the free end is offset from the axis of rotation.

In various implementations of the bone drill, the centers of mass of consecutive transverse cross-sections between the shank end and the free end form a mass path, and the mass path may comprise a spiral. In some implementations, at least a portion of the mass path is substantially linear. In some implementations, at least a portion of the mass path is curved, and a center of mass of one and only one transverse cross-section is on the center of rotation, or a center of mass of two and only two transverse cross-sections are on the center of rotation. In some implementations, all centers of mass of each transverse cross-section may be in a common plane. In some implementations, the centers of mass of consecutive transverse cross-sections between the shank end and the free end form a mass path, and a first portion of the mass path is offset from the axis of rotation by a substantially constant distance, while a second portion of the mass path is offset from the axis of rotation by a distance that decreases monotonically.

Particular embodiments of the subject matter described in this document can be implemented to realize one or more of the following advantages. In some embodiments, the orthopedic drilling instruments described herein can provide more efficient osteotomy procedures, and osteotomy procedures which are safer for a patient. An instrument that is both flexible and strong resists breaking and injuring the patient. An instrument that is flexible and has a center of mass offset from an axis of rotation may swing out from the axis of rotation as the instrument is rotated at high speeds, such as when the instrument is used with a motorized actuator tool. If the instrument is configured to bend an equal amount at each angle of rotation, the inner diameter of a space can be contacted by the instrument and uniformly cleaned. The instrument can be made to have a smaller diameter than the space that requires cleaning, thereby allowing for a difficult to access area to be accessed. Other advantages offered by the swaggering or precessional drill designs include the intermittent contact of the flutes of the drill with the bone itself. If the intra-osseous space can be enlarged more efficiently, the bony substrate is kept cooler to avoid or reduce the occurrence of thermal bone necrosis that can retard or negate the healing process. Intermittent contact can also facilitate irrigation, which can also improve the cutting efficiency of the instrument. Additionally, bony fragments can clog and stall the drill. Efficient removal of the fragments improves cutting, visibility and offers an opportunity to capture these bony fragments for reuse in an autograft.

Within the context of the above objectives, new bone harvesting devices are also disclosed in this document. The bone harvesting devices disclosed herein are convenient to manufacture and adaptable to work with the bone drills disclosed herein, as well as with other embodiments of drills and drill-like instruments. The bone harvesting devices can be reusable in some embodiments, and the bone harvesting devices can be disposable in some embodiments. The bone harvesting devices disclosed herein are also designed to readily fit a guide for the osteotomy and facilitate maximum irrigation, while collecting bone efficiently.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 3A-3E depicts various views of an example two-sided rotary offset bone drill.

FIGS. 4A-C and 4F depict a two-sided rotary offset bone drill with a web that can be used as a pilot drill, may perform an osteotomy in preparation for a dental implant, and may also be useful in a variety of other orthopedic applications. This two-sided rotary offset bone drill embodiment cuts a tapered cutting envelope.

FIGS. 5A-5C and 5F show an example three-sided rotary offset bone drill. This instrument may be used, for example, as a pilot drill, to sequester bone, or to prepare the osteotomy for implant placement. In some embodiments, this style of instrument cuts within a tapered cutting envelope.

FIG. 6G shows the differential of the cutting envelope of the bone drills of FIGS. 5A-5F (a tapered cutting envelope) in comparison to the cutting envelope of the bone drills of 6A-6F (a parallel cutting envelope).

FIGS. 7A1 and 7B1 show the active tip of example pilot drills that will remain substantially centered when in use.

FIGS. 7A-7C and 7F show views of an example three-sided rotary offset bone drill that is slightly wider at the tip than at the shank end. In this embodiment, the centers of mass of all transverse cross-sections along the working length are offset from the axis of rotation, while the point of the tip coincides with the axis of rotation. This instrument can be used, for example, to prepare an osteotomy for implant placement, or for bone sequestration. In some embodiments, this style of instrument is designed to cut a parallel cutting envelope.

FIGS. 9A1-9C1, 9A2-9C2, and 9F show views of an example four-sided rotary offset bone drill that is slightly wider at the tip than at the shank end and that has a transverse cross-section in the form of a parallelogram. In this embodiment, the center of mass at the shank is offset from the center of rotation, and the center of mass at the tip coincides with the axis of rotation. This instrument can be used, for example, to prepare an osteotomy for implant placement, or for bone sequestration. In some embodiments, this style of instrument is designed to cut a parallel cutting envelope.

FIGS. 9D1 and 9E1 are transverse cross-sectional views of the four-sided rotary offset bone drill of FIGS. 9A1-9C1 and 9A2-9C2.

FIGS. 10A-10I show an example bone collection apparatus for use with the bone drill instruments provided herein. This embodiment demonstrates two telescopic canisters with the largest canister located proximally.

FIGS. 11A-1H show example drill blanks from which the drilling instruments provided herein can be manufactured.

FIGS. 12A-12G show another example of a bone harvesting apparatus for use with the bone drill instruments provided herein. This embodiment demonstrates three telescopic canisters with the largest canister located distally, and an unperforated upper canister.

FIGS. 13A-13G show another example bone collection apparatus for use with the bone drill instruments provided herein. This embodiment demonstrates three telescopic canisters with the largest canister located proximally and an unperforated upper canister.

FIG. 16A depicts a fractured long bone.

FIG. 16B depicts an offset intramedullary drill preparing the intramedullary space for in preparation for an intramedullary pin.

FIG. 16C depicts placement of an intramedullary pin and the fixation of the long bone in preparation for healing.

Like reference numbers represent corresponding parts throughout.

DETAILED DESCRIPTION

In a first context, this document provides orthopedic devices and methods for their use. For example, novel bone drills for preparing an osteotomy are provided. The drilling instruments provided herein have at least some cross-sections (perpendicular to the axis of rotation) with centers of mass that are offset from the drills' axis of rotation. The offset center of mass may allow the drills to generate precessional motion or form mechanical waves when in use. In a second context, this document provides precessional-motion drilling tools for industrial use. For example, this document provides drill bits and methods of use for drilling a variety of materials including, but not limited to, metals, ceramics, wood, plasterboard, plastics, stone, composites, synthetics, silicon, and the like.

A great deal of mathematics and engineering has been dedicated to modeling, studying and solving the problems associated with high frequency and low frequency vibrations during drilling in attempt to improve drilling efficiency. These include the work of Yang and Jaganathan (2002), Stone and Askari (2002), Hsieh (2005) and Gupta, Ozdoganlar, Kapoor, and DeVor (2003). Using the simplest model practical, Kessentini et al. used a two-degrees of freedom model to simulate the vibration of twist drills in an x and y direction. The z-axis was the longitudinal axis of rotation. The model was used to describe the relative tool position in time (t). The algorithm:

$$r(t)=\sqrt{x^2(t)+y^2(t)}$$

was used to calculate the radial vibration of the drill deduced directly about x(t) and y(t). This equation is related to the Perpendicular-Axis Theorem, which correlates the inertia of a thin lamina of an object (e.g., cylindrical drill body) with coordinates x and y. If inertia (I) is defined as $I=mr^2$, then the total inertia of the lamina rotating around the z-axis can be described as $Iz=Ix+Iy$.

When working in Cartesian coordinates the moment of inertia for a planar body is:

$$I_x=\int(x^2+y^2)dm=\int x^2 dm+\int y^2 dm=I_y+I_x$$

Although mathematical algorithms are useful in modeling, a more simplistic approach in understanding the value of precessional cutting and offset designs is the evaluation of the moment of inertia of a cylinder of radius r and its associated radius of gyration $R_g$ making the explanation of changes in inertia become more understandable.

Figure 2A:
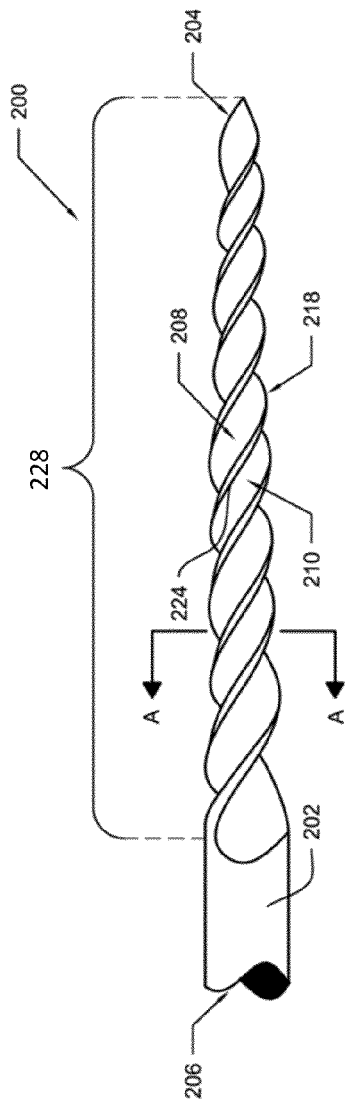
FIGS. 2A and 2B depict an ordinary twist drill.
Figure 2B:
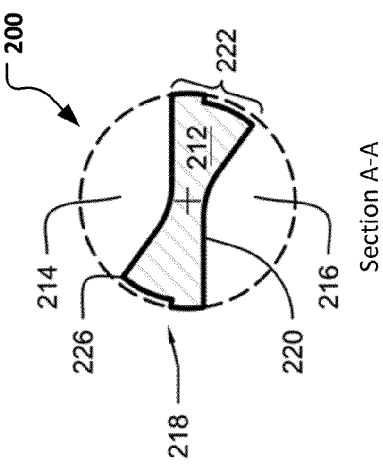
Figure 2D:
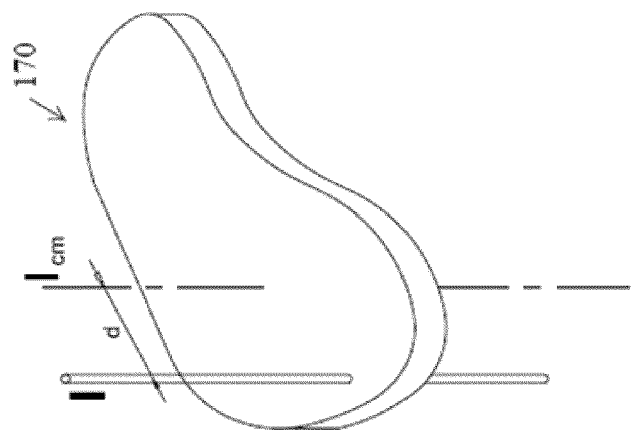
FIG. 2D depicts a thin lamina of an offset drill body that is rotating around the axis of rotation.
Figure 2C:
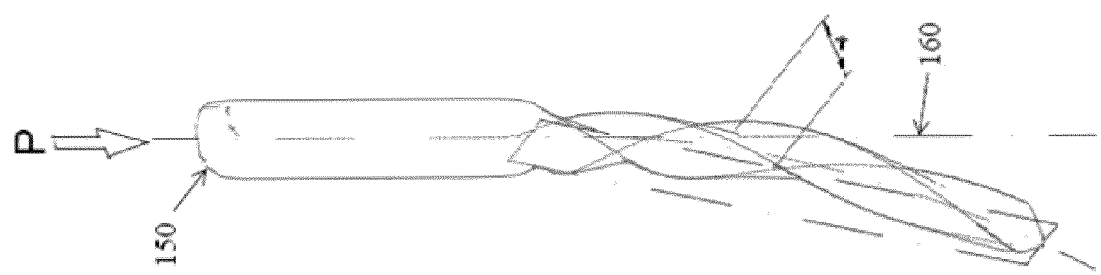
FIG. 2C depicts a drill body that is bending or buckling via axial (compressive) force.

The radius of gyration $R_g$ is a convenient parameter, providing a measure of the resistance of a cross-section to lateral buckling as shown by the displacement x in FIG. 2C, or an indication of the stiffness of a section based on the shape of the cross-section when used under pressure or compression P (for example a cylindrical drill body).

In general, the member will bend in the thinnest plane and in an area of least support and is expressed by the formula:

$$R_g = \sqrt{\frac{I}{A}}$$

Where I=moment of area, and A=area of material in the cross-section.

Thus, the radius or gyration, and thereby the resistance to buckling and/or distortion, increases as the moment of inertia from a given mass in a given coordinate system increases. The moment of inertia can be calculated for any rigid body that is undergoing a physical rotation around a fixed axis. It is based not only on the physical shape of the object and its distribution of mass, but also the specific configuration of how the object is rotating. So the same object rotating in different ways would have a different moment of inertia in each situation. The general formula:

$$I_P = \sum_{i=1}^{N} m_i r_i^2,$$

represents the most basic concept for the moment of inertia. Basically, for any rotating object, the moment of inertia can be calculated by taking distance of each particle from the axis of rotation (r in the equation), squaring that value (the $r^2$ term), and multiplying it times the mass of that particle. That is done for all of the particles that make up the rotating object, and combining the results gives the moment of inertia.

The consequence of this formula is that the same object gets a different moment of inertia value, depending on how it is rotating and where it is located in space. A new axis of rotation and/or a new centroid ends up with a different formula, even if the physical shape of the object remains the same. Thus, the further the x and y coordinates for r move away from the axis of rotation and/or the centroid the larger the value of rotational inertia I.

In the case of a solid cylinder, the expression for the moment of inertia can be extrapolated by viewing thin lamina and is expressed as:

$$I = \int_0^M r^2 dm$$

where M is the mass and dm is the mass differential. Again, from the equations above it becomes clear that the moment of inertia increases as the radius of the centroid increases.

The Parallel-Axis theorem, also known as the Huygens-Steiner theorem, which was employed in the 17th century to describe planetary motion, is especially useful for evaluating the improvement in inertia using offset centers of mass. A lamina of an offset cylindrical drill body is shown in FIG. 2D. One can write the formula for the parallel-axis theorem in its simplest form as $I=Icm+md^2$. Here km is the moment of inertia of a body of mass m with respect to a line through its centroid cm, I is the total moment of inertia with respect to a line parallel to the central axis or axis of rotation, and d is the distance between the two lines. Thus, for a given lamina, total inertia I (and the resistance to bending and distortion) can be improved by improvements in both the mass of a cross-section and an exponential increase in the distance from the central axis to the centroid.

Thus, improvements in torsional inertia (and resistance to bending) can be accomplished by a modest offset of the cross-section area away from the central axis without substantially increasing the mass or (in the case of a twist drill) the thickness of the core or web.

In some embodiments, the drills and/or reamers described herein have one or more cross-sections with a centroid (center of mass) that is offset from the drill's axis of rotation. The offset center of mass allows these drills and/or reamers to generate precessional motion, and/or to form mechanical waves during rotation. The hallmark of precessional cutting devices is the intermittent contact of the cutting edges of the flutes with the walls of the substrate as it is being cut or perforated, which has the potential of reducing or eliminating chatter both in an axial and torsional direction. Unlike previous drill designs the drills and/or reamers provided herein accomplish the same functions as orbital drills, but can be used in a standard rotary drill or spindle.

Precessional drills and/or reamers can create cutting envelopes with cross-sectional areas that are larger than at least some of the cross-sectional areas of the drill or reamer itself, and are therefore lighter and require less energy to operate. They also possess wider clearance angles with improved hauling capacity, which further improves cutting efficiency.

Other advantages offered by precessional drills and/or reamers are the intermittent contact of the flutes of the device with the substrate rendering the work piece cooler and less susceptible to distortion. Intermittent contact can also facilitate higher volumes of irrigant or coolant when temperature control is mandatory, for example during perforation of ceramics, glass and silicon, also improving the cutting efficiency. Further, the drills and/or reamers described herein, when fabricated from a flexible or super-flexible alloy, can engender bodily movement or deflection, which can be particularly useful in drilling and/or reaming irregular spaces or spaces with some degree of curvature.

In this document, the term "offset" refers to a configuration of a cutting instrument (e.g., a drill, reamer, and the like) wherein the centroid of one or more transverse cross-sections of the cutting instrument are spaced apart from the axis of rotation of the cutting instrument. The combination of multiple centroids of consecutive transverse cross-sections of a cutting instrument define a "center of mass path" of the cutting instrument. As will be described further below, the center of mass path of the cutting instruments provided herein can be partially or fully offset from the axis of rotation of the cutting instruments. Additionally, offset center of mass paths, or portions thereof, can have various configurations. For example, some offset center of mass paths, or portions thereof, are linear. Some offset center of mass paths, or portions thereof, are curved (e.g., a single curve, or multiple curves such as an S-shape or sine wave). Some offset center of mass paths, or portions thereof, are helical or a cork-screw shape. It should be understood that combinations of such center of mass paths can be combined in a single cutting instrument. For example, a single cutting instrument can have one or more portions that have a center of mass path that are coincident with the axis of rotation, and one or more other portions that have a center of mass paths that are offset. Further, such one or more other portions that have a center of mass paths that are offset can have similar or dissimilar configurations. For example, a first offset center of mass path portion can be linear, while a second offset center of mass path can be curved, helical, cork-screw shaped, and the like. It should be understood that any such combinations and permutations of center-off-mass-paths are envisioned and within the scope of this disclosure.

In addition, it should be understood that the cutting instruments provided herein may be fully or may have portions that have a cylindrical profile, a tapered profile, a multi-tapered profile, and the like, and any combination and subcombination thereof. For example, some embodiments provided herein have a multi-tapered profile which means that a first portion of the cutting instrument has a diametrical taper at a first taper rate, and the cutting instrument has one or more other portions that have a diametrical taper at a rate that is different than the first taper rate. It should be understood that cutting instruments having any combination and permutation of portions with a tapered profile, a multi-tapered profile, and the like are envisioned and within the scope of this disclosure. For example, a single cutting instrument may have a first portion that has a cylindrical profile, a second portion that has a multi-tapered profile, and one or more additional portions that have a cylindrical or other shaped profile.

Figure 1:
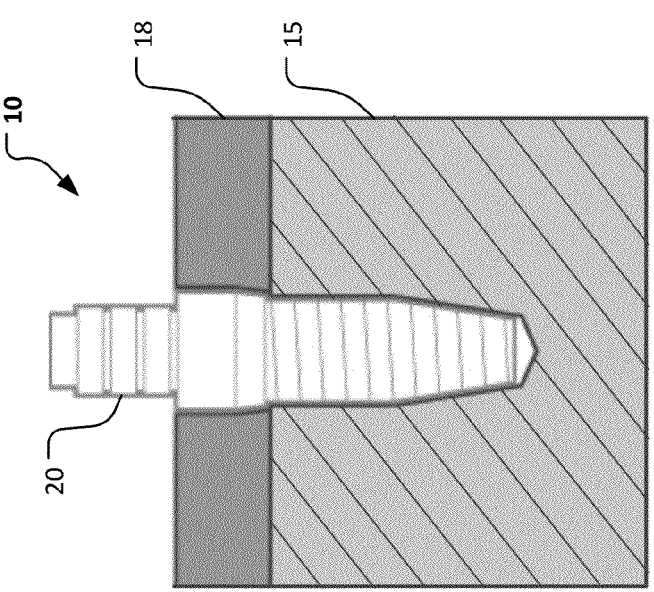
FIG. 1 depicts an example dental implant.

FIG. 1 depicts a dental implant 20 that is placed in the mandible or maxilla 15 following an osteotomy, which is performed using a bone drill of various embodiments described herein.

FIGS. 2A and 2B provide an example of a standard twist drill 200 as described further in the Background section above.

FIGS. 3A-6E illustrate various implementations of the bone drill. A common feature of these implementations is that the centers of mass of the cross-sections are further from the axis of rotation at the shank end of the working portion than at the free end or tip end of the working portion. The offset of the center of mass from the axis of rotation can decrease monotonically, e.g., linearly, from the shank end to the tip end. Since the cross-sectional shape of the working portion rotates from the shank end to the tip end, the centers of mass of the cross-sections form a spiral path of decreasing diameter (from shank to tip) around the axis of rotation. Although the implementations of FIGS. 3A-6E are illustrated with the center of mass at the tip end of the working portion located on the axis of rotation, this is not necessary; the center of mass at the tip end of the working portion can remain slightly offset from the axis of rotation (although not as much as the shank end).

The diameter of the working portion can be substantially constant from the shank to the tip end, or can narrow slightly, e.g., at angle of less than 10 degrees, less than 5 degrees, or less than 1 degree, from the axis of rotation.

After the working portion of the drill, the drill narrows suddenly to form an angled tip. For example, in some embodiments the tip can have a point angle of about 60 to 75 degrees, 75 to 90 degrees, 90 to 105 degrees, 105 to 120 degrees, 120 to 135 degrees, about 135 to 150 degrees, or greater than 150 degrees.

FIGS. 3A-3E illustrate an example two-sided rotary offset bone drill 310 The bone drill 310 is described as an "offset" bone drill because the centers of mass of the cross-sections (e.g., centers of mass 330a and 330b of FIGS. 3C and 3D respectively) along the working portion 312 are offset from the axis of rotation 305 of the bone drill 310. As shown in cross-sectional view 3C, the offset begins at the shank 311, and migrates from the shank 311 to the tip 320, until the center of mass becomes completely centered on the axis of rotation 305 at the tip end 320 of the instrument 310.

This drill 310 features a narrow web 335 for bone sequestration or harvesting. The drill 310 defines two flutes 320A and 320B that, relative to the center of mass, are substantially bisymmetrical in transverse cross-section, and that can be utilized to remove bone. A fitting, which is suitable for releasably coupling to an engine driven motor actuator with a hand-piece and chuck, or a handle utilized for manual actuation, can be fixedly attached to the shank 311 The bone drill instrument 310 is well-suited, for example, for use as a pilot drill, to perform an osteotomy in preparation for a dental implant, and for use in a variety of other orthopedic applications. The bone drill 310 cuts a tapered cutting envelope because of the offset centers of mass.

FIGS. 4A-4F illustrate another example embodiment of the bone drills provided herein. The bone drill instrument 410 depicted includes a shank 411, a free end or tip 413, and a working portion 412 therebetween. In some embodiments, the diameter of the working portion 412 is slightly tapered, that is, decreasing in diameter from the shank 411 to the tip 413. In other embodiments, the diameter of the working portion 412 is consistent along the working portion 412.

The drill 410 defines two flutes 420A and 420C that are relatively bisymmetrical in transverse cross-section, and that can be utilized to remove bone. As will be described further, the bone drill 410 cuts a bone cavity or prepares an osteotomy that is tapered.

A fitting 415, which is suitable for releasably coupling to an engine driven motor actuator with a hand-piece and chuck, or a handle utilized for manual actuation, can be fixedly attached to the shank 411.

The tip 413 can include an active or cutting surface that is confluent with the working portion 412 (for example, like the tips shown in FIGS. 7A1 and 7B1). Alternatively, the leading tip 413 can include a non-active or non-cutting surface that is confluent with the working portion 412 (for example, like the tip shown in FIGS. 14A and 14B).

Figure 4E:
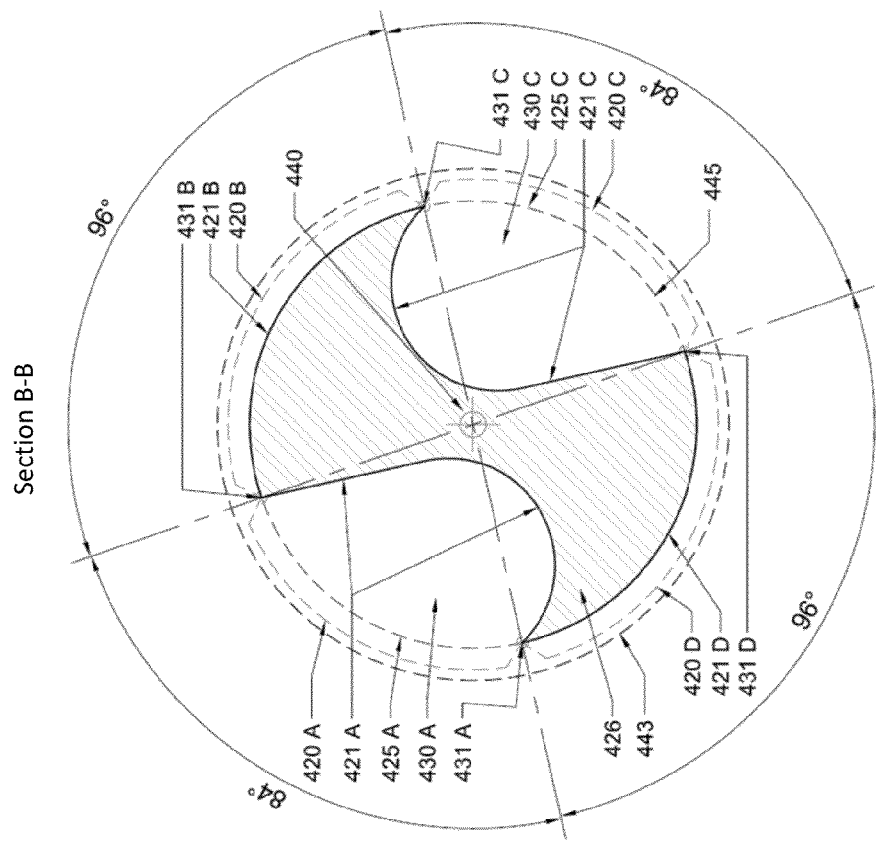
FIGS. 4D and 4E are transverse cross-sectional views of FIG. 4A taken at sections A-A and B-B respectively.
Figure 4D:
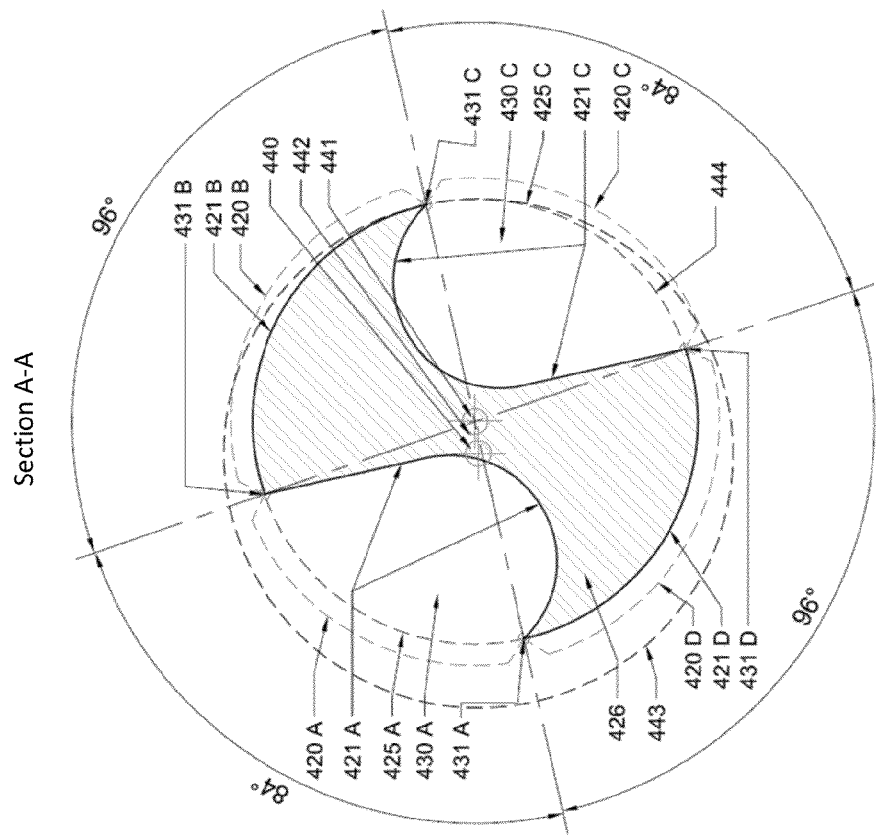
Figure 4F:
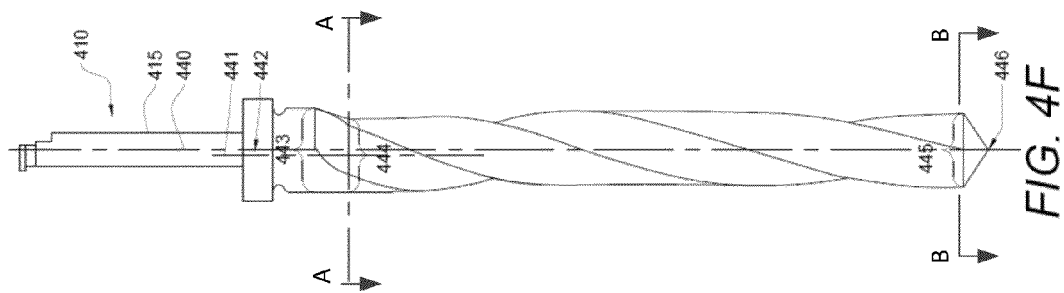
Figure 4G:
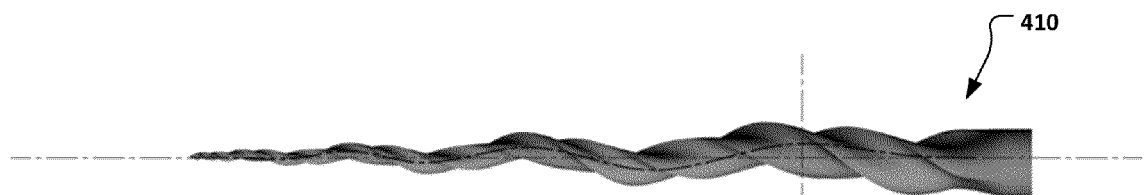
FIG. 4G shows an elongate view of an example bone drill that has a working portion with centers of mass that are offset from the axis of rotation along the working portion to the tip that is centered on the axis of rotation.

The MxFD (maximum flute diameter) 417 of the bone drill 410 is located near the shank 411 end of the working portion 412. The MnFD (minimum flute diameter) 418 is located near the tip 413. The shank 411 above the working portion 412 is essentially cylindrical and has a slightly larger diameter than the cutting surface at the MxFD 417. With reference in particular to FIGS. 4D-4F, those skilled in the art will recognize that the center of mass of a cross-section at the MxFD 417 is offset from the axis of rotation 440 of the bone drill 410. However, the center of mass of a cross-section at the MnFD 418 lies on or coincides with the axis of rotation 440.

As shown in FIGS. 4A-4F, the bone drill 410 defines two continuous helical flutes 420A and 420C. The flutes 420A and 420C are substantially concave grooves following the circumference of the working portion 412 as spirals between the shank 411 and the leading tip 413 to define concentric circles. The flutes 420A and 420C occur alternately with lands 420B and 420D. In some embodiments, the flutes 420A and 420C have a uniform pitch along the longitudinal axis. In other embodiments the flutes 420A and 420C may become increasingly tighter or more numerous as they approach the tip 413. The total number of turns per flute of the flutes 420A and 420C between the MxFD 417 and the MnFD 416 can depend on the total length of the working portion 412, but is not less than one-quarter of one complete revolution. Helical flutes 420A and 420C each originate at the MxFD 417 at separate locations that are equally spaced apart around the circumference of the shank 411, or more specifically at 180 degrees of separation for two flutes.

As best seen in FIGS. 4D and 4E, the flutes 420A and 420C are defined by J-shaped splines 421A and 421C. The J-shaped splines 421A and 421C intersect with the lands 420B and 420D to form helical cutting edges 425A and 425C extending from the periphery of the shank 411 to the tip 413. The J-shaped splines 421A, 421C and the lands 420B, 420D comprise the surfaces of a web or core 426 of the drill 410. The areas of radial clearance, or cut-outs, of the flutes 421A and 421C outline a portion of the web or core 426. These areas of clearance are designated by numerals 430A and 430C. In transverse cross-section from the shank 411 to the tip 413, the splines 421A and 421C of cutting flutes 420A and 420C form teardrop shaped clearance areas of variable depth. The cutting surfaces 425A and 425C and the splines of the inner walls 421A and 421C circumscribe clearance areas 430A and 430C.

With further reference to FIGS. 4D and 4E, it can be seen that the generally J-shaped splines 421A and 421C intersect the periphery of the shank 411 at points 431A and 431C. These intersections are equal distances apart, or at 180° of separation forming a neutral cutting angle (or a 90° angle to the tangent of the perimeter of shank 411). It is recognized that this cutting angle may be either negative or positive (that is, less than or greater than 90° to the tangent of the perimeter of the shank 411). It is envisioned that to create various embodiments of the bone drills provided herein, splines 421A and 421C may be varied in depth and shape, and may have any of a myriad of different configurations. For example, while the splines 421A and 421C are J-shaped, in some embodiments the splines 421A and 421C are S-shaped splines (e.g., as shown in the embodiment of FIG. 5A), and may be individually symmetrical or asymmetrical, and may be mirror images of each other. While the depth and shape of each spline 421A and 421C can vary, the cross-sectional diameter of the core portion 426 is generally not narrower than about 20% percent of the diameter of the shank 411.

As stated above, the bone drill 410 is an example two-sided rotary offset bone drill embodiment. In regard to the offset feature, and further referencing FIGS. 4D-4F, the drill 410 has a center-line or axis of rotation 440 (about which the drill 410 rotates when in use), and a mass axis 441 which does not completely coincide with the axis of rotation 440. The mass axis 441 is a line defined by the centers of mass of cross-sectional areas of the bone drill 410. The offset is the difference between the mass axis 441 and the axis of rotation 440 (which are displaced a distance 442 away from each other). The offset distance 442 decreases continuously from the shank 411 to the tip 413, and is zero at the end-point 446. This unique offset feature allows the instrument 410 to cut using a precessional motion. Accordingly, the bone drill 410 cuts a bone cavity or prepares an osteotomy that is tapered.

Figure 4H:
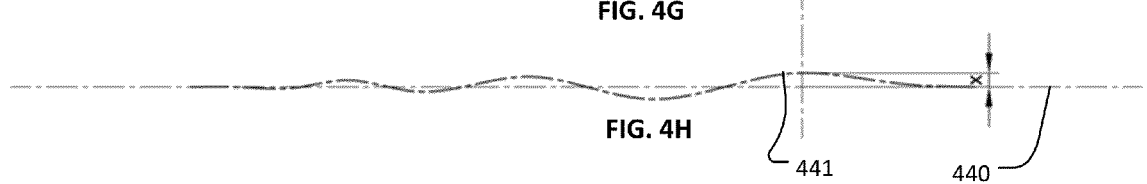
FIG. 4H represents the centers of mass of the bone drill of FIG. 4G.

FIGS. 4G-4K illustrate the characteristic of the bone drill 410 to cut using precessional motion. As previously mentioned, precession describes the motion which occurs whenever the axis about which a body is spinning is, itself, rotating about another axis. As shown in FIG. 4H, the theoretical axis of rotation 440 and the mass axis 441 are offset from each other. The amount of offset between the axis of rotation 440 and the mass axis 441 is defined by the distance between these two axes, and the offset distance varies along the length of the drill. Due to having centers of mass that are offset from the axis of rotation 440, the drill 410 exhibits a phenomenon during rotation that is known as precession or, in the vernacular, swagger. In the case of offset drills, the axis of precession is substantially "inherent" or ground into design and not controlled by external variables. By building the axis of precession into the offset drill, the precessional angle, and therefore the cutting action, can be precisely controlled.

With adequate angular velocity and a sufficient offset center of mass, an offset drill can experience angular accelerations, which can in turn produce radial bodily movements of the drill. This occurs because the vector of centrifugal force F=ma (or force equals mass times acceleration) displaces the centroids of the drill radially to an extent that is limited by the spring constant for the drill as defined by Hooke's law F=−kx (where k is the spring constant and x is the unit length of deflection). In any event, cutting along a precessional axis is accomplished by offsetting the centroid or center of mass of the geometric cross-sectional area over a unit length of the drill 410 and away from the axis or center of rotation 440 of the drill 410. Application of simple wave theory may also be useful in understanding the precessional motion of the bone drills provided herein.

With further reference to elongate drill 410, and as a further description of the properties of the drill 410, the arcuate cutting path can be associated with a wave of amplitude x (refer to FIG. 4H). Thus, the total distance traveled by any point on the arc equals 2x, which defines the cut diameter for that point.

Figure 4I:
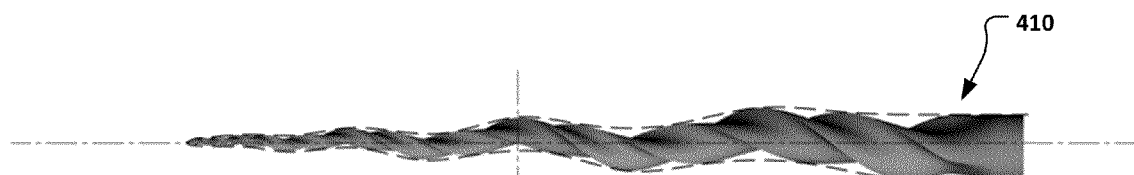
FIGS. 4I-4K depict the cutting envelope of the bone drill of FIG. 4G that cuts with a precessional motion.
Figure 4J:
Figure 4K:
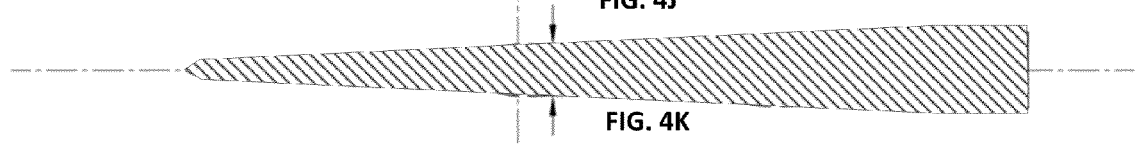

With continued reference to FIGS. 4I-4K, it can also be envisioned that cutting occurs alternately and that no two cutting angles engage the bony walls immediately opposite each other at any one time. This feature allows the instrument 410 to create large cutting envelopes while using a drill 410 with a smaller cross-sectional areas. Those skilled in the art will appreciate that this property improves drill flexibility, reduces cyclic fatigue, mitigates binding or taper lock (the screwing effect), and mitigates transportation away from the intended cut axis or the original anatomy of the space in the case of reaming.

FIGS. 5A-5F illustrate another example bone drill 510. The bone drill 510 is an example of a three-sided rotary offset bone drill embodiment. The offset bone drill 510 has three sides, is generally triangular in transverse cross-section, and can be utilized to remove bone. The bone drill instrument 510 includes a shank 511, a free end or tip 513, and a working portion 512 therebetween. The diameter of the working portion 512 is slightly tapered, that is, decreasing in diameter from the shank 511 to the tip 513. Alternatively, the diameter of the working portion 512 can remain substantially constant along the length of the working portion 512. The working portion 512 of the drill 510 defines three flutes 520A, 520B, and 520C. As will be described further, the bone drill 510 cuts a bone cavity or prepares an osteotomy that is tapered.

A fitting 515, which is suitable for releasably coupling to an engine driven motor with a hand-piece and chuck, or a handle utilized for manual instrumentation, can be attached to the shank 511.

The tip 513 can include an active or cutting surface that is confluent the working portion 512. Alternatively, the leading tip 513 can include a non-active or non-cutting surface that is confluent with the working portion 512 (for example, like the tip shown in FIGS. 14A and 14B).

Figure 5F:
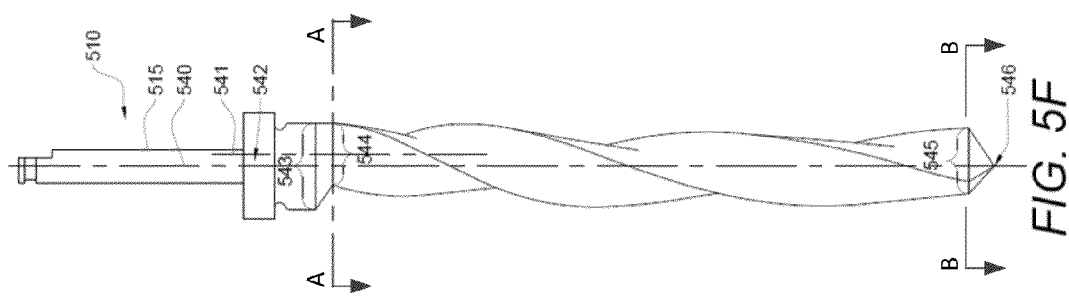
Figure 5E:
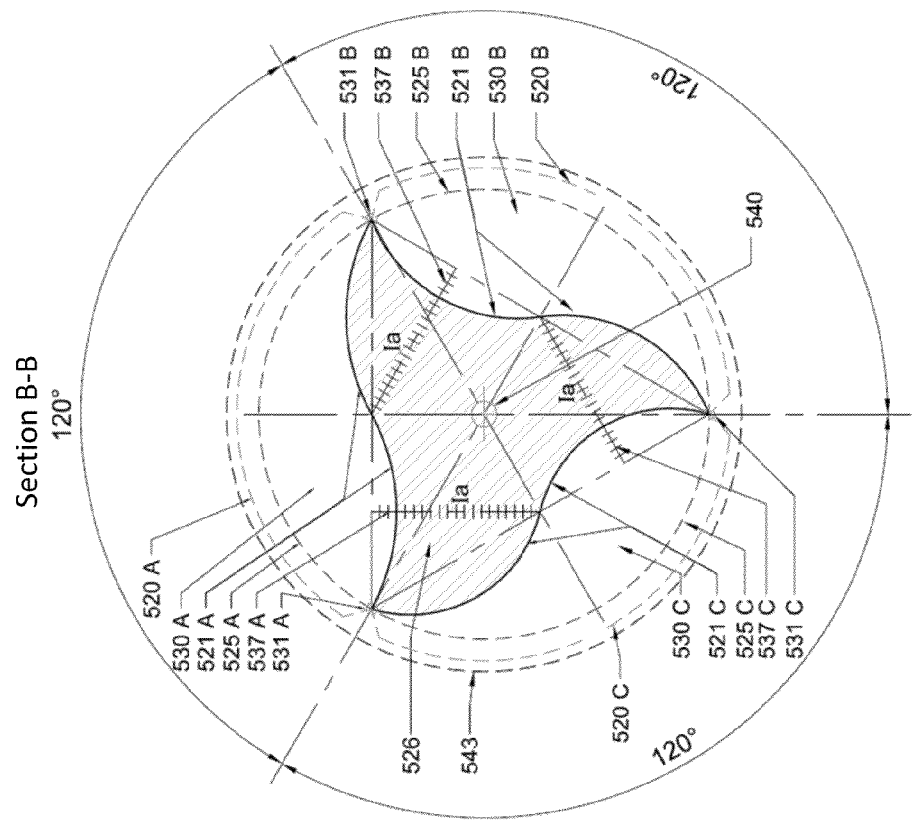
FIGS. 5D and 5E are transverse cross-sectional views of the three-sided rotary offset bone drill of FIG. 5A-5C.
Figure 5D:
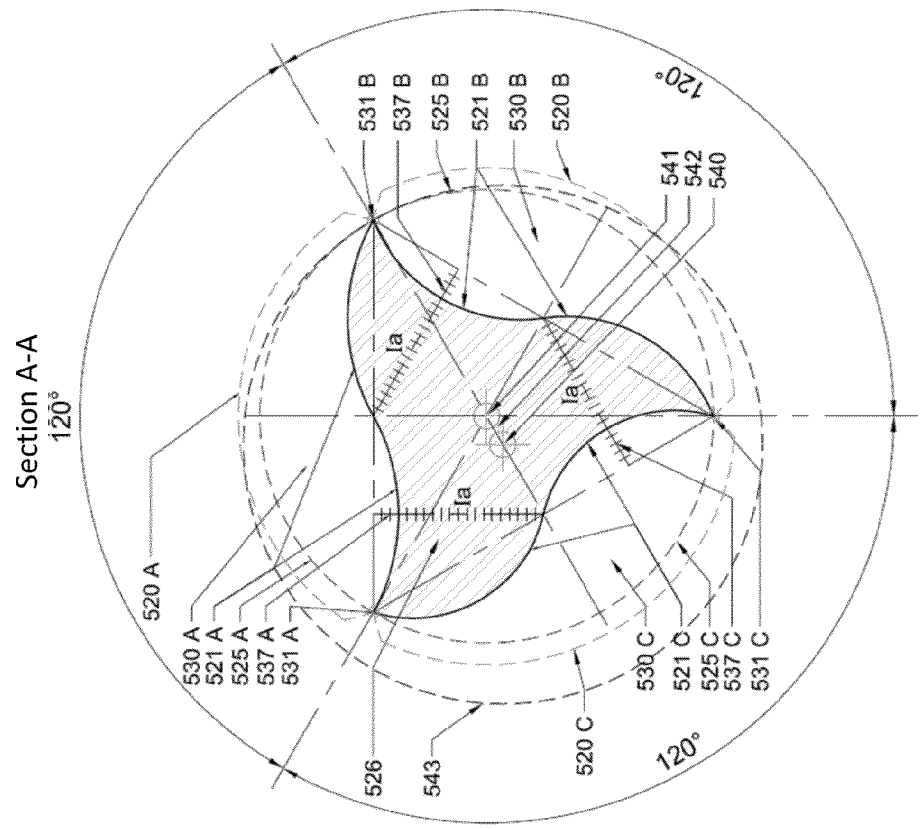

The MxFD 517 is located near the shank 511 end of the working portion 512. The MnFD 518 is located near the tip 513. The shank 511 above the working portion 512 is essentially cylindrical and exhibits a slightly larger diameter than the cutting surface at the MxFD 517. With reference in particular to FIGS. 5D-5F, those skilled in the art will recognize that the center of mass of a cross-section at the MxFD 517 is offset from the axis of rotation 540 of the bone drill 510. However, the center of mass of a cross-section at the MnFD 518 coincides with the axis of rotation 540.

As shown in FIGS. 5A-5F, the bone drill 510 defines three continuous helical flutes 520A, 520B, and 520C. The flutes 520A, 520B, and 520C are substantially concave grooves which follow the circumference of the working portion 512 as spirals between the shank 511 and the leading tip 513 to define concentric circles. In some embodiments, the flutes 520A, 520B, and 520C may be equidistant from each other. In particular embodiments, the flutes 520A, 520B, and 520C may become increasingly tighter or more numerous as they approach the tip 513. The total number of turns per flute of the flutes 520A, 520B, and 520C from MxFD 517 to the MnFD 516 can depend on the total length of the working portion 512, but is not less than one-quarter of one complete revolution. Helical flutes 520A, 520B, and 520C each originate at the MxFD 517 at separate locations that are equally spaced apart around the circumference of the shank 511, or more specifically at 120 degrees of separation.

As best seen in FIGS. 5D and 5E, the flutes 520A, 520B, and 520C are defined by surfaces of S-shaped splines 521A, 521B, and 521C. The flutes 520A, 520B, and 520C intersect to form helical cutting edges 525A, 525B, and 525C between the periphery of the shank 511 and tip 513. The helical flutes 520A, 520B, and 520C cooperate to form a web or core 526, which is essentially triangular. The areas of radial clearance or cut-outs 530A, 530B, and 530C of the flutes 521A, 521B, and 521C outline the web or core 526. In transverse cross-section from the shank 511 to the tip 513, the splines 521A, 521B, and 521C of cutting flutes 520A, 520B, and 520C form arcuate shaped clearance areas of variable depth. The cutting edges 525A, 525B, and 525C and the splines of the inner walls 521A, 521B, and 521C circumscribe clearance areas 530A, 530B, and 530C.

With further reference to FIGS. 5D and 5E, it can be seen that the S-shaped splines 521A, 521B, and 521C intersect the periphery of the shank 511 at points 531A, 531B, and 531C. In some embodiments, these intersections are equal distances apart, and at 120° of separation to form a neutral cutting angle (90° angle to the tangent of the perimeter of shank 511) or slightly positive rake angle (greater than 90° to the tangent of the perimeter of the shank 511). It should be recognized that this cutting angle maybe either negative or positive (that is, less than or greater than 90° to the tangent of the perimeter of the shank 511). In this embodiment, lines drawn to connect points 531A, 531B, and 531C form an equilateral triangle. However, those skilled in the art will also recognize that points 531A, 531B, and 531C may be separated by varying degrees and/or distances rendering the cross-section albeit triangular, asymmetrical (for example, at 110, 125, and 125 degrees of separation, or at other degrees of separation). It will also be recognized that splines 521A, 531B, and 521C may be variable in depth and shape and may have any of a myriad of different configurations.

In this example bone drill 510, the splines 521A, 521B, and 521C are S-shaped and are individually symmetrical. The bisector of each spline divides the spline equally into convex and a concave segments which form the S-shaped profile. The lines that bisect each spline 521A, 521B, and 521C can be drawn to the centroid of the core 526 and are equal in length. Further, an alternate bisector can be drawn from the bisect center point of each spline 521A, 521B, and 521C through the greatest concavity the adjacent spline 521A, 521B, and 521C. Lines drawn perpendicular to the alternate bisector lines form an equilateral triangle. The bisectors for each spline 521A, 521B, and 521C are equal. The greatest depth of each spline can be defined by a segment of Ia (refer to FIGS. 5D and 5E). These depths can vary and, furthermore, can be calculated as a percentage of the length of Ia. The greatest depths of splines 521A, 521B, and 521C, indicated with demarcated line segments 537A, 537B, and 537C, are about 15%, 20%, or 25% of the length of Ia, respectively. The greatest convexities of splines 521A, 521B, and 521C are mirror images of the greatest concavities of the same splines. While the depth and height of each spline 521A, 521B, and 521C can vary, the cross-sectional diameter of the core portion 526 is generally not narrower than about 20% percent of the diameter of the shank 511.

As stated above, the bone drill 510 is an example of a three-sided rotary offset bone drill embodiment. In regard to the offset feature, and further referencing FIGS. 5D-5F, the drill 510 has a center-line or axis of rotation 540 (about which the drill 510 rotates when in use), and a mass axis 541 that does not coincide with the axis of rotation 540. The mass axis 541 is a line defined by the centers of mass of consecutive cross-sectional areas of the bone drill 510. The offset is the difference between the mass axis 541 and the axis of rotation 540 (which are displaced a distance 542 away from each other). The offset distance 542 decreases continuously from the shank 511 to the tip 513, and is zero at the end-point 546. This unique offset feature allows the instrument 510 to cut with a precessional motion. Accordingly, the bone drill 510 cuts a cavity in bone or prepares an osteotomy that is tapered.

FIGS. 6A-6F illustrate another example bone drill 610. The bone drill 610 is another example of a three-sided rotary offset bone drill embodiment. The offset bone drill 610 has three sides, is generally triangular in transverse cross-section, and can be utilized to remove bone. The bone drill instrument 610 includes a shank 611, a free end or tip 613, and a working portion 612 therebetween. The diameter of the working portion 612 is slightly tapered, that is, increasing in diameter from the shank 611 to the tip 613. Alternatively, the diameter of the working portion 612 can remain substantially constant along the length of the working portion 612. The working portion 612 of the drill 610 defines three flutes 620A, 620B, and 620C. As will be described further, the bone drill 610 cuts a bone cavity or prepares an osteotomy that is generally cylindrical.

A fitting 615, which is suitable for releasably coupling to an engine driven motor with a hand-piece and chuck, or a handle utilized for manual instrumentation, can be attached to the shank 611.

The tip 613 can include an active or cutting surface that is confluent the working portion 612 (for example, like the tip shown in FIGS. 7A1 and 7B1). Alternatively, the leading tip 613 can include a non-active or non-cutting surface that is confluent with the working portion 612 (for example, like the tip shown in FIGS. 14A and 14B).

Figure 6F:
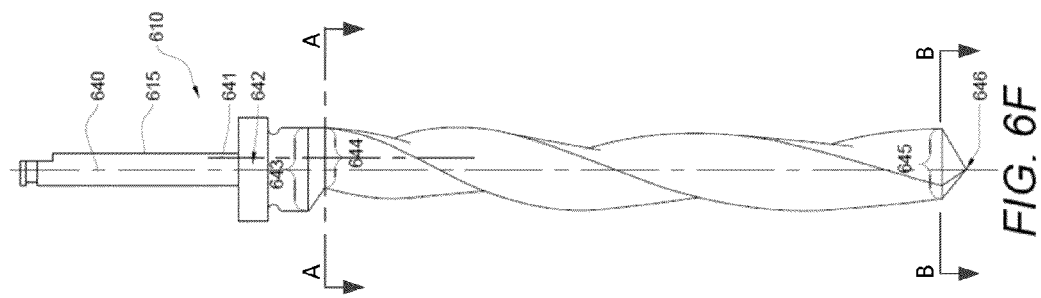
FIGS. 6A-6C and 6F show views of an example three-sided rotary offset bone drill that is slightly wider at the tip than at the shank end. This instrument can be used, for example, to prepare an osteotomy for implant placement or used for bone sequestration. In some embodiments, this style of instrument is designed to cut a parallel cutting envelope.
Figure 6A:
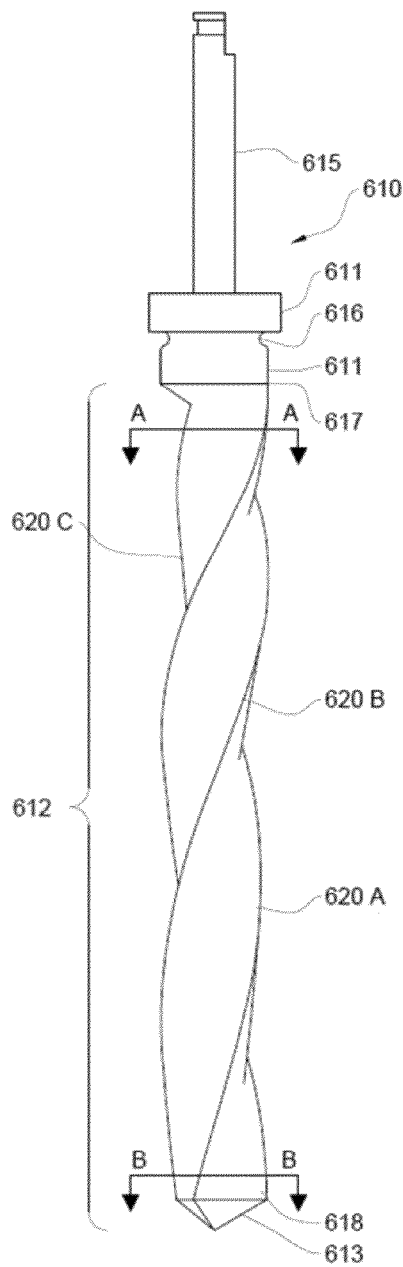
Figure 6B:
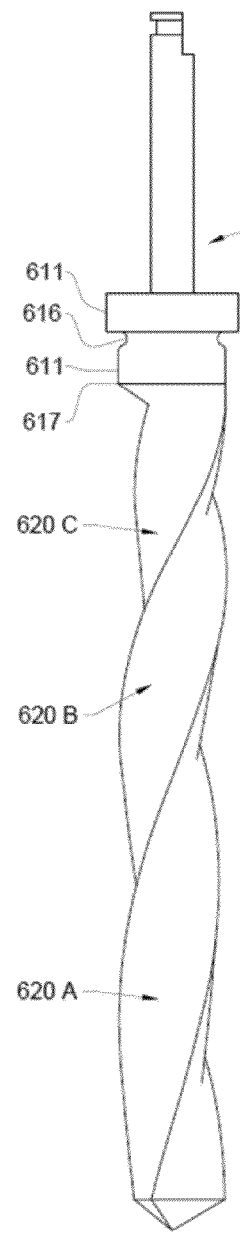
Figure 6C:
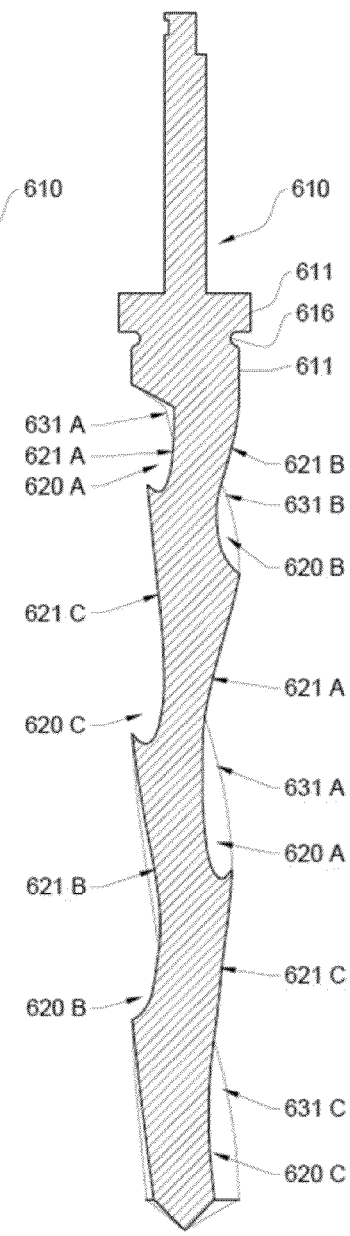
Figure 6E:
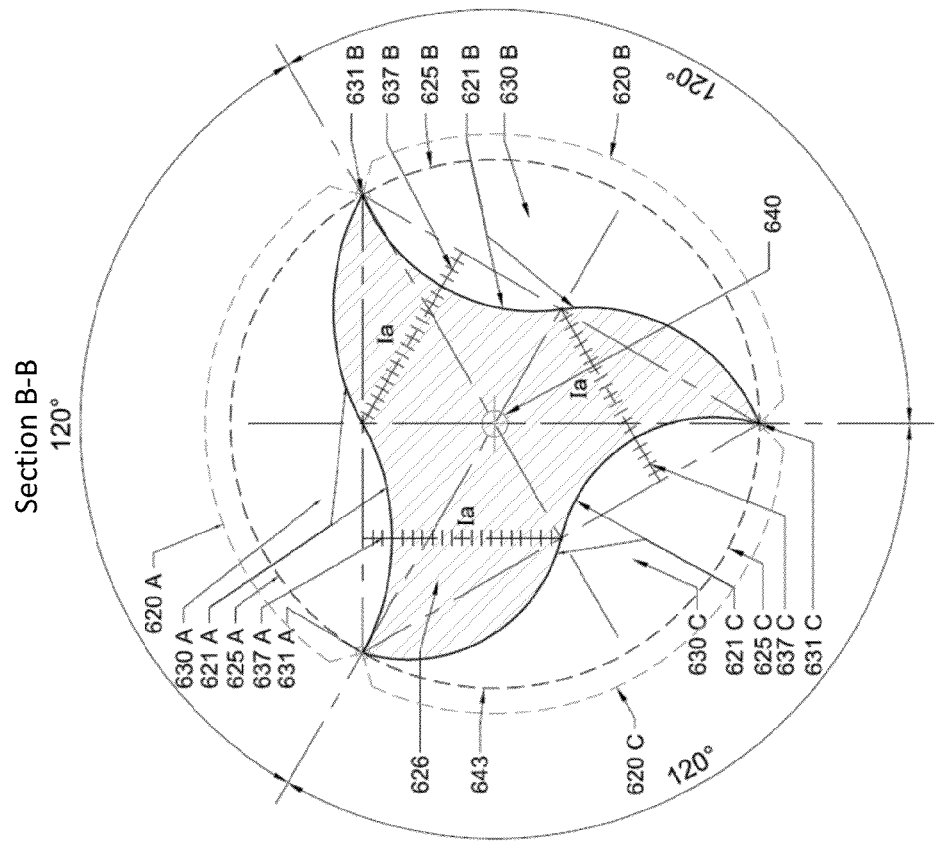
FIGS. 6D and 6E are transverse cross-sectional views of the three-sided rotary offset bone drill of FIGS. 6A-6C.
Figure 6D:
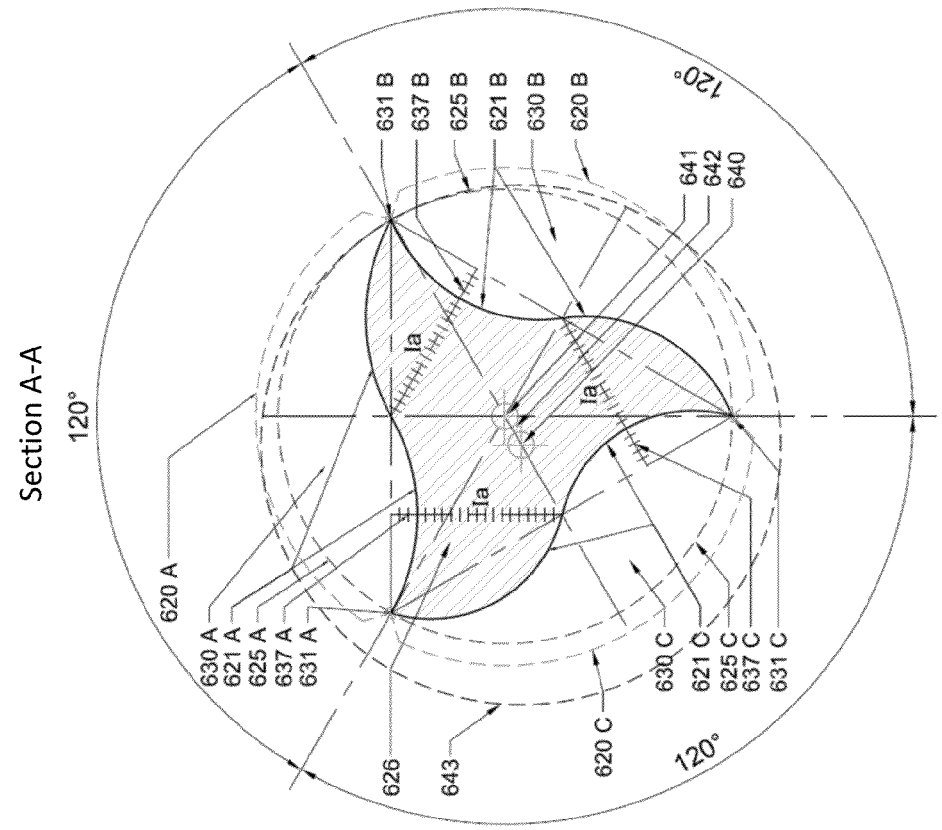

The MnFD 617 is located near the shank 611 end of the working portion 612. The MxFD 618 is located near the tip 613. The shank 611 above the working portion 612 is essentially cylindrical and exhibits a slightly larger diameter than the cutting surface at the MnFD 617. With reference in particular to FIGS. 6D-6F, those skilled in the art will recognize that the center of mass of a cross-section at the MnFD 617 is offset from the axis of rotation 640 of the bone drill 610. However, the center of mass of a cross-section at the MxFD 618 coincides with the axis of rotation 640.

As shown in FIGS. 6A-6F, the bone drill 610 defines three continuous helical flutes 620A, 620B, and 620C. The flutes 620A, 620B, and 620C are substantially concave grooves which follow the circumference of the working portion 612 as spirals between the shank 611 and the leading tip 613 to define concentric circles. In some embodiments, the flutes 620A, 620B, and 620C may be equidistant from each other. In some embodiments, the flutes 620A, 620B, and 620C may become increasingly tighter or more numerous as they approach the tip 613. The total number of turns per flute of the flutes 620A, 620B, and 620C from MnFD 617 to the MxFD 616 can depend on the total length of the working portion 612, but is not less than one-quarter of one complete revolution. Helical flutes 620A, 620B, and 620C each originate at the MnFD 617 at separate locations that are equally spaced apart around the circumference of the shank 611, or more specifically at 120 degrees of separation. Each helical structure of the bone drill 610, i.e., the mass between the flutes 620A, 620B, and 620C and defining the flutes 620A, 620B, and 620C, is continuous along the length of the cutting surface 612 from the shank 611 to the leading tip 613.

With further reference to FIGS. 6D and 6E, it can be seen that the S-shaped splines 621A, 621B, and 621C intersect the periphery of the shank 611 at points 631A, 631B, and 631C. In some embodiments, these intersections are equal distances apart, and at 120° of separation to form a neutral cutting angle (90° angle to the tangent of the perimeter of shank 611) or slightly positive rake angle (greater than 90° to the tangent of the perimeter of the shank 611). It should be recognized that this cutting angle maybe either negative or positive (that is, less than or greater than 90° to the tangent of the perimeter of the shank 611). In this embodiment, lines drawn to connect points 631A, 631B, and 631C form an equilateral triangle. However, those skilled in the art will also recognize that points 631A, 631B, and 631C may be separated by varying degrees and/or distances rendering the cross-section albeit triangular, asymmetrical (for example, at 110, 125, and 125 degrees of separation, or at other degrees of separation). It will also be recognized that splines 621A, 631B, and 621C may be variable in depth and shape and may have any of a myriad of different configurations.

In this example bone drill 610, the splines 621A, 621B, and 621C are S-shaped and are individually symmetrical. The bisector of each spline divides the spline equally into convex and a concave segments which form the S-shaped profile. The lines that bisect each spline 621A, 621B, and 621C can be drawn to the centroid of the core 626 and are equal in length. Further, an alternate bisector can be drawn from the bisect center point of each spline 621A, 621B, and 621C through the greatest concavity the adjacent spline 621A, 621B, and 621C. Lines drawn perpendicular to the alternate bisector lines form an equilateral triangle. The bisectors for each spline 621A, 621B, and 621C are equal. The greatest depth of each spline can be defined by a segment of Ia (refer to FIGS. 6D and 6E). These depths can vary and, furthermore, can be calculated as a percentage of the length of Ia. The greatest depths of splines 621A, 621B, and 621C, indicated with demarcated line segments 637A, 537B, and 537C, are about 15%, 20%, and 25% of the length of Ia, respectively. The greatest convexities of splines 621A, 621B, and 621C are mirror images of the greatest concavities of the same splines. While the depth and height of each spline 621A, 621B, and 621C can vary, the cross-sectional diameter of the core portion 626 is generally not narrower than about 20% percent of the diameter of the shank 611.

As stated above, the bone drill 610 is an example of a three-sided rotary offset bone drill embodiment. In regard to the offset feature, and further referencing FIGS. 6D-6F, the drill 610 has a center-line or axis of rotation 640 (about which the drill 610 rotates when in use), and a mass axis 641 that does not coincide with the axis of rotation 640. The mass axis 641 is a line defined by the centers of mass of consecutive cross-sectional areas of the bone drill 610. The offset is the difference between the mass axis 641 and the axis of rotation 640 (which are displaced a distance 642 away from each other). The offset distance 642 decreases continuously from the shank 611 to the tip 613, and is zero at the end-point 646. This unique offset feature allows the instrument 610 to cut with a precessional motion. Accordingly, the bone drill 610 cuts a cavity in bone or prepares and osteotomy that is substantially cylindrical.

The features of the various bone drill embodiments described herein can be combined together in any suitable combination. For example, a bone drill having the cross-sectional shape of bone drill 410 could be used with tapered diameters of bone drills 510, 610, or 810. In another example, a first portion of a bone drill can have the cross-sectional shape of the bone drill 410, and a second portion of the same bone drill can have the cross-sectional shape of the bone drills 510 or 610. In another example, a bone drill with three flutes such as drills 510 and 610 can have a consistent diameter along the entire working lengths 512 and 612 respectively. In still another example, a bone drill of the shape of 510 of FIG. 5 could be used with decreasing diameter of bone drill 610 of FIG. 6. Similarly, other such combinations and sub-combinations are envisioned within the scope of this document.

FIG. 6G illustrates the differential between the sizes and shapes of the cutting envelopes of the drill 510 of FIGS. 5A-F and the drill 610 of FIGS. 6A-6F. Drill 510 exhibits a tapered cutting envelope, while drill 610 exhibits a parallel or cylindrical cutting envelope. The tapered cutting envelop of drill 510 is depicted by profile 800 (with solid lines), and the parallel cutting envelope of drill 610 is depicted by profile 801 (with dashed lines).

Figure 6H:
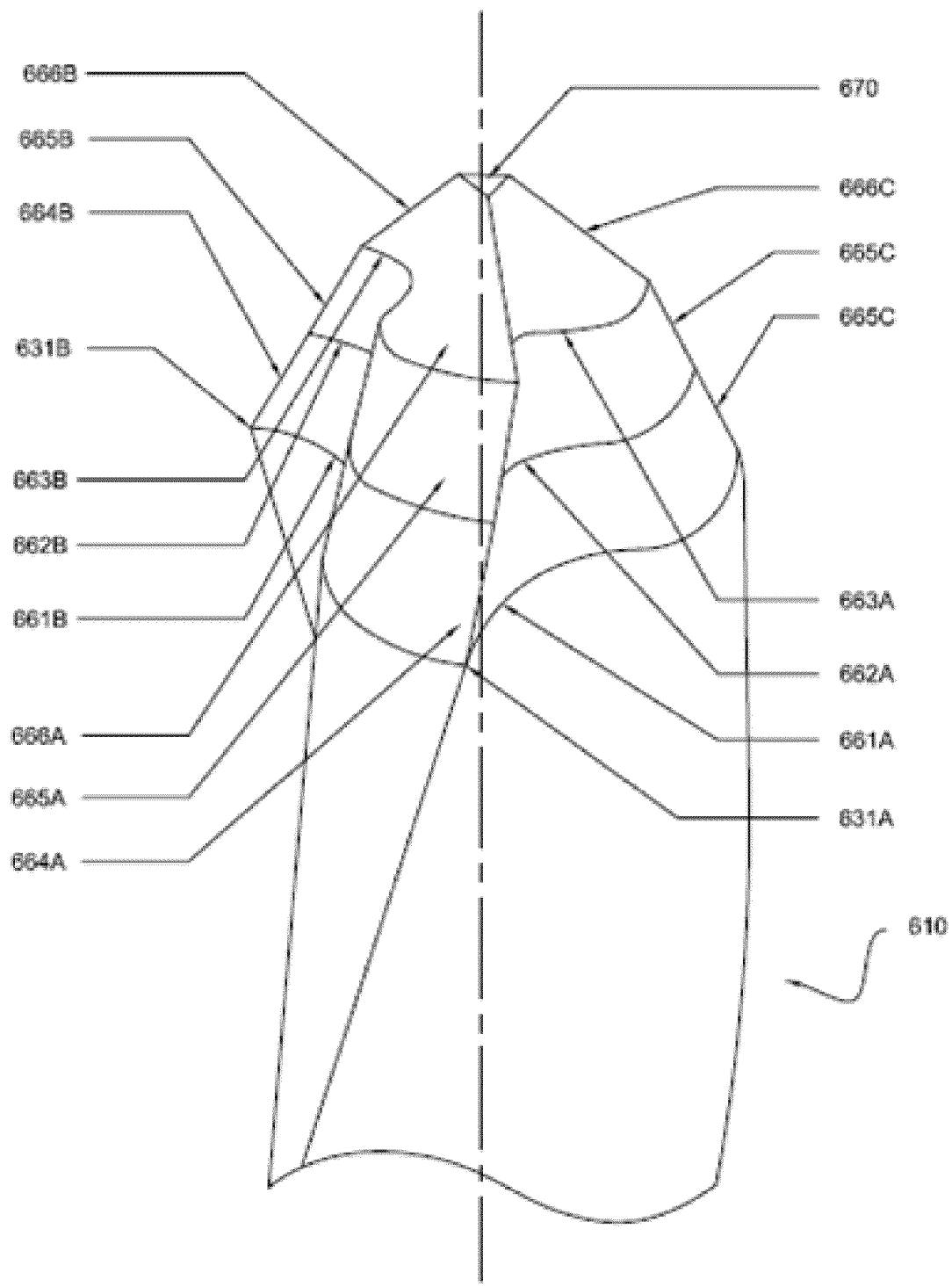
FIG. 6H is a side view of the tip of the instrument of FIGS. 6A-6F.
Figure 6I:
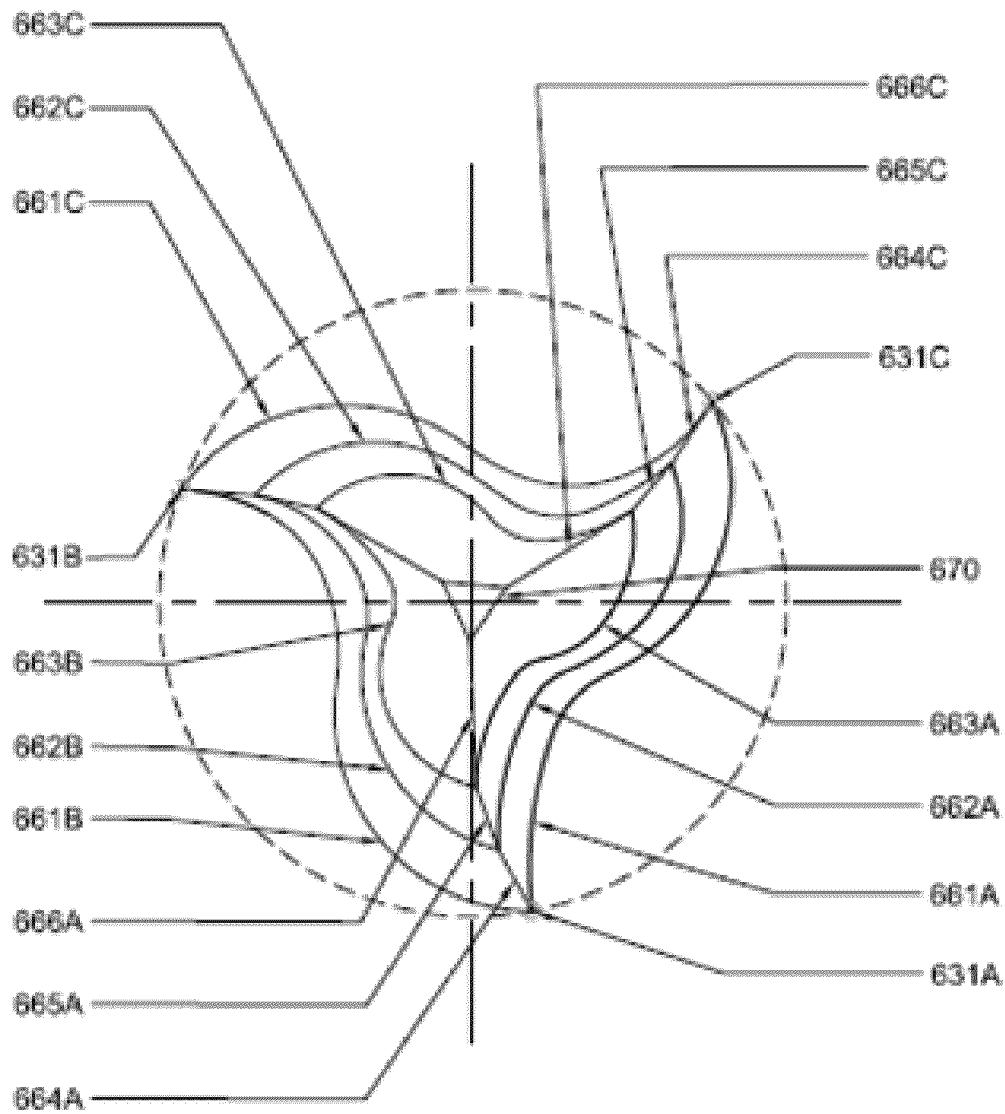
FIG. 6I is an end view of the tip of the instrument of FIGS. 6A-6F.

Referring now also to FIGS. 6H and 6I, the tip 613 of drill 610 is essentially pyramidal with three sides and unlike most chisel tips, which are two sided. Emanating from the sharp tip 670 are three incline planes or facets 666A, 666B, and 666C which cooperate to form the first set of cutting lips limited in length by edges 663A, 663B, and 663C. In this embodiment, and when viewed from the side, the first incline plane or facet extends laterally away from the central axis and approximates 60 degrees. Thus, in a side view, any two incline planes cooperate to form an angle that approximates 120 degrees. This angle may be increased when used to drill softer materials and decrease when drilling harder materials. This first set of facets is subtended by a second set of facets 665A, 665B, and 665C, which are shorter in length than the first set of facets, and cooperate to form a second set of lips limited in length by edges 662A, 662B, and 662C. This second set of facets and lips extend away from the central axis at an angle that is less than the angle of the first set of facets. The second set of facets is subtended by a third set of facets 664A, 664B, and 664C which are limited in length by edges 661A, 661B, and 661C. The third set of facets and lips extend away from the central axis at an angle that is even less than the angle of the first set and second set of facets.

Multi-faceted tip configurations can improve self-centering ability, hole geometry or symmetry, reduce exit burr production, improve chip breakage and hauling capacity, and reduce the axial force or thrust required to operate the drill. Dependent on the needs of the operator and the quality and hardness of the work piece, the numbers of facets and the angle of the incline planes of each facet can be increased or decreased. Designs such as these will work synergistically with precessional cutting tools with offset transverse cross-sections to further improving cutting efficiency.

In the embodiments of FIGS. 3A-6E, the point at the free end or tip, e.g., the point 322 at the end of the tip 320, is on the axis of rotation. However, this is not required. For example, the pointed end of the tip can be offset from the axis of rotation. FIGS. 7A1 and 7B1 show examples of offset tips (pointed ends that are offset from the axis of rotation) in accordance with some embodiments. This can be the case where the center of mass of the tip end of the working portion coincides with the axis or rotation, and/or where the center of mass of the tip end of the working portion is offset from the axis of rotation.

Referring now to FIGS. 7A1 and 7B1 that show examples of active tips 710 and 720 of a pilot drill. Those skilled in the art will recognize that, similar to a bone drill that has an offset profile, the tip may also be offset from the drill's axis of rotation. FIG. 7B1 shows a chisel tip that displays incline planes 700B and 703B that are relatively equal. FIG. 7A1, however, shows a chisel tip where the incline 700A is shorter and less acute than the incline plane of 703A. The diagrams also illustrate that the surface areas formed by facets 701A and 702A are smaller in combination than the surface area formed by facet 703A. It should also be recognized that a bone drill that is offset from shank to tip will also display an inherent offset in the distal extent of the drill and or tip. In some embodiments, the tips can remain substantially centered when in use.

FIGS. 7A-7F illustrate another example bone drill 710. The bone drill 710 is a three-sided rotary offset bone drill embodiment that is generally triangular in transverse cross-section. The offset bone drill 710 has three sides, is generally triangular in transverse cross-section, and can be utilized to remove bone. The offset bone drill instrument 710 includes a shank 711, a tip 713 (also referred to herein as a free end), and a working portion 712 therebetween. In some embodiments, the diameter of the working portion 712 is slightly tapered, that is, increasing in diameter from the shank 711 to the tip 713. Alternatively, the diameter of the working portion 712 can remain substantially constant along the length of the working portion 712, or can be tapered such that the diameter decreases from the shank 711 to the tip 713. The working portion 712 of the drill 710 defines three flutes 720A, 720B, and 720C. As will be described further, the bone drill 710 cuts a bone cavity or prepares an osteotomy that is generally cylindrical.

A fitting 715, which is suitable for a releasably coupling to an engine driven motor with a hand-piece and chuck, or a handle utilized for manual instrumentation, can be attached to the shank 711.

The tip 713 can include an active or cutting surface that is confluent with the working portion 712 (for example, like the tip shown in FIGS. 7A1 and 7B1). Alternatively, the leading tip 713 can include a non-active or non-cutting surface that is confluent with the working portion 712.

Figure 7E:
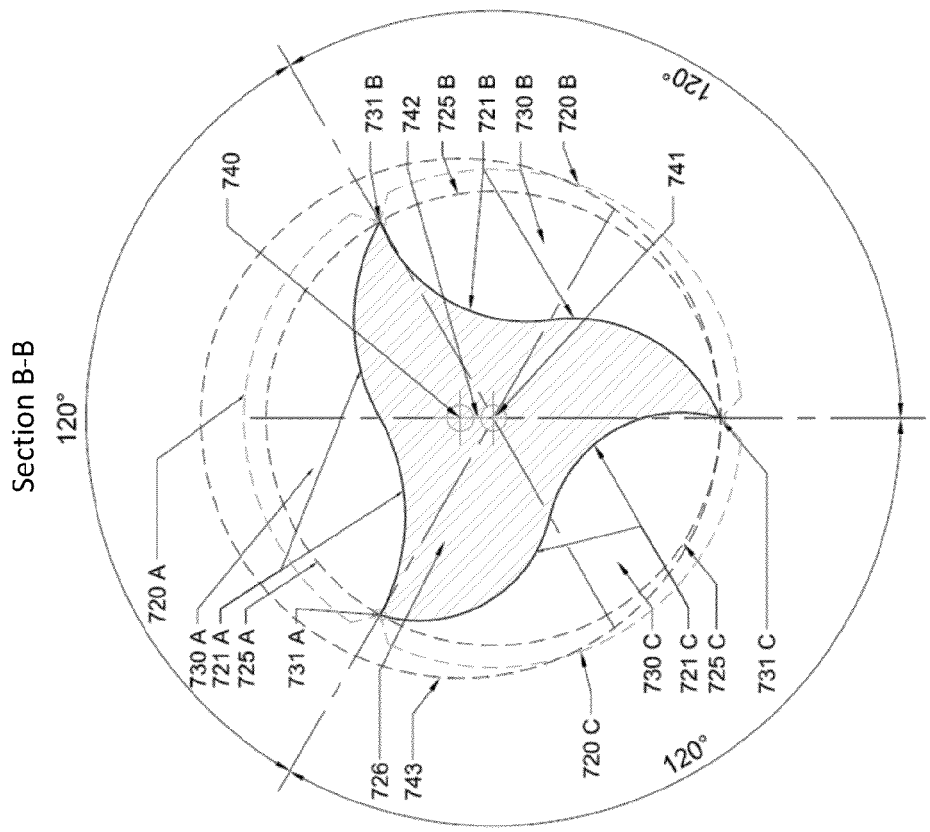
FIGS. 7D and 7E are transverse cross-sectional views of the three-sided rotary offset bone drill of FIGS. 7A-7C.
Figure 7D:
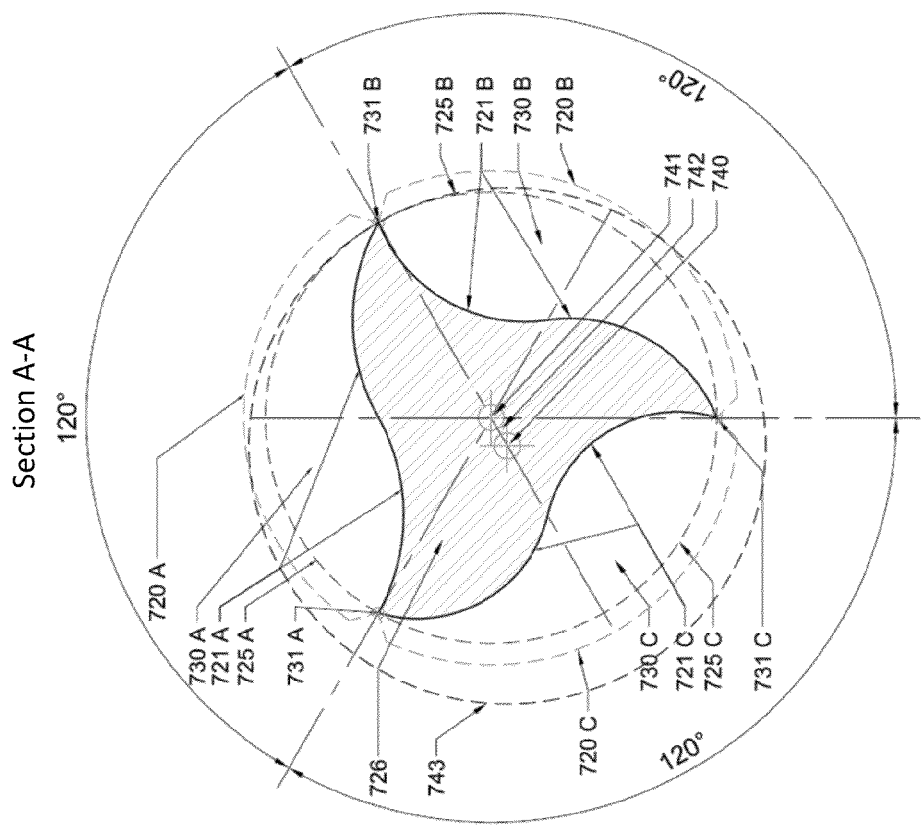
Figure 7F:
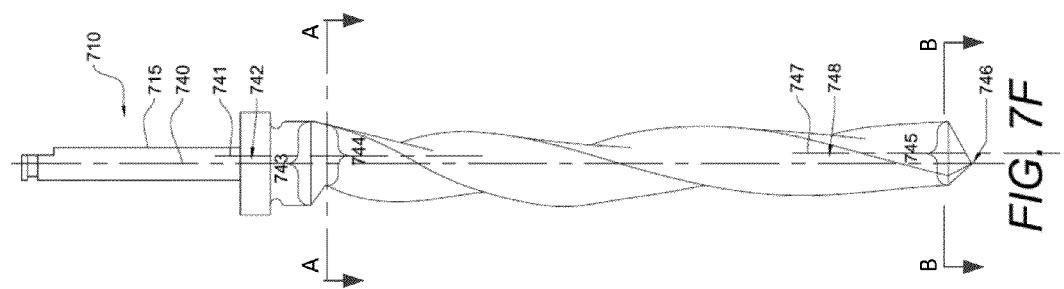

In the depicted embodiment, the MnFD 717 is located near the shank 711 end of the working portion 712, and the MxFD 718 is located near the tip 713. The shank 711 above the working portion 712 is essentially cylindrical and exhibits a slightly larger diameter than the cutting surface at the MnFD 717. With reference in particular to FIGS. 7D-7F, those skilled in the art will recognize that the center of mass 741 of a cross-section at the MnFD 717 (cross-section A-A in FIG. 7D) is offset from the axis of rotation 740 of the bone drill 710. In addition, the center of mass 741 of a cross-section at the MxFD 718 (cross-section B-B in FIG. 7E) is also offset from the axis of rotation 740. While the centers of mass of the cross-sections 717 and 718 (and the centers of mass of the cross-sections therebetween) are offset from the axis of rotation, in this embodiment the pointed end of the tip 713 coincides with the axis of rotation. However, in alternative embodiments the pointed end of the tip can also be offset from the axis of rotation.

As shown in FIGS. 7A-7F, the bone drill 710 defines three continuous helical flutes 720A, 720B, and 720C that spiral along the length of the working portion 712. The flutes 720A, 720B, and 720C are substantially concave grooves that follow the circumference of the working portion 712 as spirals between the shank 711 and the leading tip 713 to define concentric circles. In some embodiments, the flutes 720A, 720B, and 720C may be equidistant from each other. In some embodiments, the flutes 720A, 720B, and 720C may become increasingly tighter or more numerous as they approach the tip 713. The total number of turns per flute of the flutes 720A, 720B, and 720C from MnFD 717 to the MxFD 718 can depend on the total length of the working portion 712, but is typically not less than one quarter of one complete revolution. Helical flutes 720A, 720B, and 720C each originate at the MnFD 717 at separate locations that are spaced relatively equally apart around the circumference of the shank 711, or more specifically at about 120 degrees of separation.

With further reference to FIGS. 7D and 7E, it can be seen that the S-shaped splines 721A, 721B, and 721C define cutting edges at points 731A, 731B, and 731C. In some embodiments, these intersections are equal distances apart, and at about 120° of separation to form a neutral cutting angle (90° angle to the tangent of the perimeter of shank 711) or slightly positive rake angle (greater than 90° to the tangent of the perimeter of the shank 711). It should be recognized that this cutting angle may be either negative or positive (that is, less than or greater than 90° to the tangent of the perimeter of the shank 711). In this embodiment, lines drawn to connect points 731A, 731B, and 731C form an equilateral triangle. However, those skilled in the art will also recognize that points 731A, 731B, and 731C may be separated by varying degrees and/or distances rendering the cross-section albeit triangular, asymmetrical (for example, at 110, 125, and 125 degrees of separation, or at other degrees of separation). It will also be recognized that splines 721A, 731B, and 721C may be variable in depth and shape and may have any of a myriad of different configurations.

In this example bone drill 710, the splines 721A, 721B, and 721C are S-shaped and are individually symmetrical. The bisector of each spline divides the spline equally into convex and a concave segments which form the S-shaped profile. The lines that bisect each spline 721A, 721B, and 721C can be drawn to the centroid 741 of the core 726 and are equal in length. Further, an alternate bisector can be drawn from the bisect center point of each spline 721A, 721B, and 721C through the greatest concavity the adjacent spline 721A, 721B, and 721C. Lines drawn perpendicular to the alternate bisector lines form an equilateral triangle. The bisectors for each spline 721A, 721B, and 721C are equal. As mentioned previously, the greatest depth of each spline 721A, 721B, and 721C can vary in some embodiments. While the depth and height of each spline 721A, 721B, and 721C can vary, the cross-sectional diameter of the core portion 727 is generally not narrower than about 20% percent of the diameter of the shank 711. However, in some embodiments, the cross-sectional diameter of the core portion 727 can be narrower than about 20% percent of the diameter of the shank 711.

As stated above, the bone drill 710 is an example of a three-sided rotary offset bone drill embodiment. In regard to the offset feature, and further referencing FIGS. 7D-7F, the drill 710 has an axis of rotation 740 (about which the drill 710 rotates when in use), and a mass axis 741 that does not consistently coincide with the axis of rotation 740. In other words, the mass axis 741 is offset from the axis of rotation 740.

The mass axis 741 is the continuum of points defined by the collection of the centroids (centers of mass) of each transverse cross-sectional area along the working portion 712. In this embodiment, the mass axis 741 is offset from the axis of rotation 740 by a distance 742. In this embodiment, the offset distance 742 remains relatively consistent from the shank 711 to the tip 713, and linear. This unique offset feature allows the instrument 710 to cut with a precessional motion. Accordingly, the bone drill 710 cuts a cavity in bone or prepares and osteotomy that is substantially cylindrical.

In some drill instrument embodiments, some or all of the mass axis can be offset from the axis of rotation, and other spatial relationships can exist therebetween (other than the relatively consistent distance 742 and linear mass axis 741 of drill bit 710). For example, in some embodiments some or all of the mass axis can approximate a helical form that revolves around the axis of rotation. In other embodiments, some or all of the mass axis can form a spiral around the axis of rotation. In some embodiments, the mass axis can intersect the axis of rotation along a portion of the working length of the instrument, and can be offset from the axis of rotation along other portions of the working length. In particular embodiments, the mass axis intersects the axis of rotation at one or more points, while other points of the mass axis are offset from the axis of rotation. For example, in some embodiments the mass axis can form a wavy, sinusoidal, or curved shape that may intersect the axis of rotation at one or more points.

Designs with multi-faceted cutting lips and multiple point tips are also envisioned within the scope of this disclosure.

FIGS. 8A-8F illustrate another example bone drill 810. The bone drill 810 is an example of a four-sided rotary offset bone drill embodiment. The offset bone drill 810 has four sides, is both quadrilateral and radial in transverse cross-section, and can be utilized to remove bone. The bone drill instrument 810 includes a shank 811, a free end or tip 813, and a working portion 812 therebetween. In this embodiment, the diameter of the working portion 812 is slightly tapered, that is, increasing in diameter from the shank 811 to the tip 813. In other embodiments, the taper may be in the reverse direction, or the drill may have no taper. The working portion 812 of the drill 810 defines four flutes 820A, 820B, 820C and 820D. As will be described further, this embodiment of the bone drill 810 cuts a bone cavity or prepares an osteotomy that is generally cylindrical.

A fitting 815 at the proximal end portion of the bone drill 810 is suitable for a releasably coupling to an engine driven motor with a hand-piece and chuck, or a handle utilized for manual instrumentation. The fitting 815 can extend from the shank 811.

The tip 813 can include an active or cutting surface that is confluent the working portion 812. Alternatively, the leading tip 813 can include a non-active or non-cutting surface that is confluent with the working portion 812.

Figure 8F:
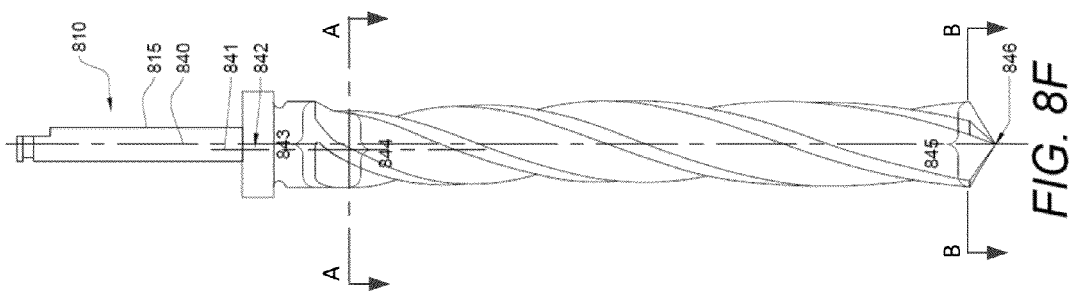
FIGS. 8A-8C and 8F shows an example of an offset four-sided bone drill that is tapered, but cuts a cylindrical cutting envelope. The four splines emanate from the core radially.
Figure 8A:
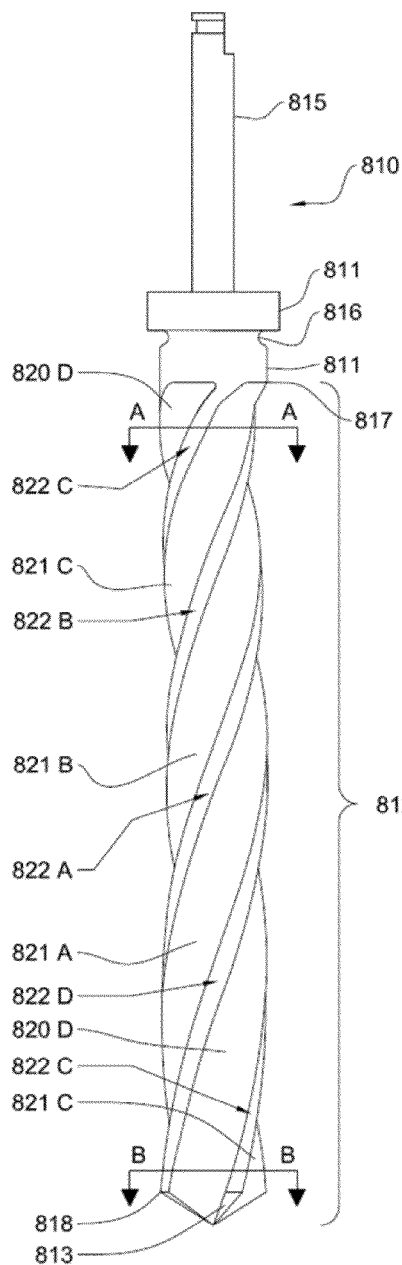
Figure 8B:
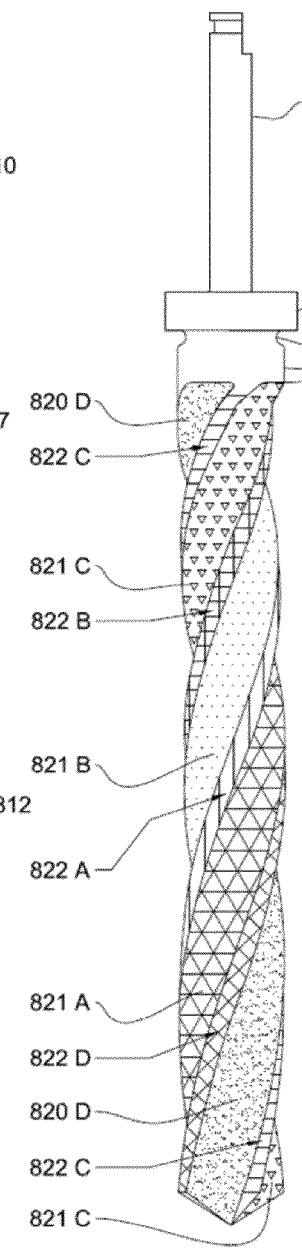
Figure 8C:
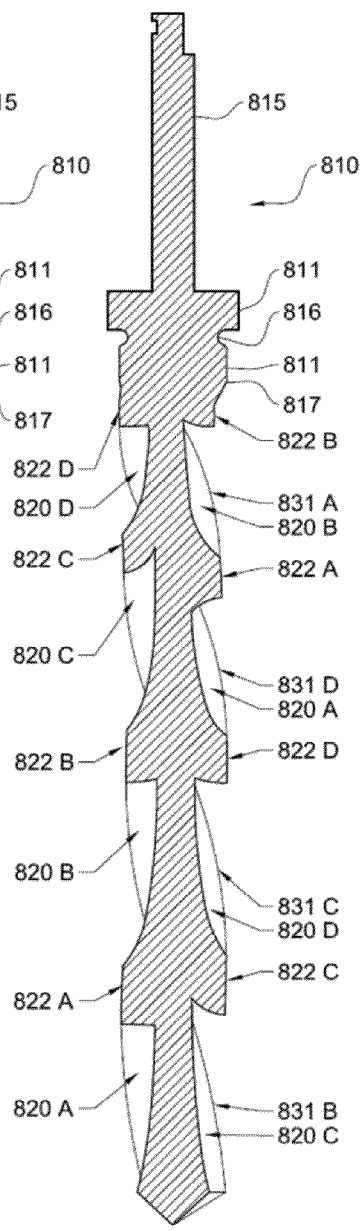
Figure 8E:
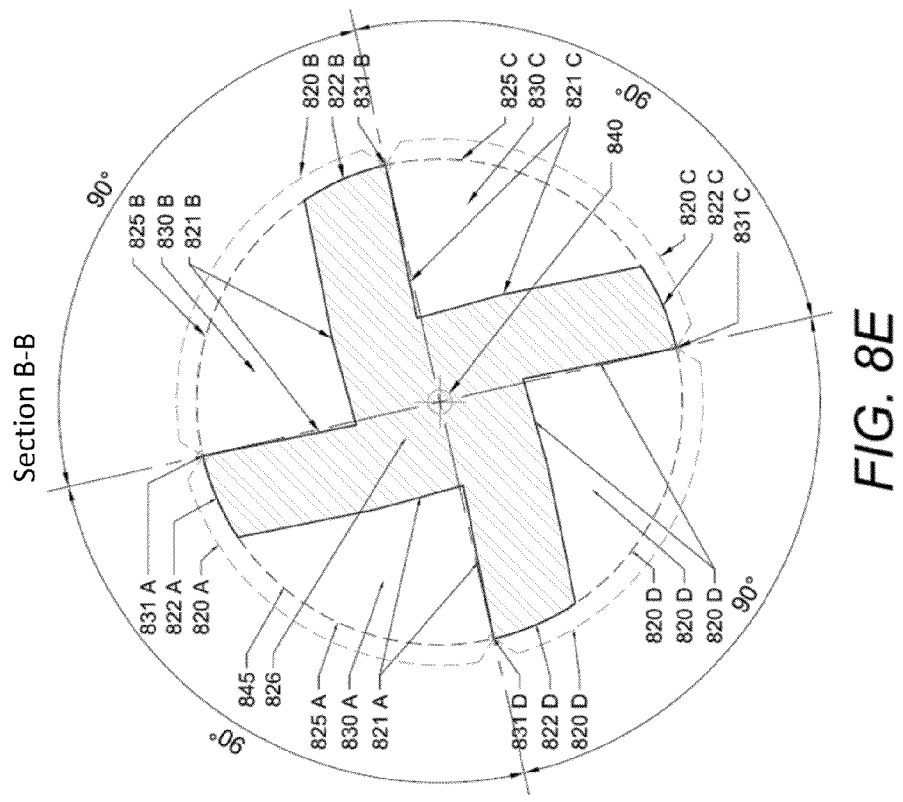
FIGS. 8D and 8E are transverse cross-sectional views of the four-sided rotary offset bone drill of FIGS. 8A-8C.
Figure 8D:
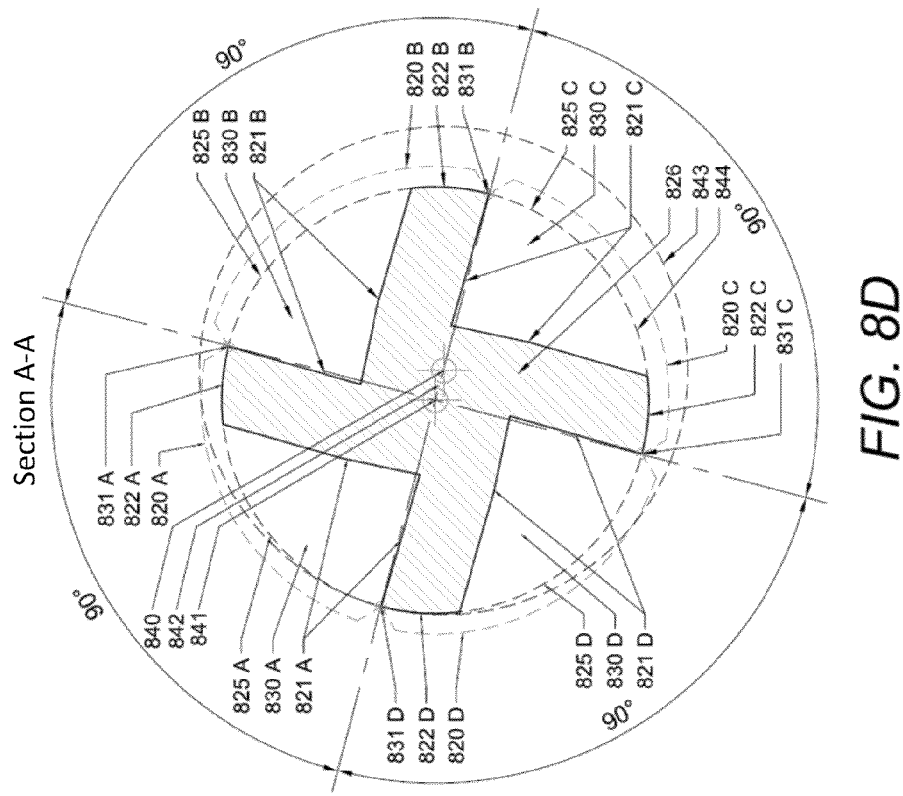
Figure 12F:
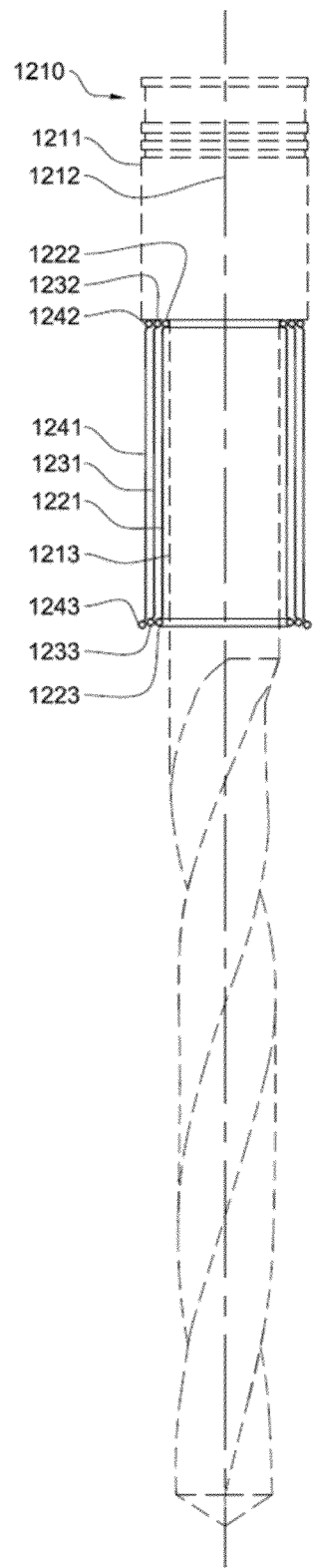
Figure 12G:
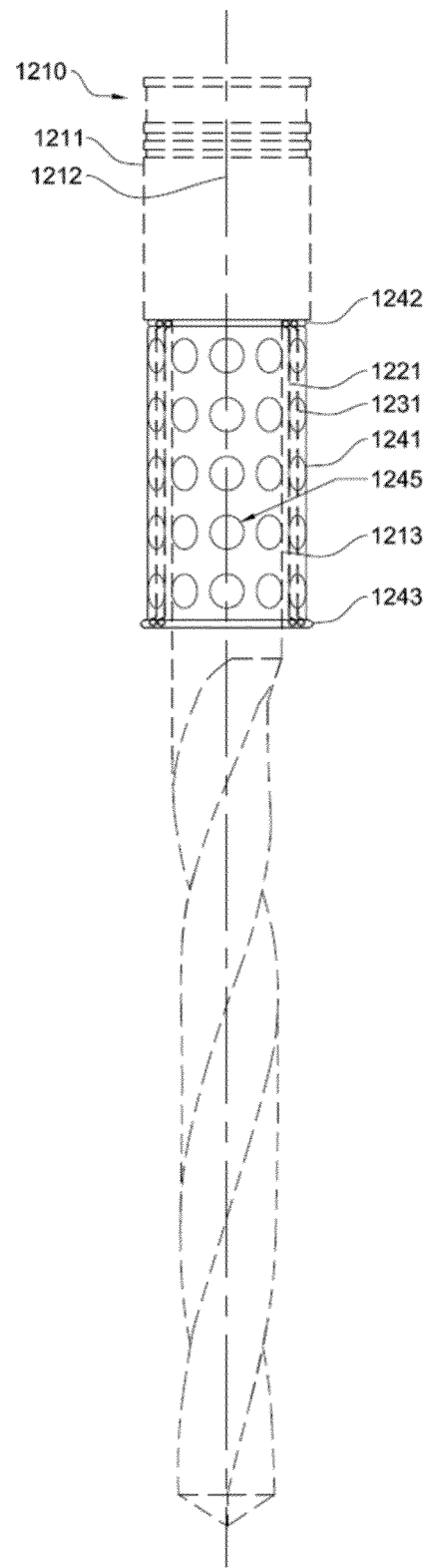

The MnFD 817 is located near the shank 811 end of the working portion 812. The MxFD 818 is located near the tip 813. The shank 811 above the working portion 812 is essentially cylindrical and exhibits a slightly larger diameter than the cutting surface at the MnFD 817. With reference in particular to FIGS. 8D-8F, those skilled in the art will recognize that the center of mass 841 of a cross-section at the MnFD 817 is offset from the axis of rotation 840 of the bone drill 810. However, the center of mass of a cross-section at the MxFD 818 coincides with the axis of rotation 840.

As shown in FIGS. 8A-8F, the bone drill 810 defines four continuous helical flutes 820A, 820B, 820C, and 820D. The flutes 820A, 820B, 820C, and 820D are angular groves, which follow the circumference of the working portion 812 as spirals between the shank 811 and the leading tip 813 to define concentric circles. While the flutes 820A, 820B, 820C, and 820D in the depicted embodiment of bone drill 810 spiral around the axis of rotation between the shank 811 and the leading tip 813, it should be understood that the flutes 820A, 820B, 820C, and 820D can be configured differently in alternative embodiments. For example, in some embodiments the flutes 820A, 820B, 820C, and 820D are linear and extending generally parallel to the longitudinal axis of bone drill 810 (which is coincident with the axis of rotation).

In some embodiments, the flutes 820A, 820B, 820C, and 820D may be equidistant from each other. In some embodiments, the flutes 820A, 820B, 820C, and 820D may become increasingly tighter or more numerous as they approach the tip 813. The total number of turns per flute of the flutes 820A, 820B, 820C, and 820D from MnFD 817 to the MxFD 818 can depend on the total length of the working portion 812, but is generally not less than one-quarter of a complete revolution. In some embodiments, helical flutes 820A, 820B, 820C, and 820D each originate at the MnFD 817 at separate locations, and are equally spaced apart around the circumference of the shank 811, or more specifically are at 90 degrees of separation.

With further reference to FIGS. 8D and 8E, it can be seen that the angular splines 821A, 821B, 821C, and 821D associated with flutes 820A, 820B, 820C, and 820D intersect the periphery of the shank 811 at points 831A, 831B, 831C, and 831D. In this embodiment, these intersections are equal distances apart, and at about 90° of separation. It should be understood, however, that these intersections may be at different points of origin, such as at about 80°, 100°, 80°, and 100°, to provide just one such example.

In this embodiment, splines 821A, 821B, 821C, and 821D form a neutral cutting angle (at about a 90° angle to the tangent of the perimeter of shank 811). Alternatively, the splines may form a positive rake angle (e.g., greater than 90° to the tangent of the perimeter of the shank 811). It is also recognized that this cutting angle may be negative (e.g., less than 90° to the tangent of the perimeter of the shank 811). In this embodiment, lines drawn to connect points 831A, 831B, 831C, and 831D join to form a quadrilateral configuration. However, those skilled in the art will also recognize that points 831A, 831B, 831C, and 831D may be separated by varying degrees and/or distances rendering the cross-section albeit quadrilateral, asymmetrical, for example, at about 80, 85, 95, and 100 degrees of separation (or at other degrees of separation). It will also be recognized that splines 821A, 831B, 821C, and 821D may be variable in depth and shape and may have a wide variety of configurations.

In this example bone drill 810, the splines 821A, 821B, 821C, and 821D are angular (e.g., forming nearly a right angles) adjacent to the web or core 826, and the splines 821A, 821B, 821C, and 821D are individually approximately symmetrical.

The greatest depths of splines 821A, 821B, 821C, and 821D is dictated by the width of the core 826 and can be constant or variable. The cross-sectional diameter of the core portion 826 is, generally, not narrower than about 20% percent of the diameter of the shank 811. But in some cases, the cross-sectional diameter of the core portion 826 may be narrower than about 20% of the diameter of the shank 811.

As stated above, the bone drill 810 is an example of a four-sided rotary offset bone drill embodiment. In regard to the offset feature, and further referencing FIGS. 8D-8F, the drill 810 has a center-line or axis of rotation 840 (about which the drill 810 rotates when in use), and a mass axis 841 that does not coincide with the axis of rotation 840. The mass axis 841 is a line defined by the centers of mass of consecutive cross-sectional areas of the bone drill 810. The offset is the difference between the mass axis 841 and the axis of rotation 840 (which are displaced a distance 842 away from each other). In this embodiment, the offset distance 842 decreases continuously from the shank 811 to the tip 813, and is zero at the end-point 846. This unique offset feature allows the instrument 810 to cut with a precessional motion, which carves a cutting envelope 843 using a cross-section with a smaller cross-section 844. Accordingly, the bone drill 810 cuts a cavity in bone or prepares and osteotomy that remains cylindrical and corresponds to the MXFD 818, with an drill that is substantially smaller in cross-section longitudinally. In other embodiments, the offset distance 842 can different, e.g., zero at the shank 811 and increasing continuously to the tip 813.

The features of the various bone drill embodiments described herein can be combined together in any suitable combination. For example, the bone drill 810 is an example of a four-sided rotary offset bone drill embodiment that increases in diameter from the shank 811 to the tip 813, and other embodiments can also be adapted to include such a taper. For instance, a bone drill having the cross-sectional shape of bone drill 410, 510, 610, or 710 or could be used with tapered diameters of bone drill 810. All combinations and sub-combinations of the features and designs provided herein are within the scope of this disclosure.

Figure 9F:
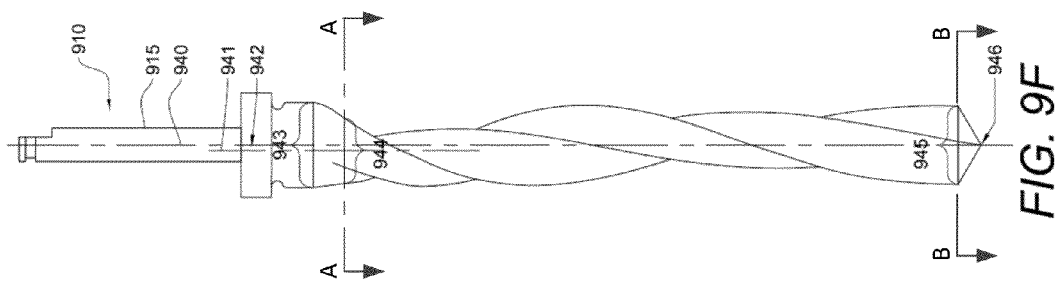

FIGS. 9A1-9C1, 9A2-9C2, 9D1, 9E1, and 9F illustrate another example bone drill 910. FIGS. 9A1-9C1 and 9A2-9C2 show the same bone drill 910, but the views are rotated 90 degrees in relation to each other. That is, FIG. 9A2 is a view of the bone drill 910 from a perspective that is rotated 90 degrees from the view of FIG. 9A1.

The bone drill 910 is an embodiment of a four-sided rotary offset bone drill. The offset bone drill 910 has a transverse cross-section that is shaped approximately as a parallelogram. In particular embodiments, the cross-sectional shape can approximate a rhombus. The bone drill 910 can be utilized to remove bone, and to drill other materials as described herein. The bone drill instrument 910 includes a shank 911, a tip 913 (or free end), and a working portion 912 therebetween. In this embodiment, the diameter of the working portion 912 (as defined by the rotary path of points 931A and 931C, which are the intersections of the splines 921A with 921D, and 921B with 921C) is slightly tapered, that is, increasing in diameter from the shank 911 to the tip 913. In other embodiments, the taper may be in the reverse direction, or the drill may have no taper. The working portion 912 of the drill 910 defines four flutes 920A, 920B, 920C, and 920D. As will be described further, this embodiment of the bone drill 910 cuts a bone cavity or prepares an osteotomy that is generally cylindrical. A fitting 915 at the proximal end portion of the bone drill 910 is suitable for releasably coupling drill 910 to an engine driven motor with a hand-piece and chuck, or a handle utilized for manual instrumentation. The fitting 915 extends from the shank 911.

The tip 913 can include an active or cutting surface that is confluent with the working portion 912 (like the tip shown in FIGS. 7A1 and 7B1). Alternatively, the leading tip 913 can include a non-active or non-cutting surface that is confluent with the working portion 912.

In this embodiment, the MnFD 917 is located near the shank 911 end of the working portion 912, and the MxFD 918 is located near the tip 913. In other embodiments, the locations of the MnFD and MxFD can be elsewhere along the working portion 912. The shank 911 above the working portion 912 is essentially cylindrical and exhibits a slightly larger diameter than the cutting surface at the MnFD 917. With reference in particular to FIGS. 9D1, 9E1, and 9F, those skilled in the art will recognize that the center of mass 941 of a cross-section at the MnFD 917 (refer to FIG. 9D1) is offset from the axis of rotation 940 of the bone drill 910. However, the center of mass of a cross-section at the MxFD 918 coincides with the axis of rotation 940. In other embodiments, the centers of mass of cross-sections at various positions along the working portion of an instrument may form a mass axis that has a different spatial relationship from the axis of rotation (i.e., different than the spatial relationship between the mass axis and axis of rotation defined by drill 910). For example, as described above, some or all of the mass axis may be helical, spiral-shaped, wavy, curved, linear, offset from the axis of rotation, coinciding with the axis of rotation, and so on. In some embodiments, combinations of such features can be included in a single instrument.

As shown in FIGS. 9A1-9C1, 9A2-9C2, 9D1, 9E1, and 9F, the bone drill 910 defines four continuous helical flutes 920A, 920B, 920C, and 920D. In this embodiment, the splines 921A, 921B, 921C, and 921D are generally planar surfaces. In alternative embodiments, the splines 921A, 921B, 921C, and 921D have curved profiles with one or more concave or convex portions, S-shaped profiles, J-shaped profiles, and the like. Consistent with the parallelogram cross-sections shown in FIGS. 9D1, 9E1, the flutes 920A, 920B, 920C, and 920D form a bi-symmetrical rectilinear shape with flutes 920A and 920C being relatively equal and circumscribing the smallest arc, and flutes 920B and 920D being relatively equal and circumscribing the widest arc. Those skilled in the arc will recognize that the arc lengths may vary such that asymmetrical cross-sectional shapes can be defined in some embodiments. In this embodiment, these arcs will, again, display bi-symmetry and revolve around the axis at a relatively equal rate from shank to tip. In other embodiments, the flutes 920A, 920B, 920C, and 920D may become increasingly tighter or more numerous as they approach the tip 913 (or tighter at the shank end). The total number of turns per flute of the flutes 920A, 920B, 920C, and 920D from MnFD 917 (refer to cross-section A-A of FIGS. 9A1 and 9D1) to the MxFD 919 (refer to cross-section B-B of FIGS. 9A1 and 9E1) can depend on the total length of the working portion 912, but is generally not less than one-quarter of a complete revolution.

With further reference to FIGS. 9D1 and 9E1, it can be seen that the splines 921A, 921B, 921C, and 921D associated with flutes 920A, 920B, 920C, and 920D intersect at points 931A, 931B, 931C, and 931D. In this embodiment, the intersections 931A, 931B, 931C, and 931D define arcuate segments therebetween at angles of about 70 degrees, 110 degrees, 70 degrees, and 110 degrees. It should be understood, however, that other angles may be used in other embodiments, such that the shape of the transverse cross-section may become narrower, wider, asymmetrical, triangular, and so on. In addition, the shape of the transverse cross-sections may vary along the working length of the instrument. For example, the shape of a transverse cross-section near the shank may be rhomboidal and the shape of a transverse cross-section elsewhere may be a parallelogram as depicted in FIG. 9E1 (or another type of shape).

In this embodiment, splines 921A, 921B, 921C, and 921D form negative cutting angles tangent with the perimeter of shank 911. Alternatively, the splines may form a neutral or positive rake angle tangent with the perimeter of the shank 911.

It will also be recognized that splines 921A, 931B, 921C, and 921D may include concaved portions that can be formed to have various depths, shapes and may have a wide variety of configurations. The greatest depths of splines 921A, 921B, 921C, and 921D is affected by the width of the core 943, and the depths can be constant or variable along the working portion 912. The cross-sectional diameter of the core portion 943 is generally not narrower than about 20% percent of the diameter of the shank 911. However, in some embodiments the cross-sectional diameter of the core portion 943 can be narrower than about 20% percent of the diameter of the shank 911.

As stated above, the bone drill 910 is an example of a four-sided rotary offset bone drill that has the transverse cross-section of a parallelogram. In regard to the offset feature, and further referencing FIGS. 9D1, 9E1, and 9F, the drill 910 has a center-line or axis of rotation 940 (about which the drill 910 rotates when in use), and a mass axis 941 that does not consistently coincide with the axis of rotation 940. The mass axis 941 is a continuum of points defined by the centers of mass (centroids) of consecutive cross-sectional areas of the bone drill 910 along the working portion 912. The offset is the spatial difference between the mass axis 941 and the axis of rotation 940 (which are displaced a distance 942 away from each other near the shank 911). In this embodiment, the offset distance 942 decreases from the shank 911 to the tip 913, and is about zero at the end-point 946. This unique offset feature allows the instrument 910 to cut with a precessional motion, which can remove material in an envelope at least as large as cutting envelope 943, while using an instrument with a smaller cross-section 944. Accordingly, the bone drill 910 cuts a cavity in bone (or other material), and can prepare an osteotomy that remains generally cylindrical and corresponds to the MxFD 918, with a drill 910 that is substantially smaller in cross-section. In other embodiments, the offset distance 942 can be different, e.g., about zero at the shank 911 and increasing to the tip 913, or the offset may be essential consistent from shank to tip as shown, for example, in the embodiment of FIG. 7A-7F.

In some drill instrument embodiments having cross-sections shaped as a parallelogram, other spatial relationships can exist between the mass axis and the axis of rotation (that is, other than the distance 942 near the shank 911 and that decreases to about zero at the tip 913). For example, in some embodiments the mass axis can approximate a helical form that revolves around the axis of rotation. In other embodiments, the mass axis can form a spiral around the axis of rotation. In some embodiments, the mass axis can intersect the axis of rotation along a portion of the working length of the instrument, and can be offset from the axis of rotation along other portions of the working length. In particular embodiments, the mass axis intersects the axis of rotation at one or more points, while other points of the mass axis are offset from the axis of rotation. For example, in some embodiments the mass axis can form a wavy or curved shape that may intersect the axis of rotation at one or more points.

Referring to FIGS. 10A through 10I, an example apparatus 1014 for bone harvesting (also referred to herein as a bone basket) is provided, in conjunction with a bone drill 1010. The bone harvesting apparatus 1014 can be fit interchangeably over the working surface of bone drills, including but not limited to the example bone drill 1010 and other bone drills described herein, and connected and/or abutted to the shank of the drill itself. The bone harvesting apparatus 1014 is a telescopic appliance. That is, the apparatus 1014 can include multiple portions that can cooperate to form configurations that are axially extendable (e.g., FIG. 10B), axially retractable (e.g., FIG. 10H), and anywhere in between the extended and retracted configurations. This example bone harvesting apparatus 1014 has two portions that may be compared to or described, for example, as compartments or canisters.

Bone harvesting apparatus 1014 includes a proximally located canister 1021 and a distally located canister 1031. In this embodiment, the distal canister 1031 is slidable such that the distal canister 1031 can be positioned substantially within the interior region defined by the proximal canister 1021, such as when the apparatus 1014 is in the axially retracted configuration. The canisters 1021 and 1031 can be interconnected and stabilized with each other in various ways. For example, the canisters 1021 and 1031 can include complementary annular projections 1023 and 1032 respectively. In this embodiment, the proximal canister 1021 includes an annular projection 1023 that extends radially inward towards the axis of the canister 1021. The distal canister 1031 includes an annular projection 1032 that extends radially outward away from the axis of the canister 1031. The projections 1023 and 1032 are sized such that the distal canister 1031 is slidable within the proximal canister 1021, but wherein such sliding is limited in the distal direction by an interference between the projections 1023 and 1032. That is, the extent to which the canisters 1021 and 1031 can axially extend is limited by the physical contact and interference between the projections 1023 and 1032 as shown in FIG. 10A.

Still referring to FIGS. 10A through 10I, as described previously the bone drill 1010 can be coupled to the chuck of a rotary motorized tool or a handpiece via the shank end 1011 of the bone drill 1010. The working end of the bone drill 1010 can extend through the bone harvesting apparatus 1014, and pass through the distal end of the distal canister 1031 of the apparatus 1014 to reveal at least the tip of the drill 1010.

In some embodiments, a bone drill and bone harvesting basket apparatus are coupled together via a bearing or bushing whereby the drill is free to rotate relative to the bone basket. In this example, a bearing 1024/1025/1026 is located at the proximal collar 1013 of the proximal basket 1021 (refer to FIGS. 10A, 10E-10G, and 10I). The proximal end of the collar 1013 can be positioned to almost abut against the drill stop hub 1015 of the drill 1011. The outer race 1026 of the bearing 1024/1025/1026 is effectively coupled to the inner diameter of the proximal canister 1021 such that the outer race 1026 and proximal canister 1021 rotate together. In some embodiments, the outer race 1026 is coupled to the proximal canister 1021 using an interference press fit therebetween. In some embodiments, other coupling techniques are used, such as clamping, threading, using adhesive, and the like. In particular embodiments, this coupling can be selectively disassembled and reassembled by a user of the bone drill 1010 having the bone harvesting apparatus 1014. In alternative embodiments, the outer race 1026 and the proximal canister 1021 can be a unitary piece of material that is made by machining, welding, forming, and the like.

The inner race 1024 of the bearing 1024/1025/1026 is effectively coupled to the drill 1010 such that the inner race 1024 and drill 1010 rotate together. In the embodiment shown, the drill 1010 includes an annular groove 1016 located near the distal side of the drill stop 1015 in which the bearing 1024/1025/1026 is seated, although such a groove is not required. For example, in some embodiments a snap ring can be used to retain the inner race 1024 to the shank of the drill 1010 between the snap ring and the drill stop 1015.

The outer diameter of the proximal canister 1021 can be sized to readily fit through a drill guide, which acts to direct the longitudinal axis of the bone drill 1010.

Still referring to FIGS. 10A through 10I, in this embodiment, it is apparent that the bone basket 1021/1031 is telescopic and open-ended. As the drilling proceeds distally, the distal canister 1031 contacts bone or other tissue matter such that the distal canister 1031 is nudged to slide axially into the proximal canister 1021 to ultimately form the retracted configuration as shown in FIGS. 10G through 10I.

It should be understood that sleeves or canisters 1021 and 1031 can be perforated via openings 1025 and 1035, which are aligned to allow irrigating solution to flow continuously through the basket 1014 while the bone drill 1010 is turning. The perforation 1025 and 1035 are preferably smaller than the size of the bone chips created by the flutes of the bone drill 1010. It should also be understood that the rows of perforations 1025 and 1035 are installed at specific distances from the tip of the bone drill 1010 such that the perforations 1025 and 1035 can act as an intra-osseous depth gauge while drilling.

Since the drill 1010 is rotated relative to the canisters 1021 and 1031, the bone particles removed by the drilling flow in a proximal or upward direction and accumulate in the spaces between the canisters 1021 and 1031, such as the offset feature of the bone drill 1010 and the flutes that are encased by the bone harvesting basket 1014.

The basket 1014 can be removable and used either as an adjunct component to an osteotomy procedure enabling a clear and clean operating sight or, in instances when bone harvesting is desirable. Once the basket 1014 is removed from the drill 1010, the bone fragments should accessible from within the basket 1014 itself or retrievable from the flutes of the drill 1010.

Referring to FIGS. 12A through 12G, another example apparatus for bone harvesting 1250 is provided, in conjunction with an example bone drill 1210. The bone harvesting apparatus 1250 can be fit interchangeably over the working surface of bone drills, such as the example bone drill 1210, and connected and/or abutted to the shank of the drill itself. The bone harvesting apparatus 1250 is a telescopic appliance. That is, the apparatus 1250 can include multiple portions that can cooperate to form configurations that are axially extended (e.g., FIG. 12B), axially retracted (e.g., FIG. 12G), and anywhere in between the extended and retracted configurations. This example bone harvesting apparatus 1250 has three canisters: (i) a proximal canister 1221, (ii) an intermediate canister 1231, and (iii) a distal canister 1241.

In this embodiment, the distal canister 1241 is the largest in diameter, the proximal canister 1221 is the smallest in diameter, and the intermediate canister 1231 has a diameter that is between the diameters of the distal and proximal canisters 1241 and 1221. The diametrical relationships between the three canisters 1221, 1231, and 1241 allows the apparatus 1250 to axially extend and retract like a telescope. That is, the distal canister 1241 is slidable over the intermediate canister 1231 such that the intermediate canister 1231 can be positioned substantially within the interior region defined by the distal canister 1241. Likewise, the intermediate canister 1231 is slidable over the proximal canister 1221 such that the proximal canister 1221 can be positioned substantially within the interior region defined by the intermediate canister 1231 (and also substantially within the region defined by the distal canister 1241 [when the intermediate canister 1231 is positioned substantially within the interior region defined by the distal canister 1241]). When the canisters 1221, 1231, and 1241 are so positioned within each other, the apparatus 1250 is in the axially retracted configuration (e.g., FIG. 12G). In contrast, when the canisters 1221, 1231, and 1241 are not so positioned within each other, the apparatus 1250 is in the axially extended configuration (e.g., FIG. 12B) or partially extended configuration.

The canisters 1221, 1231, and 1241 can be interconnected with and stabilized by each other in various ways. For example, the canisters 1221, 1231, and 1241 can include complementary annular projections 1223, 1232, 1233, and 1242 (with intermediate canister 1231 having two annular projections—a proximal annular projection 1223 that extends radially inward and a distal annular projection 1233 that extends radially outward). The projections 1223, 1232, 1233, and 1242 are sized such that the canisters 1221, 1231, and 1241 are slidable with relation to each other, but wherein such sliding is limited in the distal direction by an interference between the projections 1223 and 1232, and between the projections 1233 and 1242. That is, the extent to which the canisters 1221, 1231, and 1241 can axially extend is limited by the physical contact and interference between the projections 1223, 1232, 1233, and 1242 as shown in FIG. 12A.

It should be understood that sleeves or canisters 1231 and 1241 can be perforated via openings 1235 and 1245, which are aligned to allow irrigating solution to flow continuously through the basket apparatus 1250 while the bone drill 1210 is turning. The perforation 1235 and 1245 are preferably smaller than the size of the bone chips created by the flutes of the bone drill 1210. It should also be understood that the rows of perforations 1235 and 1245 can be installed at specific distances from the tip of the bone drill 1210 such that the perforations 1235 and 1245 can act as an intra-osseous depth gauge while drilling. In this embodiment, the proximal canister 1221 does not have such perforations. This arrangement illustrates that such perforations are optional for the canisters of the bone harvesting apparatuses provided herein. The proximal canister 1221, being not perforated, can be advantageous for encasing and retaining the bone fragments captured in canisters 1231 and 1241.

In some embodiments, the drill 1210 rotates in relation to all three canisters 1221, 1231, and 1241. In some such embodiments, a bearing or bushing can be used between the proximal end of the proximal canister 1221 and the drill 1250 (as described above in reference to FIGS. 10A, 10E-10G, and 10I). In other embodiments, the proximal canister 1221 rotates with the drill 1250 while the intermediate canister 1231 and the distal canister 1241 do not rotate with the drill 1250. In such cases, a bearing or bushing can be used between the distal end of the proximal canister 1221 and the proximal end of the intermediate canister 1231.

Since the drill 1210 is rotated relative to at least the canisters 1231 and 1241, the bone particles removed by the drill 1250 will flow in a proximal or upward direction and accumulated in the flutes and/or the space defined by the offset feature of the bone drill 1210 and encased by the basket 1250.

The basket 1250 can be removable and used either as an adjunct to an osteotomy procedure enabling a clear and clean operating sight or, in those instances when bone harvesting is desirable. Once the basket 1250 is removed, the bone fragments are accessible within the basket 1250 itself, or retrievable from the flutes of the offset drill 1210.

Referring now to FIGS. 13A through 13G, another example apparatus for bone harvesting 1350 is provided, in conjunction with an example bone drill 1310. The bone harvesting apparatus 1350 can be fit interchangeably over the working surface of bone drills, such as the example bone drill 1310, and connected and/or abutted to the shank of the drill itself. The bone harvesting apparatus 1350 is a telescopic appliance. That is, the apparatus 1350 can include multiple portions that can cooperate to form configurations that are axially extended (e.g., FIG. 13B), axially retracted (e.g., FIG. 13G), and anywhere in between the extended and retracted configurations. As with the embodiment 1250 of FIGS. 12A through 12G described above, this example bone harvesting apparatus 1350 has three canisters: (i) a proximal canister 1321, (ii) an intermediate canister 1331, and (iii) a distal canister 1341.

In contrast to embodiment 1250 of FIGS. 12A through 12G, in this bone harvesting apparatus 1350 the proximal canister 1321 is the largest in diameter, the distal canister 1341 is the smallest in diameter, and the intermediate canister 1331 has a diameter that is between the diameters of the distal and proximal canisters 1341 and 1321. The diametrical relationships between the three canisters 1321, 1331, and 1341 allows the apparatus 1350 to axially extend and retract like a telescope. That is, the proximal canister 1321 is slidable over the intermediate canister 1331 such that the intermediate canister 1331 can be positioned substantially within the interior region defined by the proximal canister 1321. Likewise, the intermediate canister 1331 is slidable over the distal canister 1341 such that the distal canister 1341 can be positioned substantially within the interior region defined by the intermediate canister 1331 (and also substantially within the region defined by the proximal canister 1321 [when the intermediate canister 1331 is positioned substantially within the interior region defined by the proximal canister 1321]). When the canisters 1321, 1331, and 1341 are so positioned within each other, the apparatus 1350 is in the axially retracted configuration (e.g., FIG. 13G). In contrast, when the canisters 1321, 1331, and 1341 are not so positioned within each other, the apparatus 1350 is in the axially extended configuration (e.g., FIG. 12B) or partially extended configuration.

The canisters 1321, 1331, and 1341 can be interconnected with and stabilized by each other in various ways. For example, the canisters 1321, 1331, and 1341 can include complementary annular projections 1323, 1332, 1333, and 1342 (with intermediate canister 1331 having two annular projections—a proximal annular projection 1323 that extends radially outward and a distal annular projection 1333 that extends radially inward). The projections 1323, 1332, 1333, and 1342 are sized such that the canisters 1321, 1331, and 1341 are slidable with relation to each other, but wherein such sliding is limited in the distal direction by an interference between the projections 1323 and 1332, and between the projections 1333 and 1342. That is, the extent to which the canisters 1321, 1331, and 1341 can axially extend is limited by the physical contact and interference between the projections 1323, 1332, 1333, and 1342 as shown in FIG. 13A.

It should be understood that sleeves or canisters 1331 and 1341 can be perforated via openings 1335 and 1345, which are aligned to allow irrigating solution to flow continuously through the basket apparatus 1350 while the bone drill 1310 is turning. The perforation 1335 and 1345 are preferably smaller than the size of the bone chips created by the flutes of the bone drill 1310. It should also be understood that the rows of perforations 1335 and 1345 can be installed at specific distances from the tip of the bone drill 1310 such that the perforations 1335 and 1345 can act as an intra-osseous depth gauge while drilling. In this embodiment, the proximal canister 1321 does not have such perforations. This arrangement illustrates that such perforations are optional for the canisters of the bone harvesting apparatuses provided herein. The proximal canister 1321, being not perforated, can be advantageous for encasing canisters 1331 and 1341 and for retaining the bone fragments captured therein.

In some embodiments, the drill 1310 rotates in relation to all three canisters 1321, 1331, and 1341. In some such embodiments, a bearing or bushing can be used between the proximal end of the proximal canister 1321 and the drill 1350 (as described above in reference to FIGS. 10A, 10E-10G, and 10I). In other embodiments, the proximal canister 1321 rotates with the drill 1350 while the intermediate canister 1331 and the distal canister 1341 do not rotate with the drill 1350. In such cases, a bearing or bushing can be used between the distal end of the proximal canister 1321 and the proximal end of the intermediate canister 1331.

Since the drill 1310 is rotated relative to at least the canisters 1331 and 1341, the bone particles removed by the drill 1350 will flow in a proximal or upward direction and accumulated in the flutes and/or the space defined by the offset feature of the bone drill 1310 and encased by the basket 1350.

The basket 1350 can be removable and used either as an adjunct to an osteotomy procedure enabling a clear and clean operating sight or, in those instances when bone harvesting is desirable. Once the basket 1350 is removed, the bone fragments are accessible within the basket 1350 itself, or retrievable from the flutes of the offset drill 1310.

Figure 14B:
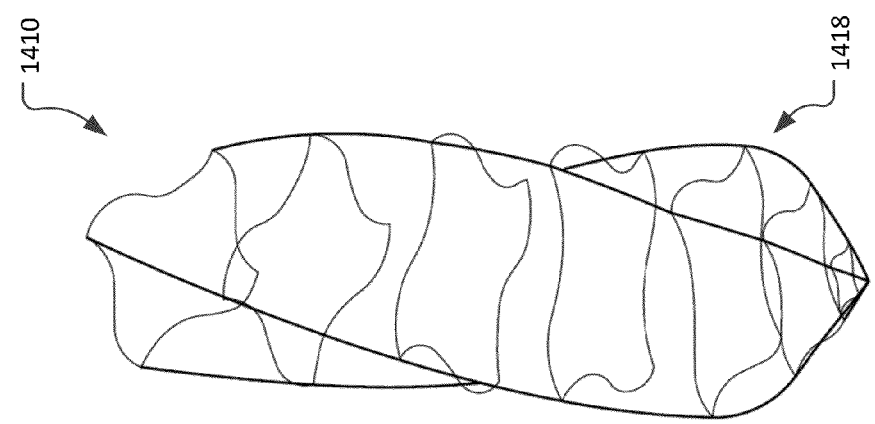
FIGS. 14A and 14B show tip portions of example bone drills having attenuated or rolled edges and an inactive or non-cutting tip.
Figure 14A:
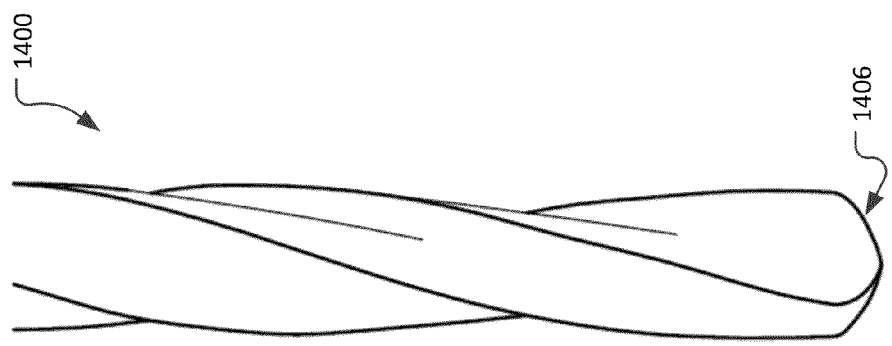

FIGS. 14A and 14B shows example distal portions of bone drills 1400 and 1410, in accordance with some embodiments, that retain the flutes along the some or all of the entire length of the working portion to maintain hauling action, while having the leading edge of the working portion modified such that the distal end of the working portion does not substantially cut bone. This modification is brought about by blunting or rolling the edges of flutes either at the tip or a portion of the shank or both, leaving the central portion of the working portion active. Rolling edges will prevent the instrument from over-enlarging or tearing the distal extent of the osteotomy distally and mitigate drag and premature fatigue proximally. FIG. 14A shows a non-cutting tip portion 1406 of the instrument 1400. FIG. 14B shows a non-cutting shank end portion 1418 of the instrument 1410.

Figure 15:
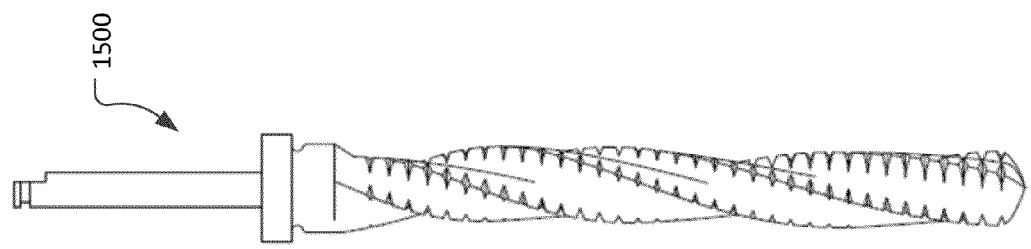
FIG. 15 shows an example of a four-sided bone drill having cross-cuts on its helices.

FIG. 15 shows another example bone drill 1500 in accordance with some embodiments. The example bone drill 1500 is a four-sided tapered bone drill with helices that include one or more cross cuts. The cross cuts can be (but are not required to be) at right angles to the helix. In general, the cross cuts can have a geometry and depth so as to increase the flexibility of the endodontic instrument 1500 to thereby allow the instrument 1500 to bend more easily. The cross cuts can have various different profile geometries, such as symmetrical v-channels, asymmetrical v-channels, radiused channels, rectangular channels, trapezoidal channels, and the like. The cross cuts can include cutting edges which, consequently, provide a more efficient cutting device 1500.

FIGS. 16A through 16C provide a series of illustrations that depict one procedure by which the bone drills provided herein may be used. FIG. 16A depicts a fractured long bone, such as a femur. FIG. 16B depicts an offset intramedullary drill (such as the bone drill embodiments provided herein) preparing the intramedullary space in the bone in preparation for the insertion of an intramedullary pin. FIG. 16C depicts the placement of an intramedullary pin and the fixation of the long bone in preparation for healing. It should be appreciated that FIGS. 16A through 16C provide just one example of a use for the bone drills provided herein, while numerous other uses are also envisioned.

FIGS. 11A-11H pertain to example materials and methods for making the bone drill instruments provided herein. In some embodiments, the bone drill instruments can be formed by starting with a blank, such as a metal blank, that is then shaped (e.g., by grinding, etc.) and otherwise treated to achieve a drilling instrument having a desired configuration. In some embodiments, the formed cutting portion may be plated, coated, or otherwise treated with diamond-like carbon, amorphous diamond, titanium nitride, or the like to enhance performance characteristics of the drilling instruments. In other embodiments, no coating is added. The instruments may be made from a variety of materials, including various types of stainless steels, super-elastic materials (e.g., nitinol), ceramics, and the like. In some embodiments, the drilling instruments provided herein have one or more longitudinal irrigation passages which pass through a collar portion of the drill and transverses a core or web of the drill exiting laterally and distally, wherein the passage is configured to allow flow of irrigation fluid to a lateral perimeter and tip of the drill. The drilling instruments provided herein may further include one or more depth markers or depth gauges on the drill body. FIGS. 11A-11D are examples of blanks of materials that can be ground to create the bone drills, and FIGS. 11E-11H are the cross-sectional profiles of the blanks of FIGS. 11A-11D respectively.

Referring to FIGS. 11A and 11E, an example blank 2510 has a substantially uniform cross-sectional geometry from a shank end 2514 to a tip end 2518. The cross-sectional geometry of the blank 2510 is asymmetrical with respect to the axis of rotation 2516 down the length of the blank 2510. Therefore, the centers of mass of the cross-sections do not lie on the axis of rotation 2516 along the length of the blank 2510. As the flutes are formed, such as by milling, machining, cutting, grinding or annealing and compressing, the relative distances between the flutes can be changed or the depths can be changed to achieve bone drill instruments that have an asymmetrical cross-section along its entire length, and may cut along a precessional axis as previously described in reference to the bone drill embodiments provided herein.

Referring to FIGS. 11B and 11F, a blank 2520 is shaped to have a different geometry at the shank end 2524 than at the tip end 2528. In this example, at the shank end 2524 the blank 2520 has a rectangular or square cross-section. At the tip end 2528, the blank 2520 takes on a triangular cross section. Between the triangular cross section and the rectangular cross section, the blank takes on a trapezoidal cross-section, that can have a centroid or center of mass that is located offset from the axis of rotation. As the flutes are formed, such as by milling, machining, cutting, grinding or annealing and compressing, the relative distances between the flutes can be changed or the depths can be changed to achieve the instrument that has a symmetrical, bisymmetrical or asymmetrical cross-section along its entire length. In some embodiments, drill instruments formed in such fashions may cut along a precessional axis as previously described in reference to the bone drill embodiments provided herein.

Referring to FIGS. 11C and 11G, a blank 2530 has a canted shape. At the shank end 2534, the blank 2530 has a center of mass (centroid) that is on a first axis 2540. Toward the tip end 2538, the blank 2530 has a center of mass (centroid) that is on a second axis 2542. The first axis 2540 is parallel to the second axis 2542, but the two axes 2540 and 2542 do not overlap or coincide with each other. If the drill instrument is cut essentially perpendicular to either of the axes 2540 and 2542, the cross-section of the instrument may be symmetrical. In some implementations, the blank is formed with a flexible metal, such as a shape-memory metal (e.g., nitinol), and the shape is achieved by machining the blank 2530, rather than bending the blank. As the flutes are formed, such as by milling, machining, cutting, grinding or annealing and compressing, the relative distances between the flutes can be changed or the depths can be changed to achieve the instrument that has a symmetrical, bisymmetrical or asymmetrical cross-section along its entire length such that the instrument may cut along a precessional axis as previously described in reference to the bone drill embodiments described above.

Referring to FIGS. 11D and 11H, a blank 2550 is cut (in at least in one plane) into a curved shape to form an instrument blank that has a curved profile. Alternatively, a selective flute (or flutes) may include a curved profile such that the instrument has a spiral, coil-like, or helical profile. As the flutes are formed, such as by milling, machining, cutting, grinding or annealing and compressing, the relative distances between the flutes can be changed or the depths can be changed to achieve the instrument that has a symmetrical, bisymmetrical or asymmetrical cross-section along its entire length, and such an instrument may cut along a precessional axis as previously described in reference to the bone drill embodiments provided herein.

A number of embodiments and implementations of the invention have been described. Nevertheless, it will be understood that various modifications may be made without departing from the spirit and scope of the invention. For example, in other implementations, similar instruments can have three, four, five, or six flutes. Further, the flute pattern can display a wide or narrow web or core, and can be of a variety of cross-sectional shapes such as triangular, rectilinear, trapezoidal, a parallelogram, rhomboidal, or radial and display negative, neutral, or positive rake angles. The shanks and/or metal blanks from which these instruments can be fabricated and have slightly larger diameters providing enough material to facilitate the increased number of flutes. The flutes, therefore, would require fewer spirals per unit length. Instruments of increasing size, or diameter, become increasingly less flexible. Implementing more flutes and/or cutting the flutes deeper into the metal blanks during manufacture can facilitate compensation for the decrease in flexibility. In addition, wider and deeper spaces also provide greater opportunity to haul out debris from the bone.

The working portion may include a number of variations including cross-cuts, rolled edges, and a reversed helix. The shank may be elongate with the working portion extending along only the distal extent of the device for access into long bones. The long shank without cutting flutes may be used for preparing the intermedullary space for intermedullary pin placement.

The materials used to fabricate these design may taken from a variety of resources, which include super-elastic materials such as Nickel-Titanium alloys, or stainless steel of various alloys, and other metallic materials that may be ground or machined or are moldable. Radiolucent materials such as ceramics are also envisioned for making bone drills within the scope of this disclosure.

Although the drills and reamers described in this document have been designated to cut boney materials, it should be understand that these designs may have a variety of other applications. For example, the instruments provided herein can be used in industrial applications in which a variety of materials are drilled. Such materials can include, but are not limited to, metals, ceramics, wood, plasterboard, plastics, stone, composites, synthetics, silicon, and the like.

Finally, it should be recognized that the deeper cross-sectional areas near the proximal end of an offset drilling device described herein offer an excellent opportunity to sequester and harvest bone. Implementations to capture that bone are also contemplated. In some embodiments, the bone chips are collected in a removable apparatus fixed to the distal portion of the drill, and the collected bone chips can be used for bone grafting.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:
1. A bone drill, comprising:
a shank configured to be releasably attachable to a motor to rotate the bone drill about an axis of rotation; and
a drill body extending directly from the shank, the drill body including a shank end where the drill body extends from the shank and a free end at an end of the drill body that is opposite of the shank end, the drill body including a cutting portion between the shank end and the free end, the drill body having a center of mass at each transverse cross-section of the drill body, wherein a center of mass of a transverse cross-section at the shank end is offset from the axis of rotation and a center of mass of a transverse cross-section at the free end lies on the axis of rotation.

2. The bone drill of claim 1, wherein the distance of the center of mass from the axis of rotation decreases linearly from the shank end to the free end.

3. The bone drill of claim 1, wherein the centers of mass of consecutive transverse cross-sections between the shank end and the free end form a mass path, and wherein at least a portion of the mass path is offset from the axis of rotation.

4. The bone drill of claim 1, wherein the centers of mass form a spiral around the axis of rotation.

5. The bone drill of claim 1, wherein the drill body is substantially constant diameter from the shank end to the free end.

6. The bone drill of claim 1, wherein the drill body is tapered from the shank end to the free end such that the shank end has a larger cutting diameter than the free end.

7. The bone drill of claim 1, wherein the drill body is tapered from the free end to the shank end such that the free end has a larger cutting diameter than the shank end.

8. The bone drill of claim 6 or 7, wherein the tapered body cuts along a dual axis, the dual axis comprising a first axis corresponding the central axis of rotation and a second axis corresponding to an offset mass path which rotates around the central axis.

9. The bone drill of claim 6 or 7, wherein the tapered body includes a first transverse cross-section and a second transverse cross-section, wherein the first transverse cross-section has a first geometry; and wherein the second transverse cross-section has a second geometry different from the first geometry.

10. The bone drill of claim 1, wherein the drill body includes a transverse cross-section that is asymmetrical, bisymmetrical, symmetrical, triangular, biangular, or quadrilateral.

11. The bone drill of claim 1, comprising a chisel tip at the free end of the drill body.

12. The bone drill of claim 11, wherein the chisel tip subtends an angle of greater than about 40 degrees.

13. The bone drill of claim 11, wherein an end of the chisel tip is on the axis of rotation.

14. The bone drill of claim 11, wherein an end of the chisel tip is offset from the axis of rotation.

15. The bone drill of claim 11, wherein the chisel tip includes a plurality of inclined planes at substantially equal inclination.

16. The bone drill of claim 11, wherein the chisel tip includes a first inclined plane and a second included plane with a different inclination than the first inclined plane.

17. The bone drill of claim 1, wherein a portion of the drill body near the free end has blunted cutting edges.

18. The bone drill of claim 1, wherein the bone drill is comprised of a super-elastic alloy.

19. The bone drill of claim 1, wherein the cutting portion is sized to prepare an osteotomy having a diameter within a range of about 1.5 millimeters to about 8.0 millimeters.

20. The bone drill of claim 1, wherein the bone drill is sized to prepare an osteotomy having a depth sufficient to receive dental implants with lengths ranging from about 8 millimeters to about 18 millimeters.

21. The bone drill of claim 1, wherein the cutting portion is coated with diamond, diamond compact bits, or diamond-like carbon.

22. The bone drill of claim 1, wherein the cutting portion is coated with amorphous diamond.

23. The bone drill of claim 1, wherein the cutting portion is coated with titanium nitride, titanium aluminum nitride, titanium carbon nitride, zirconium nitride or black oxide.

24. The bone drill of claim 1, having at least one longitudinal irrigation passage which passes through a collar portion of the bone drill and transverses a core or web of the drill exiting laterally and distally, wherein the passage is configured to allow flow of irrigation fluid to a lateral perimeter and tip of the bone drill.

25. The bone drill of claim 1, further comprising one or more depth markers or depth gauges on the drill body.

26. The bone drill of claim 1, wherein the centers of mass of consecutive transverse cross-sections between the shank end and the free end form a mass path, and wherein at least a portion of the mass path is linear.

27. A bone drill, comprising:
a shank configured to be releasably attachable to a motor to rotate the bone drill about an axis of rotation; and
a drill body extending directly from the shank, the drill body including a shank end where the drill body extends from the shank and a free end at an end of the drill body that is opposite of the shank end, the drill body including a cutting portion between the shank end and the free end, the drill body having a center of mass at each transverse cross-section of the drill body, wherein a center of mass of a transverse cross-section at the shank end is offset from the axis of rotation and a center of mass of a transverse cross-section at the free end is offset from the axis of rotation, and wherein a distance from a center of mass of each transverse cross-section between the shank end and the free end is offset from the axis of rotation by a substantially consistent distance.

28. The bone drill of claim 27, wherein the centers of mass of consecutive transverse cross-sections between the shank end and the free end form a mass path, and wherein the mass path comprises a helix.

29. The bone drill of claim 27, wherein the centers of mass of consecutive transverse cross-sections between the shank end and the free end form a mass path, and wherein at least a portion of the mass path is linear.

30. The bone drill of claim 27, wherein the drill body is substantially constant diameter from the shank end to the free end.

31. The bone drill of claim 27, wherein the drill body is tapered from the shank end to the free end such that the shank end has a larger cutting diameter than the free end.

32. The bone drill of claim 31, wherein the tapered body includes a first transverse cross-section and a second transverse cross-section, wherein the first transverse cross-section has a first geometry; and wherein the second transverse cross-section has a second geometry different from the first geometry.

33. The bone drill of claim 31, wherein the tapered body cuts along a dual axis, the dual axis comprising a first axis corresponding the central axis of rotation and a second axis corresponding to an offset mass path which rotates around the central axis.

34. The bone drill of claim 27, wherein the drill body is tapered from the free end to the shank end such that the free end has a larger cutting diameter than the shank end.

35. The bone drill of claim 34, wherein the tapered body includes a first transverse cross-section and a second transverse cross-section, wherein the first transverse cross-section has a first geometry; and wherein the second transverse cross-section has a second geometry different from the first geometry.

36. The bone drill of claim 34, wherein the tapered body cuts along a dual axis, the dual axis comprising a first axis corresponding the central axis of rotation and a second axis corresponding to an offset mass path which rotates around the central axis.

37. The bone drill of claim 27, wherein the drill body includes a transverse cross-section that is asymmetrical, bisymmetrical, symmetrical, biangular, triangular, or quadrilateral shaped.

* * * * *

UNITED STATES PATENT AND TRADEMARK OFFICE
CERTIFICATE OF CORRECTION

PATENT NO.        : 9,271,740 B2
APPLICATION NO.   : 14/464597
DATED             : March 1, 2016
INVENTOR(S)       : Scianamblo It is certified that error appears in the above-identified patent and that said Letters Patent is hereby corrected as shown below:

In the Claims

In Claim 16, column 35, line 50, delete "included" and insert -- inclined --.

Signed and Sealed this
Twenty-first Day of June, 2016

Michelle K. Lee
*Director of the United States Patent and Trademark Office*